US008358818B2

(12) United States Patent
Miga et al.

(10) Patent No.: US 8,358,818 B2
(45) Date of Patent: Jan. 22, 2013

(54) APPARATUS AND METHODS OF COMPENSATING FOR ORGAN DEFORMATION, REGISTRATION OF INTERNAL STRUCTURES TO IMAGES, AND APPLICATIONS OF SAME

(75) Inventors: Michael I. Miga, Franklin, TN (US); Logan W. Clements, Nashville, TN (US); Robert L Galloway, Jr., Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1163 days.

(21) Appl. No.: 11/985,526

(22) Filed: Nov. 15, 2007

(65) Prior Publication Data

US 2008/0123927 A1 May 29, 2008

Related U.S. Application Data

(60) Provisional application No. 60/859,438, filed on Nov. 16, 2006.

(51) Int. Cl.
*G06K 9/00* (2006.01)
(52) U.S. Cl. .......................... 382/128; 382/131; 600/407
(58) Field of Classification Search .................... 382/128
See application file for complete search history.

(56) References Cited

U.S. PATENT DOCUMENTS

| 6,584,339 | B2 | 6/2003 | Galloway, Jr. et al. |
| 7,072,707 | B2 | 7/2006 | Galloway, Jr. et al. |
| 7,327,865 | B2 * | 2/2008 | Fu et al. ........................ 382/128 |
| 2004/0009459 | A1 | 1/2004 | Anderson et al. |
| 2004/0059217 | A1 | 3/2004 | Kessman et al. |
| 2005/0101855 | A1 | 5/2005 | Miga |
| 2007/0086659 | A1 * | 4/2007 | Chefd'hotel et al. ......... 382/225 |
| 2007/0167699 | A1 * | 7/2007 | Lathuiliere et al. ........... 600/407 |

OTHER PUBLICATIONS

Cash, D. M., et al., Compensating for Intraoperative Soft-Tissue Deformations Using Incomplete Surface Data and Finite Elements, IEEE Transactions on Medical Imaging, Nov. 2005, vol. 24, pp. 1479-1491, No. 11, ISSN 0278-0062.
Clements, L. W. et al., Robust Surface Registration Using Salient Anatomical Features in Image-Guided Liver Surgery, Medical Imaging 2006: Visualization, Image-guided Procedures, and Display: Proc. of the SPIE, Sep. 1, 2006, pp. 1-11.
M. I. Miga et al., "Incorporation of surface-based deformations for updating images intraoperatively," SPIE Medical Imaging 2001: Visualization, Display, and Image-guided Procedures San Diego, CA: SPIE, 2001.

(Continued)

*Primary Examiner* — Phillip A Johnston
(74) *Attorney, Agent, or Firm* — Morris Manning & Martin, LLP; Tim Tingkang Xia, Esq.

(57) ABSTRACT

A method and system of compensation for intra-operative organ shift of a living subject usable in image guide surgery. In one embodiment, the method includes the steps of generating a first geometric surface of the organ of the living subject from intra-operatively acquired images of the organ of the living subject, constructing an atlas of organ deformations of the living subject from pre-operatively acquired organ images from the pre-operatively acquired organ images, generating a second geometric surface of the organ from the atlas of organ deformations, aligning the second geometric surface of the organ to the first geometric surface of the organ of the living subject to determine at least one difference between a point of the first geometric surface and a corresponding point of the second geometric surface of the organ of the living subject, which is related to organ shift, and compensating for the intra-operative organ shift.

27 Claims, 43 Drawing Sheets
(16 of 43 Drawing Sheet(s) Filed in Color)

OTHER PUBLICATIONS

F. J. Carter et al., "Measurements and modelling of the compliance of human and porcine organs," Medical Image Analysis, vol. 5, pp. 231-236, Dec. 2001.

M. Stevanovic et al., "Modeling contact between rigid sphere and elastic layer bonded to rigid substrate," IEEE Trans on Components and Package Technologies, vol. 24, No. 2, pp. 207-212, 2001.

A. J. Herline et al., "Image-guided surgery: Preliminary feasibility studies of frameless stereotactic liver surgery," Arch. Surg., vol. 134, pp. 644-650, 1999.

A. J. Herline et al., "Surface registration for use in interactive, image-guided liver surgery," Springer-Verlag Berlin Heidelberg, pp. 892-899, 1999.

P. J. Besl et al., "A method for registration of 3-d shapes," IEEE Trans. on Pattern Anal. and Machine Intell. vol. 14, No. 2, pp. 239-256, 1992.

D. M. Cash et al., "Incorporation of a laser range scanner into image-guided liver surgery: Surface acquisition, registration, and tracking," Med. Phys., vol. 30, No. 7, pp. 1671-1682, 2003.

D. M. Cash et al., "Compensating for intraoperative soft-tissue deformations using incomplete surface data and finite elements," IEEE Trans. on Med. Imaging, vol. 24. No. 11, pp. 1479-1491, 2005.

C. R. Maurer, Jr. et al., "Registration of 3-d images using weighted geometrical features," IEEE Trans. on Med. Imaging, vol. 15, No. 6, pp. 836-849, 1996.

K. S. Arun et al., "Least-squares fitting of two 3-d point sets," IEEE Trans. on Pattern Anal. and Mach. Intell., vol. 9, No. 5, pp. 698-700, 1987.

S. J. Ahn et al., "Orthogonal distance fitting of implicit curves and surfaces," IEEE Trans. on Pattern Anal. and Mach. Intell., vol. 24. No. 5, pp. 620-638, 2002.

L. A. Platenik et al., "In vivo quantification of retraction deformation modeling for updated image-guidance during neurosurgery," IEEE Trans. on Biomed. Eng., vol. 49, No. 8, pp. 823-835, Aug. 2002.

S. Balay et al., Efficienct Management of Parallelism in Object-Oriented Numerical Software Libraries, Cambridge, MA: Birkhauser, 1997, pp. 163-202.

Y. Saad et al., "GMRES: A generalized minimal residual algorithm for solving nonsymmetric linear systems," SIAM J. Sci. Statist. Comput., vol. 7, No. 3, 1986, pp. 856-869.

J. Fitzpatrick et al., "Predicting error in rigid-body, point-based registration," IEEE Trans. Med. Imag., vol. 17, No. 5, pp. 694-702, Oct. 1998.

A. E. Johnson et al., "Registration and integration of textured 3D data," Image and vis. Comput., vol. 17, No. 2, pp. 135-147, Feb. 1999.

G. C. Sharp et al., "ICP registration using invariant features," IEEE Trans. Pattern Anal. Mach. Intell., vol. 24, No. 1, pp. 90-102, Jan. 2002.

G. Godin et al., "A method for the registration of attributed range images," Proc. 3DIM 2001, May 2001, pp. 179-186.

P. Bao et al., "Ultrasound-to computer-tomography registration for image-guided laparoscopic liver surgery," Surgical Endosc., 2005, vol. 19, pp. 424-429.

R. Malladi et al., "Shape modeling with front propagation: A level set approach," IEEE Transactions on Pattern Analysis and Machine Intelligence, vol. 17, No. 2, pp. 158-175, 1995.

J. Carr et al., "Smooth surface reconstruction from noisy range data," ACM Graphite 2003, Melbourne, Australia, 2003, pp. 119-126.

T. Hartkens et al., "Measurement and analysis of brain deformation during neurosurgery," IEEE Transactions on Medical Imaging, vol. 22, No. 2, pp. 82-92, Jan. 2003.

A. Nabavi et al., "Serial intraoperative magnetic resonance imaging of brain shift," Neurosurgery, vol. 48, No. 4, pp. 787-797, 2001.

A. Nabavi et al., "Image-guided therapy and intraoperative MRI in neurosurgery," Minimally Invasive Therapy & Allied Technologies, vol. 9(3/4), pp. 277-286, Aug. 2000.

C. Nimsky et al., "Intraoperative magnetic resonance tomography—experiences in neurosurgery," Nervenarzt, vol. 71, pp. 987-994, 2000.

C. Nimsky et al., "Quantification of, visualization of, and compensation for brain shift using intraoperative magnetic resonance imaging," Neurosurgery, vol. 47, No. 5, pp. 1070-9; discussion 1079-80., 2000.

A. L. Bradley et al, "Surgical experience with hepatic colorectal metastasis," Am. Surg., vol. 65, pp. 560-567, 1999.

J. Scheele et al., "Resection of colorectal liver metastasis," World J. Surg., vol. 19, pp. 59-71, 1995.

M. D. Stone et al., "Surgical therapy for recurrent liver metastases from colorectal cancer," Arch Surg, vol. 125, pp. 718-722, 1990.

J. O. Garden et al., "Anatomy of the liver," Hepatobiliary and Pancreatic Surgery, 5th Edition, S. D. Carter, Ed. London: Chapman and Hall Medical, 1996, pp. 1-4.

P. A. Sheiner et al., "Treatment of metastatic cancer to the liver," Seminars in liver Disease, vol. 14, No. 2, pp. 169-177, 1994.

J. Yamamoto et al., "Pathologic support for limited hepatectomy in the treatment of liver metastases from colorectal cancer," Ann. Surg., vol. 221, No. 1, pp. 74-78, 1995.

R. P. DeMatteo et al., "Anatomic segmental hepatic resection is superior to wedge resection as an oncologic operation for colorectal liver metastates," J. Gastrointest. Surg., vol. 4, No. 2, pp. 178-184, 2000.

T. U. Cohnert et al., "Preoperative risk assessment of hepatic resection for malignant disease," World J. Surg., vol. 21, pp. 396-400, 1997.

W. R. Jarnagin et al., "Improvement in perioperative outcome after hepatic resection: analysis of 1803 consecutive cases over the past decade," Ann. Surg., vol. 236, No. 4, pp. 397-407, 2002.

C. Laurent et al., "Influence of postoperative morbidity on long-term survival following liver resection for colorectal metastases," Br. J. Surg., vol. 90, pp. 1131-1136, 2003.

M. J. Schindl et al., "The value of residual liver volume as a predictor of hepatic dysfunction and infection after major liver resection," Gut, vol. 54, pp. 289-296, 2005.

T. Sunthau et al., "A concept for augmented reality visualization based on a medical application in liver surgery," Proc. of the ISPRS Commision V Symposium, Corfu, Greece, 2002, pp. 274-280.

Y. Masutani et al, "Modally controlled free form deformation for non-rigid registration in image-guided liver surgery," Medical Image Computing and Computer-Assisted Inverventions 2001. vol. 2208, S. Verlag, Ed. Berlin, 2001, pp. 1275-1278.

N. Ayache, "Epidaure: a research project in medical image analysis, simulation, and robotics at INRIA," IEEE Trans. on Med. Imaging, vol. 22, No. 10, pp. 1185-1201, 2003.

J. M. Blackall et al., "A statistical model of respiratory motion and deformation of the liver," Medical Image Computing And Computer Assisted Interventions 2001. vol. 2208, S. Verlag, Ed. Berlin: Springer Verlag, 2001, pp. 1338-1340.

G. P. Penney et al., "Registration of freehand 3D ultrasound and magnetic resonance liver images," Medical Image Analysis, vol. 8, pp. 81-91, 2004.

P. Bao et al., "Ultrasound-to-computer-tomography registration for image-guided laparoscopic liver surgery," Surg. Endosc., pp. 424-429, vol. 19, electronic publication, 2005.

B. B. Frericks et al., "3D CT modeling of hepatic vessel architecture and volume calculation in living donated liver transplantation," Eur Radiol, vol. 14, pp. 326-333, 2004.

H. Lang et al., "Extended left hepatectomy—modified operation planning based on three-dimensional visualization and liver anatomy," Langenbecks Arch Surg., vol. 389, pp. 306-310, 2004.

D. Selle et al., "Analysis of vasculature of liver surgical planning," IEEE Trans. on Med. Imaging, vol. 21, No. 11, pp. 1344-1257, 2002.

D. Knaus et al., "System for laparoscopic tissue tracking," International Symposium on Biomedical Imaging 2006 Washington, D.C.: IEEE, 2006.

Z. Cao, "Segmentation of medical images using level set-based methods," Pro Quest Dissertations and Theses, Electrical Engineering, Computer Engineering, and Computer Science Nashville: Vanderbilt University, 2004.

L. Hermoye et al., "Liver segmentation in living liver transplant donors: Comparison of semiautomatic and manual methods," Radiology, vol. 234, pp. 171-178, Jan. 2005.

W. Lorensen et al., "Marching cubes: A high resolution 3d surface construction algorithm," ACM Computer Graphics, vol. 21, No. 4, pp. 163-169, 1987.

J. L. Bentley, "Multidimensional binary search trees used for associative searching," Communications of the ACM, vol. 18, No. 9, pp. 509-517, 1975.

Z. Zhang, "Iterative point matching for registration of free-form curves and surfaces," Int. J. of Computer Vision, vol. 13, No. 2, pp. 119-152, 1994.

D. M. Cash et al., "Fast, accurate surface acquisition using a laser range scanner for image-guided liver surgery," Medical Imaging 2002: Visualization, display, and image-guided procedures: Proc. of the SPIE 2002, vol. 4681, pp. 100-110, 2002.

D. M. Cash et al., "Incorporation of a laser range scanner into image-guided liver surgery: Surface acquisition, registration, and tracking," Medical Physics, vol. 30, No. 7, pp. 1671-1682, Jul. 2003.

D. M. Cash et al., "Compensating for Intraoperative Soft-Tissue Deformations Using Incomplete Surface Data and Finite Elements," IEEE Trans. on Medical Imaging, vol. 24, No. 11, pp. 1479-1491, Nov. 2005.

B. M. Dawant et al., "Robust segmentation of medical images using geometric deformable models and a dynamic speed function," Medical Image Computing and Computer-Assisted Intervention 2001. vol. 2208, N. a. Viergever, Ed.: Springer Verlag, 2001.

P. J. Besl et al., "A Method for Registration of 3-D Shapes," IEEE Transactions on Pattern Analysis and Machine Intelligence, vol. 14, No, 2, pp. 239-256, 1992.

H. Chui et al., "A new point matching algorithm for non-rigid registration," Computer Vision and Image Understanding, vol. 89, pp. 114-141, 2003.

Logan W. Clements et al., Robust surface registration using salient anatomical features for image-guided liver surgery: Algorithm and validation, Med. Phys., vol. 35, No. 6, pp. 2528-2540, Jun. 2008.

J. P. W. Pluim et al., "Image registration by maximization of combined mutual information and gradient information," IEEE Transactions on Medical Imaging, vol. 19, No. 8, pp. 809-814, Aug. 2000.

S. Sgouros et al., "The clinical value of electroencephalogram/magnetic resonance imaging co-registration and three-dimensional reconstruction in the surgical treatment of epileptogenic lesions," Childs Nervous System, vol. 17, pp. 139-144, 2001.

M. I. Miga et al., "Intraoperative registration of the liver for image-guided surgery using laser range scanning and deformable models," Medical Imaging 2003: Visualization, Image-guided Procedures, and Display, San Diego, 2003, pp. 350-359.

L. W. Clements et al., "Robust surface registration using salient anatomical features in image-guided liver surgery," Proc. of SPIE: Medical Imaging 2006, vol. 6141, Feb. 11-16, 2006.

P. Dumpuri et al., "Model-updated image guidance: A statistical approach to gravity-induced brain shift," in Medical Image Computing and Computer-Assisted Intervention-Miccai 2003, Pt 1. vol. 2878 Berlin: Springer-Verlag Berlin, 2003, pp. 375-382.

P. Dumpuri et al., "An atlas-based method to compensate for brain shift: Preliminary results," Medical Image Analysis, vol. 11, pp. 128-145, 2007.

P. Dumpuri et al., "Automated brain shift correction using a pre-computed deformation atlas," Proc. of SPIE: Medical Imaging 2006, vol. 6141, Feb. 11-16, 2006.

C. Davatzikos, "Measuring biological shape using geometry-based shape transformations," Image and Vision Computing, vol. 19, pp. 63-74, 2001.

C. Davatzikos et al., "Convexity analysis of active contour problems," Image and Vision Computing, vol. 17, pp. 27-36, 1999.

C. Davatzikos et al., "A framework for predictive modeling of anatomical deformations," IEEE Transactions on Medical Imaging, vol. 20, No. 8, pp. 836-843, 2001.

S. K. Kyriacou et al., "A biomechanical model of soft tissue deformation, with applications to non-rigid registration of brain images with tumor pathology," Medical Image Computing and Computer-Assisted Intervention-Miccai '98, vol. 1496, pp. 531-538, 1998.

S. K. Kyriacou et al., "A framework for predictive modeling of intra-operative deformations: A simulation-based study," Medical Image Computing and Computer-Assisted Intervention-Miccai 2000, vol. 1935, pp. 634-642, 2000.

* cited by examiner

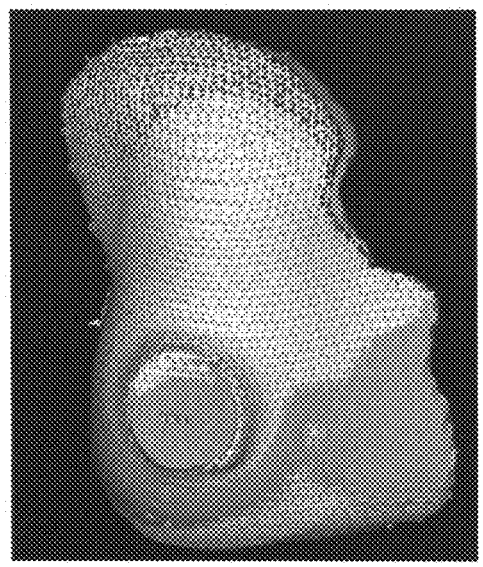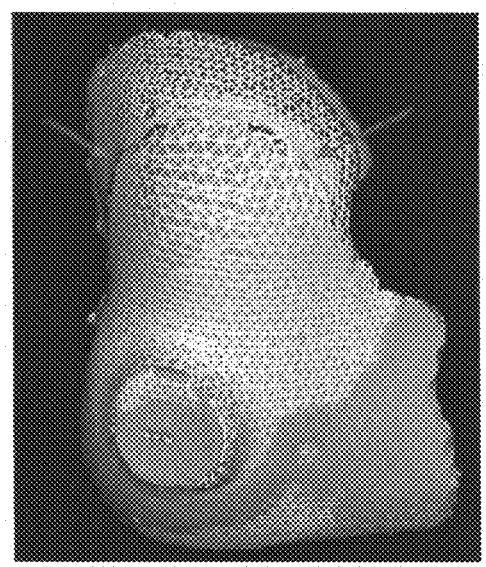
Fig. 8

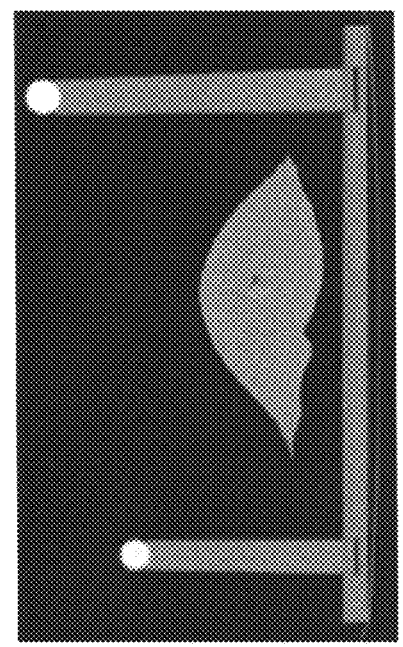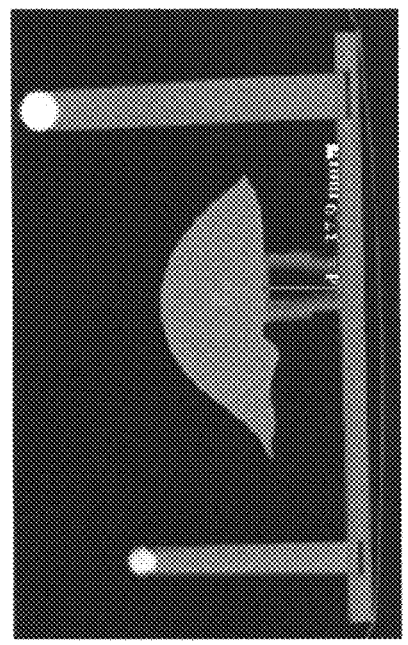
Fig. 15

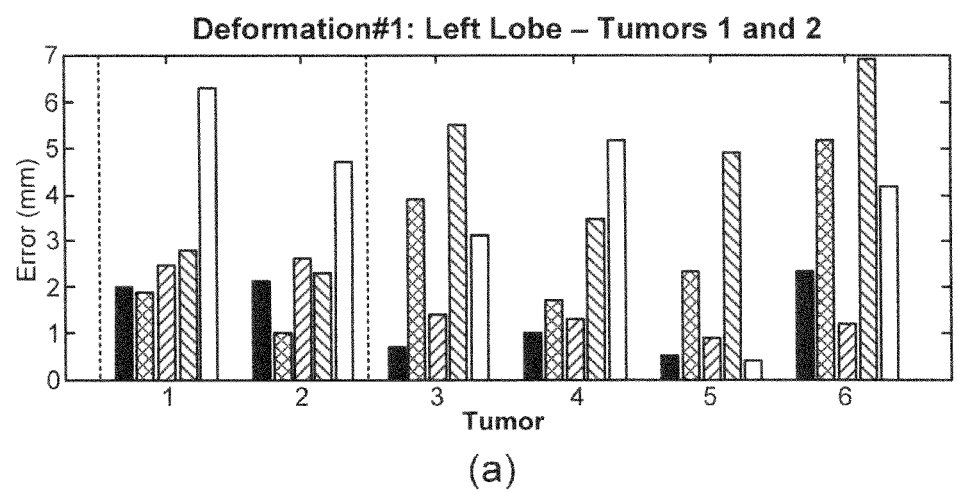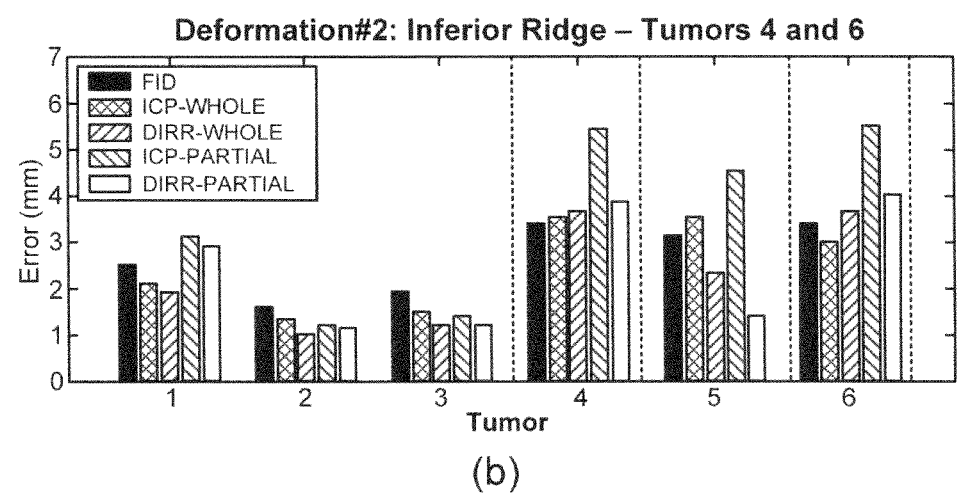
Fig. 21

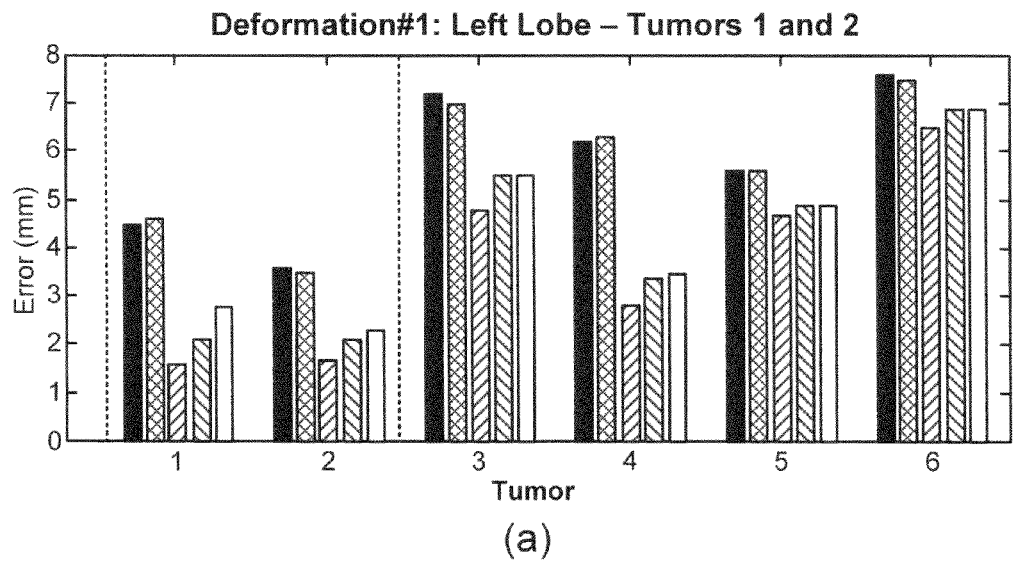
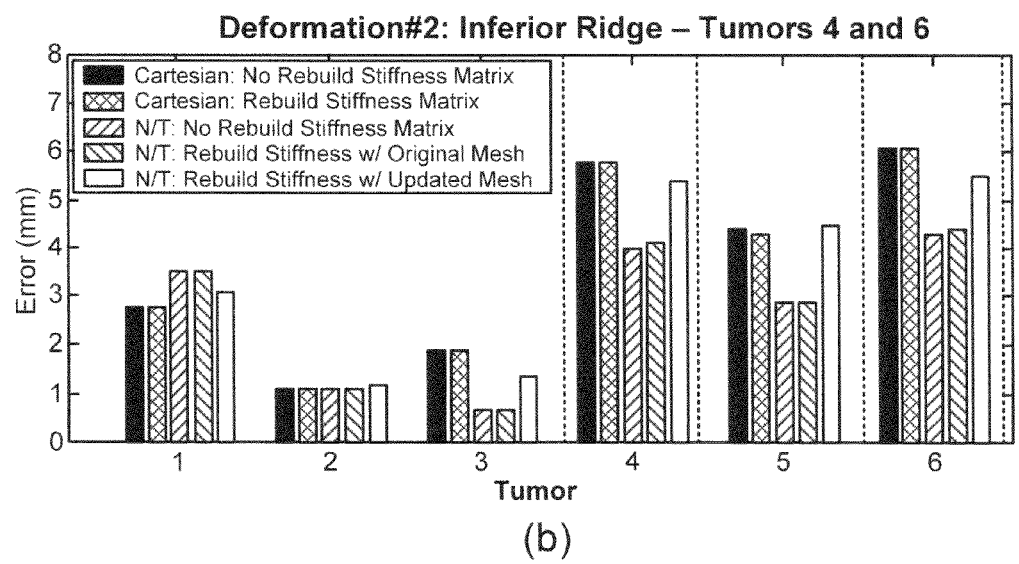
Fig. 23

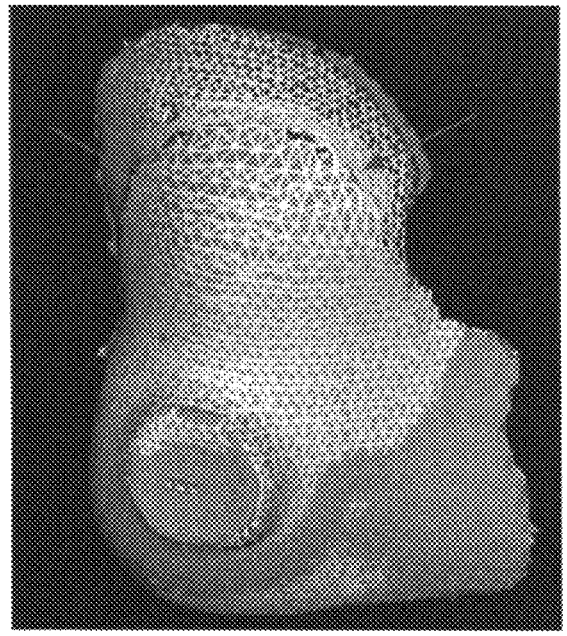
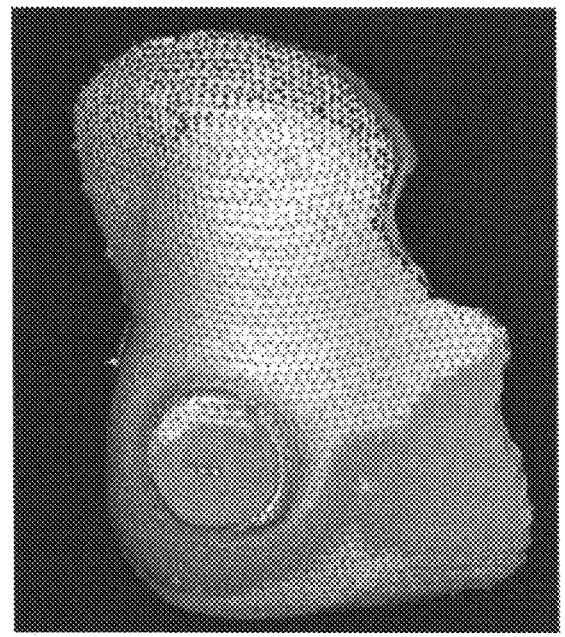
Fig. 24

(a) Original Slice
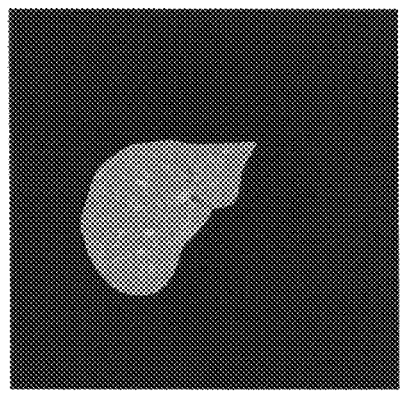
(b) Manual Segmentation
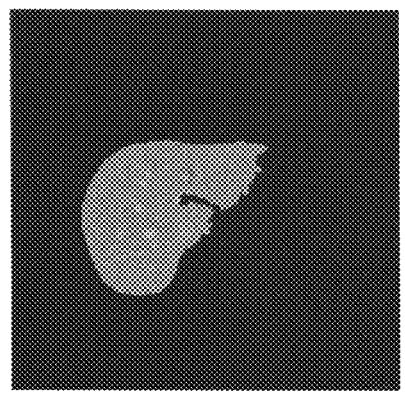
(c) Level Set Segmentation
Fig. 34

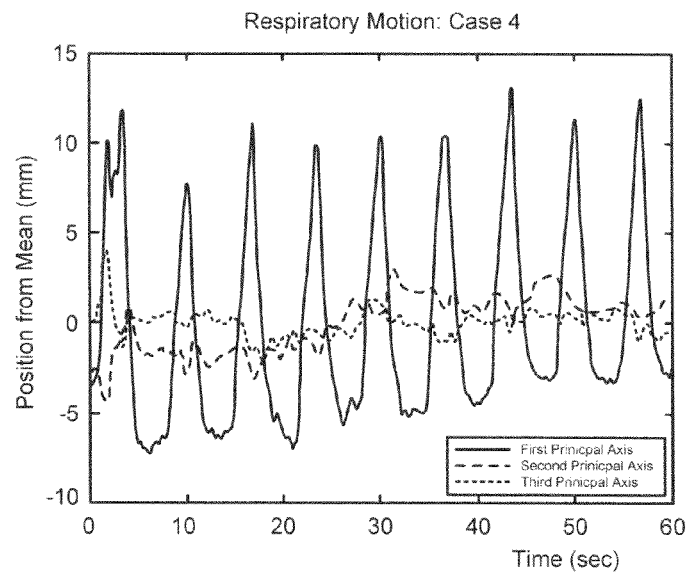
(a) Case 4
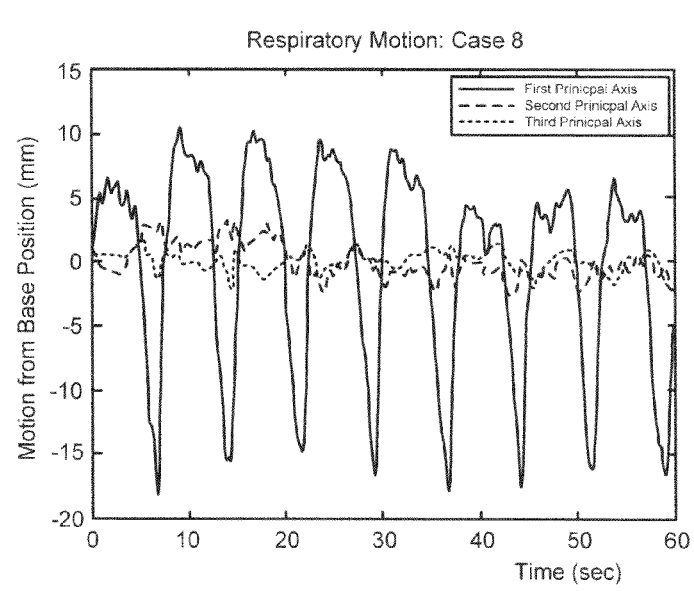
(b) Case 8
Fig. 38

US 8,358,818 B2

APPARATUS AND METHODS OF COMPENSATING FOR ORGAN DEFORMATION, REGISTRATION OF INTERNAL STRUCTURES TO IMAGES, AND APPLICATIONS OF SAME

CROSS-REFERENCE TO RELATED PATENT APPLICATION

This application claims the benefit, pursuant to 35 U.S.C. §119(e), of U.S. provisional patent application Ser. No. 60/859,438, filed Nov. 16, 2006, entitled "APPARATUS AND METHODS FOR COMPENSATING FOR ORGAN DEFORMATION, APPARATUS AND METHODS FOR REGISTRATION OF INTERNAL STRUCTURES TO IMAGES, AND APPLICATIONS OF SAME," by Michael I. Miga, Logan Clements and Robert L. Galloway Jr., which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [67] represents the 67th reference cited in the reference list, namely, D. M. Cash, T. K. Sinha, W. C. Chapman, H. Terawaki, B. M. Dawant, J. Robert L. Galloway, and M. I. Miga, "Incorporation of a laser range scanner into image-guided liver surgery: Surface acquisition, registration, and tracking," Med. Phys. 30, pp. 1671-1682, 2003.

STATEMENT OF FEDERALLY-SPONSORED RESEARCH

This invention was made with Government support under Contract Nos. R21 CA91352 awarded by the National Institute of Health, Contract No. 5R33 CA091352-04 awarded by the National Institute of Health, Contract No. 4R44 CA115263 awarded by the National Institute of Health, and Contract No. R21 EB007694 awarded by the National Institute of Health. The Government has certain rights in the invention.

FIELD OF THE INVENTION

The present invention generally relates to image-guided surgery, and in particular to apparatus and methods of compensation for soft tissue deformation in relation to image-guided surgery in one aspect, and apparatus and methods of compensation for registration of internal structures to images in relation to image-guided surgery in another aspect.

BACKGROUND OF THE INVENTION

Image-guided surgery (IGS) involves patient-specific anatomical images pre-operatively acquired that spatially localize pathology, digitization technology that allows the identification and tracking of targeted points of interest in a patient's physical space in an operating room (OR), and alignments of the patient-specific images to the patient's physical space in the OR such that the digitization technology can be referenced to the patient-specific images and used for guidance during surgery. Central to the IGS is the method of registering an image space (a coordinate system corresponding to the pre-operative images) to a physical space (a coordinate system corresponding to the intra-operative anatomy of the patient). Once the registration is performed, all pre-operative planning and acquired data related to the patient's anatomy could be displayed intra-operatively to a surgeon and used for assistance in surgical guidance and treatment.

In the recent years, there have been several detailed studies that have illustrated the need for soft-tissue deformation correction within image-guided neurosurgery [1-5]. With respect to the extracranial environment quantitative data is limited, nevertheless, there is a growing acceptance that to translate image-guided interventions to the extracranial environment (e.g. abdominal organs such as the liver), the need to correct for soft tissue deformation may be essential. While intraoperative magnetic resonance (iMR) and computed tomography (iCT) are available, these approaches are somewhat cumbersome and are not economically scalable to mid-level medical centers.

On the other hand, hepatic tumors represent a major health care problem in the U.S. Along with hepatocellular cancer, many primary neoplasms metastasize to the liver. In fact, the most common tumor treated in the liver is metastatic colorectal carcinoma, a condition where hepatic metastasectomy can result in long-term survival in properly selected patients. This is a frequent problem and the incidence of hepatic resection for colorectal cancer metastasis is increasing [6, 7]. For example, it is estimated that 150,000 new cases of colorectal cancer will present each year in the United States, from which 50% will develop metastatic disease [8]. Of patients with colorectal metastases, 60% will have hepatic involvement. Liver metastases occur in many patients with other primary malignancies (e.g. breast cancer) and are a frequent cause of cancer-related deaths. Unfortunately, it is estimated that there are only 6,000 to 12,000 patients who would be deemed resectable using current techniques [9]. These figures do not include the nearly 19,000 patients with primary intrahepatic malignant tumors [10]. Interestingly, in reviewing the patient base with potentially resectable colorectal metastases, the number of candidates who actually undergo resection is surprisingly low. This discrepancy may result from many factors, but is most likely influenced by the magnitude and complexity of hepatic resections as it iscurrently performed. Surgical therapy does improve survival for patients with hepatic colorectal metastasis and is largely considered to be more effective than chemotherapy [8, 9].

In these procedures, a large incision through the abdomen is created to expose the anterior surface of the liver. Either wedge or segmental liver resections are performed to remove one or more hepatic metastases. In wedge resections, the tumor and a 2-3 cm surrounding region of the liver is removed, while in segmental resection, an entire anatomic segment of the liver is removed. Each of the eight segments of the liver is supplied by its own portal venous and hepatic arterial pedicle [11]. FIG. 1 shows the anatomy of the liver.

Because liver metastases are likely blood-borne via the portal vein, for many years it was assumed that there was no advantage in wedge over segmental resection; the type of procedure chosen depended greatly on the location and number of metastases [12]. However, a better understanding of liver anatomy and improvements in radiologic imaging and anesthetic techniques has led to the widespread use of segmental liver resections. Segmental hepatectomy (i.e. segmentectomy) based on the anatomic descriptions of Couinaud is appealing for several reasons. First, blood flow to a segment is often stopped prior to transection of the liver. The resultant change of the liver color indicates the boundaries of the segment and ensures an adequate margin of normal tissue throughout the procedure. Second, segmentectomy may be used to preserve liver substance in cases that would otherwise require a resection of the entire right or left lobe. For this reason, segmental resection is suitable for the treatment of colorectal liver metastases. Removal of the tumor with an adequate margin is sufficient because intrahepatic metastases (i.e. tumor satellites) from an established colorectal liver metastasis are rare [13]. Two factors contribute to inadequate tumor clearance following non-anatomic wedge resections. First, traction on the specimen during division of the liver parenchyma can produce a fracture at the interface of the soft liver tissue and the hard colorectal metastasis. Second, lack of vascular control during a wedge resection can cause bleeding at the base of the wedge resection. This bleeding may obscure the transection and compromise the final margin [14].

When colorectal metastases are confined to the liver, five year survival rates after resection range from 30-35%. While morbidity is affected by blood loss, OR time, and residual liver volume, the prognosis is dependent on the presence or absence of adequate margins, regardless of the type of resection chosen. If positive resection margins are present following surgery (i.e., tumor cells are still present in the remaining liver after the tumor was excised), five year survival rates range from 0-18%, and few patients remain disease-free beyond 20 months. Five year survival rates in patients with negative margins of less than 1 cm range from 1826%, significantly worse than the 44-50% survival rate seen in patients with negative margins greater than 1 cm. In further comparing wedge vs. segmental resection in one study with over 260 patients, the rate of positive margins present following wedge removal was 8 times higher than with segmentectomy [14].

As more liver is removed in a multi-segment or lobectomy procedure, however, there are complications. Although liver resection has shown promising survival rates and a perioperative mortality rate of less than 5%, a significant increase in postoperative morbidity due to hepatic dysfunction and infection has been reported, even by specialized centers [15-17]. It was suspected that as more major liver resections were being conducted, removal of more significant amounts of liver tissue could cause complications. The paradigm that at least one third of healthy liver volume should be left to avoid hepatic failure following resection has been a standard for many years, but until recently, data did not exist to support this claim. In a study of over 100 patients that studied hepatic dysfunction and infection after major liver surgery [18], Schindl et al. used a regression analysis to demonstrate that dysfunction increases significantly when the relative residual liver volume (RLV) was below 26.6%. Body mass index (BMI) was also a highly significant factor; note that although prolonged operating time and blood loss were not as significant, they did improve the regression model fit. In the 103 patients reviewed for this study, 69% underwent either a standard right lobectomy (48) or an extended right lobectomy (23). On average, these patients had an RLV value of 33.3%, which is above but within one standard deviation of the 26.6% cutoff. The authors believe that calculating a specific % RLV before major liver surgery from a virtual resection on segmented CT scans provided useful information for planning hepatic surgery. They also note that it should not be a barrier to undertake major liver resection when the chance for cure outweighs the risks. Interestingly, most patients who developed severe postoperative hepatic dysfunction also had additional predictive factors, including significant blood loss and long operating time.

Based on this comprehensive study, it is evident that image-guided liver surgery is potentially beneficial in several ways. Most importantly, it would allow surgeons to perform more specific procedures that they currently only perform in a virtual manner. By interactively viewing the accurate location of vasculature and tissue surrounding the tumor as they operate, surgeons can more confidently perform segmental and wedge resections and avoid the removal of extraneous healthy liver volume. Segment-oriented anatomical resection will be more hemostatic as surgeons will be more specific in the control of blood vessels due to enhanced anatomical information. Finally, as surgeons become more efficient at using 3-D imaging interactively during surgery, operating time will potentially decrease. Through an efficacy clinical trial to be conducted by PTI, IGLS will potentially be shown to positively affect the ability to perform specific operations with optimized RLV, decreased blood loss, and decreased overall operating time. These factors impact hepatic dysfunction following major liver transection and can be improved by more specific surgery as provided using IGLS.

It is known that determination of an accurate image-to-physical space registration is a fundamental step in providing accurate guidance information to surgeons via image-guided surgery. Since the use of rigid, point-based landmarks is not feasible in image-guided liver surgery (IGLS) applications, surface-based techniques were proposed to determine the registration between the preoperative images and the intraoperative patient space. Specifically, the iterative closest point (ICP) algorithm, developed by Besl and McKay, has traditionally been used to determine the transformation between the image space surface of the liver, derived from preoperative image segmentations, and the intraoperative liver surface. Intraoperative data were initially acquired using an optically tracked probe while more recent efforts have utilized laser range scanner (LRS) technology to provide spatially dense, textured delineations. The current protocol for the performance of a surface-based image-to-physical space registration first involves the selection anatomical fiducial points in the preoperative images sets prior to surgery. The homologous physical space location of these anatomical fiducials is then digitized during the surgery such that a point-based initial alignment registration can be performed. The point-based registration serves to provide a reasonable initial pose for the ICP algorithm. Being that the surface alignment provided by the ICP algorithm is highly dependent on the initial pose of the surfaces, gross errors in the initial alignment provided by the point-based registration can result in erroneous surface alignments. A failed surface-based registration not only compromises the guidance information relayed to the surgeon but also impairs deformation correction efforts due to inaccurate surface displacement data that are used to drive mathematical models. In IGLS, the quality of the initial alignment registration can be compromised by the large fiducial localization errors (FLE) inherent in using anatomical landmarks that undergo non-rigid deformation relative to the preoperative images. Additionally, gravity and the effects of the liver mobilization and packing performed prior to open liver resections can lead to liver deformations that compromise the results of a rigid ICP surface registration. Clinical data shows a poor initial alignment registration, due to high FLE of the anatomical fiducials, and large liver deformations resulted in the convergence of the rigid ICP algorithm to a gross misalignment.

Therefore, a heretofore unaddressed need exists in the art to address the aforementioned deficiencies and inadequacies.

SUMMARY OF THE INVENTION

The present invention provides apparatus and methods of compensation for intra-operative organ shift of a living subject, being a human being or animal, which are cost-effective, clinically translatable, scalable to medical centers and facilities, and tractable. The present invention also provides apparatus and methods of surface registration (increasing the percentage of correct registrations) and allows registrations in situations where only a fraction of the surface may be seen.

In one aspect, the present invention relates to a method of compensation for intraoperative deformations of an organ of interest of a living subject. The organ of interest of the living subject can be a liver, heart, kidney, lung, stomach, brain, or soft tissues. In one embodiment, the method includes the steps of:

a. preoperatively acquiring an image of the organ of interest of the living subject;
b. segmenting the preoperatively acquired image;
c. tessellating the segmented image to obtain a three-dimensional (3D) surface of the organ of interest;
d. generating a tetrahedral volumetric mesh from the tessellated 3D surface of the organ of interest;
e. modeling deformations of the organ of interest from the generated tetrahedral volumetric mesh with a finite element model (FEM) having a set of mesh nodes;
f. intraoperatively acquiring range scan data of the organ of interest, wherein the range scan data is associated with the intraoperatively deformed surface of the organ of interest;
g. registering the intraoperatively acquired range scan data to the tessellated 3D surface of the organ of interest by weighting regions of the intraoperatively acquired range scan data that are minimally deformed, wherein closest point distances between mesh nodes of interest and the intraoperatively deformed surface are calculated;
h. constructing boundary conditions from a preoperatively surgical plan and the registered intraoperative range scan data, wherein the boundary conditions comprise initial deformations of the organ of interest associated with the set of mesh nodes;
i. obtaining model solutions of the FEM corresponding to the boundary conditions iteratively in an incremental fashion, wherein fractions of the closest point distances are used to prescribe a displacement boundary condition on the mesh nodes;
j. updating the locations of the mesh nodes by corresponding model solutions of the FEM, which triggers calculation of new registrations and boundary condition values; and
k. repeating steps (i) and (j) until the root mean square (RMS) closest point distances for all mesh nodes have reached a predetermined value.

The model solutions of the FEM are used to align the preoperatively acquired image to the intraoperatively acquired range scan data for compensating for deformations of the organ of interest of the living subject.

The step of intraoperatively acquiring range scan data of the organ of interest is performed by swabbing an optical stylus on the surface of the organ of interest or by scanning the surface of the organ of interest.

In one embodiment, the preoperatively acquired image of the organ of interest comprises a computer tomography (CT) image, a positron emission tomography (PET) image, a magnetic resonance (MR) image, or a functional magnetic resonance (fMR) image. The tessellated 3D surface of the organ of interest is represented as a set of polygons and serves as input for generating a tetrahedral volumetric mesh.

In another aspect, the present invention relates to a method of compensation for intraoperative deformations of an organ of interest of a living subject. In one embodiment, the method includes the steps of:

a. preoperatively acquiring an image of the organ of interest of the living subject;
b. intraoperatively acquiring an image of the organ of interest of the living subject;
c. generating a first geometric surface of the organ of interest from the intraoperatively acquired image of the organ of interest;
d. constructing an atlas, [A], of deformations of the organ of interest from the pre-operatively acquired image of the organ of interest, wherein the atlas [A] is in the form of an n×m matrix with n, m being positive integers;
e. generating a second geometric surface of the organ of interest from the constructed atlas [A] of deformations of the organ of interest;
f. aligning the second geometric surface of the organ of interest to the first geometric surface of the organ of interest to determine at least one difference between a point of the first geometric surface and a corresponding point of the second geometric surface of the organ of interest;
g. feeding back the at least one difference to step (e) to generate a new second geometric surface of the organ from the atlas [A] of organ deformations of the organ of interest;
h. iteratively repeating steps (e)-(g) for a predetermined number of iterations or until an error tolerance related to the at least one difference between a point of the first geometric surface and a corresponding point of the second geometric surface of the organ of the living subject is no greater than a predetermined threshold; and
i. compensating for the intraoperative organ deformation.

In one embodiment, the pre-operatively acquired organ images of the living subject comprise image data with respect to the organ surface geometry. The image data with respect to the organ surface geometry is obtained through the use of at least one of positron emission tomography device, electroencephalography device, computer tomography device, functional magnetic resonance imaging device, magnetic resonance imaging device, and ultrasound imaging device.

In one embodiment, the step of constructing the atlas [A] of deformations of the organ of interest comprises the steps of generating a geometric volume of the organ of interest from the preoperatively acquired image; modeling deformations of the organ of interest based on the geometric volume of the organ of interest with a computational model; obtaining m model solutions of the computational model corresponding to the geometric volume of the organ of interest, wherein each model solution, A, represents a solution of deformation for n variables and corresponding to a set of parameters; and generating the atlas [A] in the form of an n×m matrix with each model solution, A, which is in the form of a n×1 matrix, forming a column of the matrix.

The geometric volume of the organ of interest is generated through segmentation of the pre-operatively acquired image of the organ of interest, and represented by a tetrahedral mesh with n surface nodes.

In one embodiment, the model solutions are obtained by solving at least one partial differential equation modeled to represent the relationship between a deformation of the organ of interest and at least one force causing the deformation, and wherein the at least one partial differential equation is solved with boundary conditions corresponding to specific structures of the organ of interest, body force, material properties, vascularization, physiological changes related to tissue of the organ of the living subject, physical conditions or any combinations of them. The at least one partial differential equation is solved with the boundary conditions iteratively.

In one embodiment, the step of intra-operatively acquiring the image of the organ of the living subject is performed with an optical device that is capable of obtaining frequency, intensity and geometric data with respect to the surface of the organ of interest of the living subject simultaneously. The optical device is a laser range scanner, or an optical stylus. In another embodiment, the step of intra-operatively acquiring the image of the organ of interest of the living subject is performed with stereo pair technology.

In one embodiment, the step of aligning the second geometric surface of the organ of interest to the first geometric surface of the organ of interest of the living subject is performed with a point-based registration, or a weighted point-based registration, where the weighted point-based registration comprises the step of using a salient-feature weighted correspondence, and wherein when the organ is a liver, the salient-feature comprises a falciform ligament region.

In another embodiment, the step of aligning the second geometric surface of the organ of interest to the first geometric surface of the organ of interest of the living subject is performed with a registration that provides a surface-to-surface correspondence using at least one characteristic feature of the organ of interest of the living subject.

In yet another aspect, the present invention relates to a method of compensation for intraoperative deformations of an organ of interest of a living subject. In one embodiment, the method has the steps of generating a first geometric surface of the organ of interest of the living subject from an intraoperatively acquired image of the organ of interest of the living subject; constructing an atlas of deformations of the organ of interest of the living subject from a preoperatively acquired organ image; generating a second geometric surface of the organ of interest of the living subject from the atlas of deformations; aligning the second geometric surface of the organ of interest to the first geometric surface of the organ of interest of the living subject to determine at least one difference between a point of the first geometric surface and a corresponding point of the second geometric surface of the organ of the living subject, which is related to organ deformation; and compensating for the intra-operative organ deformation.

In one embodiment, the intraoperative deformations of the organ of interest are corresponding to distributed loading conditions that are associated with gravity, edema-induced swelling, mannitoi-induced shrinking, or any combination of them. In another embodiment, the intraoperative deformations of the organ of interest are corresponding to surface-based loading conditions that are associated with tissue retraction, tissue resection, or any combination of them.

In a further aspect, the present invention relates to a system of compensation for intraoperative deformations of an organ of interest of a living subject. The organ of interest of the living subject is a liver, heart, kidney, lung, stomach, brain, or soft tissues. In one embodiment, the system has a first imaging acquiring device for pre-operatively acquiring an image of the organ of interest of the living subject; a second imaging acquiring device for intra-operatively acquiring an image of an organ of interest of the living subject; and at least one computer coupled with the first image acquiring device and the second image acquiring device and adapted for performing the steps of:

i). generating a first geometric surface of the organ of interest from the intraoperatively acquired image of the organ of interest of the living subject;

ii). constructing an atlas of deformations of the organ of interest from the preoperatively acquired organ image;

iii). generating a second geometric surface of the organ of interest from the atlas of deformations;

iv). aligning the second geometric surface of the organ of interest to the first geometric surface of the organ of interest of the living subject to determine at least one difference between a point of the first geometric surface and a corresponding point of the second geometric surface of the organ of interest of the living subject, which is related to organ deformation; and v). compensating for the intraoperative organ deformation.

The system further has a display device coupled to the at least one computer for displaying the deformation of the organ of interest dynamically to facilitate a diagnostic or surgical procedure.

In one embodiment, the first imaging acquiring device comprises at least one of positron emission tomography device, electroencephalography device, computer tomography device, functional magnetic resonance imaging device, magnetic resonance imaging device, and ultrasound imaging device. The second imaging acquiring device comprises a laser range scanner that is capable of obtaining frequency, intensity and geometric data with respect to the cortical surface of the living subject simultaneously. The second imaging acquiring device can also be an ultrasound imaging device, or an optical stylus.

In yet a further aspect, the present invention relates to a method of surface registration in image guided surgery. In one embodiment, the method includes the steps of:

a. preoperatively acquiring an image of an organ of interest of a living subject;

b. generating a first surface of the organ of interest of the living subject from the preoperatively acquired image;

c. designating a set of target points, $T=\{t_n\}$, $n=1, 2, 3, \ldots, N_T$, from the first surface of the organ of interest, wherein the set of target points T contains one or more patch points corresponding to homologous anatomical features of the first surface of the organ of interest, and wherein each of the set of target points $t_m$ is indexed with a binary index, $p^T_m$, such that when $p^T_m=0$, the target point $t_m$ is a non-patch point, and when $p^T_m=1$, the target point $t_m$ is a patch point;

d. intraoperatively acquiring an image of the organ of interest of the living subject;

e. generating a second surface of the organ of interest of the living subject from the intraoperatively acquired image;

f. designating a set of source points, $S=\{s_m\}$, $m=1, 2, 3, \ldots, N_S$, from the second surface of the organ of interest, wherein the set of source points S contain one or more patch points corresponding to homologous anatomical features of the second surface of the organ of interest, which is related to the corresponding homologous anatomical features of the first surface of the organ of interest, and wherein each of the set of source points $s_m$ is indexed with a binary index, $p^S_m$, such that when $p^S_m=0$, the source point $s_m$ is a non-patch point, and when $p^S_m=1$, the source point $s_m$ is a patch point;

g. determining a point correspondence between the set of source points S and the set of target points T, whereby a closest point operator, $C=\{C_m\}$ is determined;

h. biasing the point correspondence between the one or more source patch points and the one or more target patch points by a weighting factor, $w_{PC}$, so as to bias the closest point operator $C_m$, via the following relationship:

$$d_{m,n} = \begin{cases} w_{PC}\|s_m - t_n\| & \text{if } p_m^S = p_n^T = 1 \\ \|s_m - t_n\| & \text{otherwise} \end{cases}$$

wherein $0 < w_{PC} \ll 1$, $d_{m,n}$ is Euclidian distance between a source point $s_m$ and a target point $t_n$;

i. aligning the second surface of the organ of interest to the first surface of the organ of interest using a weighted point based registration (PBR) between the set of source points S and the set of target points T by finding a rigid-body transformation ($\Omega$) between the set of source points and the set of target points that minimizes an objective function of:

$$f(\Omega) = \sqrt{\sum_{m=1}^{N_M} w_m \|C_m(s_m, T) - \Omega(s_m)\|^2},$$

wherein $\{w_m\}$ is a set of weights letting $w_m = 1$ for $p^S_m = 0$ and $w_m = W_{PBR}$ for $P^S_m = 1$, and wherein $W_{PBR}$ is a function of iteration, i, in the form of:

$$W_{PBR}(i) = W_{PBR,base} + [W_{PBR,max} - W_{PBR,base}]\exp[-\alpha(i-1)],$$

wherein i=1, 2, 3, ... N, N being the number of iteration, $W_{PBR,max}$ is a maximum patch weight factor and corresponds a patch weight at a first iteration, $W_{PBR,base}$ is a baseline patch weight factor, with $1 \leq W_{PBR,base} \leq W_{PBR,max}$, and $\alpha$ is a relaxation constant with $0 \leq \alpha \leq 1$, wherein the aligned second surface of the organ of interest up; and j. repeating steps (f)-(i) using the aligned second surface of the organ of interest until the root mean square (RMS) closest point distances between the source and target points have reached a predetermined value.

In one embodiment, the pre-operatively acquired image of the organ of interest of the living subject comprises image data with respect to the surface geometry of the organ of interest, where the image data with respect to the surface geometry of the organ of interest is obtained through the use of at least one of positron emission tomography device, electroencephalography device, computer tomography device, functional magnetic resonance imaging device, magnetic resonance imaging device, and ultrasound imaging device.

In one embodiment, the step of generating a first surface of the organ of interest of the living subject comprises the step of extracting details of the first surface using at least one of the following features: user identification of surface features or visible structures; surface curvature; surface shape; surface orientation within the living subject; distribution of surface normal orientation; and potential for deformation of the anatomic structure.

In one embodiment, the step of intra-operatively acquiring images of the organ of interest of the living subject is performed with one of the following methods: swabbing the surface of the anatomic structure with a tracked instrument; laser range scanning of the anatomic structure for surface determination; intra-operative ultrasound scanning of the anatomic structure; imaging of the anatomic structure using a tracked laparoscope or endoscope; and surface extraction of the anatomic structure from a binocular scene such as provided by a binocular laparoscope or endoscope.

In one aspect, the present invention relates to a method of surface registration in image guided surgery. In one embodiment, the method includes the steps of:

a. pre-operatively acquiring an image of an anatomic structure of a living subject;

b. generating a first surface of the anatomic structure of the living subject from the preoperatively acquired image of the anatomic structure of the living subject;

c. constructing one or more first patches corresponding to the first surface of the anatomic structure, wherein each first patch contains a surface subset of physical space data related to a salient anatomical feature of the first surface of the anatomic structure;

d. intra-operatively acquiring an image of the anatomic structure of the living subject;

e. generating a second surface of the anatomic structure of the living subject from the intraoperatively acquired image of the anatomic structure of the living subject;

f. constructing one or more second patches corresponding to the second surface of the anatomic structure, wherein each second patch contains a surface subset of physical space data from the second surface related to a corresponding salient anatomical feature of the first surface of the anatomic structure;

g. aligning the one or more second patches to the corresponding one or more first patches, wherein each second patch is dynamically biased to a corresponding first patch; and h. completing a registration of the second surface to the first surface with physical space data not contained in the first and second patches to indicate surgical position in both image space and physical space.

The anatomic structure of the living subject comprises a liver, heart, kidney, lung, stomach, or brain, where when the anatomic structure comprises a liver, the salient-feature comprises a falciform ligament region.

In one embodiment, the pre-operatively acquired images of the anatomic structure comprise image data with respect to the surface geometry of the anatomic structure, where the image data with respect to the surface geometry of the anatomic structure is obtained through the use of at least one of positron emission tomography device, electroencephalography device, computer tomography device, functional magnetic resonance imaging device, magnetic resonance imaging device, and ultrasound imaging device.

In one embodiment, the step of generating a first surface of the anatomic structure of the living subject comprises the step of extracting details of the first surface using at least one of the following features: user identification of surface features or visible structures; surface curvature; surface shape; surface orientation within the living subject; distribution of surface normal orientation; and potential for deformation of the anatomic structure.

The step of intra-operatively acquiring images of the anatomic structure of the living subject is performed with one of the following methods: swabbing the surface of the anatomic structure with a tracked instrument; laser range scanning of the anatomic structure for surface determination; intra-operative ultrasound scanning of the anatomic structure; imaging of the anatomic structure using a tracked laparoscope or endoscope; and surface extraction of the anatomic structure from a binocular scene such as provided by a binocular laparoscope or endoscope.

The step of aligning the one or more second patches to the corresponding one or more first patches comprises the step of giving more weight to the patches than to the rest of the surfaces.

The step of completing a registration of the second surface to the first surface with physical space data not contained in the first and second patches comprises the step of increasing weight to the rest of the surfaces when final adjustments in the registration are made with all available surface information.

The step of completing a registration of the second surface to the first surface with physical space data not contained in the first and second patches is performed with a point-based registration, where the point-based registration comprises a weighted point-based registration, and wherein the weighted point-based registration comprises the step of using a salient-feature weighted correspondence.

In another aspect, the present invention relates to a method of surface registration in image guided surgery. In one embodiment, the method has the steps of generating a first surface of an anatomic structure of a living subject from pre-operatively acquired images of the anatomic structure of the living subject; generating a second surface of the anatomic structure of the living subject from intra-operatively acquired images of the anatomic structure of the living subject; constructing one or more second patches corresponding to the second surface of the anatomic structure, wherein each second patch contains a surface subset of physical space data from the second surface related to a corresponding salient anatomical feature of the first surface of the anatomic structure; aligning the one or more second patches to the corresponding one or more first patches, wherein each second patch is dynamically biased to a corresponding first patch; and completing a registration of the second surface to the first surface with physical space data not contained in the first and second patches to indicate surgical position in both image space and physical space.

In one embodiment, the step of completing a registration of the second surface to the first surface with physical space data not contained in the first and second patches is performed with a point-based registration, where the point-based registration comprises a weighted point-based registration, and wherein the weighted point-based registration comprises the step of using a salient-feature weighted correspondence.

In yet another aspect, the present invention relates to a system of surface registration in image guided surgery. In one embodiment, the system has a first imaging acquiring device for pre-operatively acquiring images of an anatomic structure of a living subject; a second imaging acquiring device for intra-operatively acquiring images of at least part of the anatomic structure of a living subject; and at least one computer coupled with the first image acquiring device and the second image acquiring device and adapted for performing the steps of:

i). generating a first surface of the anatomic structure of the living subject from the pre-operatively acquired images of the anatomic structure of the living subject;

ii). constructing one or more first patches corresponding to the first surface of the anatomic structure, wherein each first patch contains a surface subset of physical space data related to a salient anatomical feature of the first surface of the anatomic structure;

iii). generating a second surface of the anatomic structure of the living subject from the intra-operatively acquired images of the anatomic structure of the living subject;

iv). constructing one or more second patches corresponding to the second surface of the anatomic structure, wherein each second patch contains a surface subset of physical space data from the second surface related to a corresponding salient anatomical feature of the first surface of the anatomic structure;

v). aligning the one or more second patches to the corresponding one or more first patches, wherein each second patch is dynamically biased to a corresponding first patch; and vi). completing a registration of the second surface to the first surface with physical space data not contained in the first and second patches to indicate surgical position in both image space and physical space.

In one embodiment, the system further comprising a display device coupled to the at least one computer for displaying the registration dynamically to facilitate a diagnostic or surgical procedure.

In one embodiment, the first imaging acquiring device comprises at least one of positron emission tomography device, electroencephalography device, computer tomography device, functional magnetic resonance imaging device, magnetic resonance imaging device, and ultrasound imaging device. In one embodiment, the second imaging acquiring device includes a laser range scanner that is capable of obtaining frequency, intensity and geometric data with respect to the cortical surface of the living subject simultaneously. In another embodiment, the second imaging acquiring device includes an ultrasound imaging device. In an alternative embodiment, the second imaging acquiring device comprises a tracked instrument, an optical stylus, a tracked laparoscope or endoscope, or a binocular laparoscope or endoscope.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIG. 8 shows (a) an application of closest point distance as Cartesian displacement vector, and (b) incremental application with normal displacement but free lateral shift along the surface.

FIG. 15 shows corresponding CT slices from (a) nondeformed and (b) deformed image. The plastic object placed below the liver produces the deformation observed in FIG. 6a. The height of the object is approximately 38 mm.

FIG. 21 shows EM tumor errors with respect to the initial alignment. The solution scale used for these experiments is 0.2. The five alignment methods are listed in Table 2. The dotted lines indicate the tumors experiencing the most deformation.

FIG. 23 shows tumor errors from FEM model while varying implementation of boundary conditions and the construction method of the preconditioner and stiffness matrix. The initial rigid alignment used here was based on ICP of the range scan surface.

FIG. 24 shows a quantitative comparison of closest point boundary conditions using (a) the normal-tangential local coordinate frame and (b) the Cartesian coordinate frame. The cartesian boundary conditions result in a clear boundary between the closest point nodes and nodes that prescribe a different type of boundary condition. This boundary is highlighted by the red arrows in (b).

Figure 31:
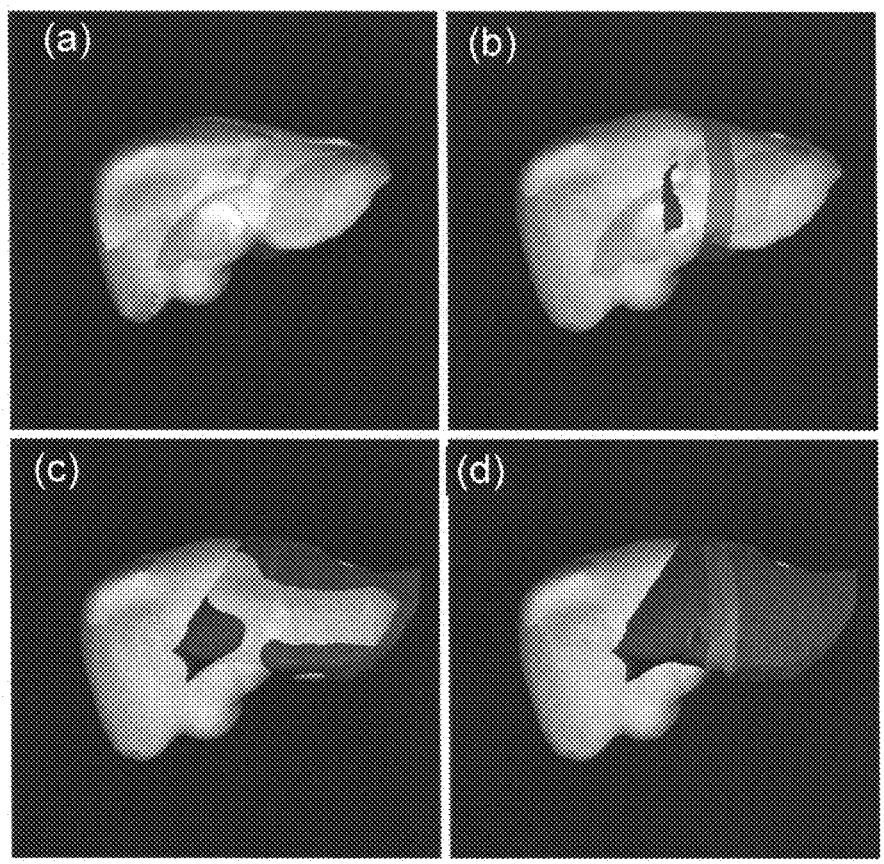

FIG. 31 shows clinical results for Patient 1 showing visualizations of the ICP registration (a), (b) and the patch ICP registration (c), (d). The LRS and ICP patches are highlighted for the ICP and patch ICP registrations in (b) and (d), respectively. Note that the ICP alignment causes an extremely erroneous registration. The LRS scan of the anterior liver surface becomes registered to the posterior of the liver. The patch ICP registration provides a much more reasonable alignment. Note that for this data set the CT image and LRS surfaces contained 48,843 points and 16,293 points, respectively. The CT image and LRS falciform regions consisted of 1,397 and 728 points, respectively.

Figure 32:
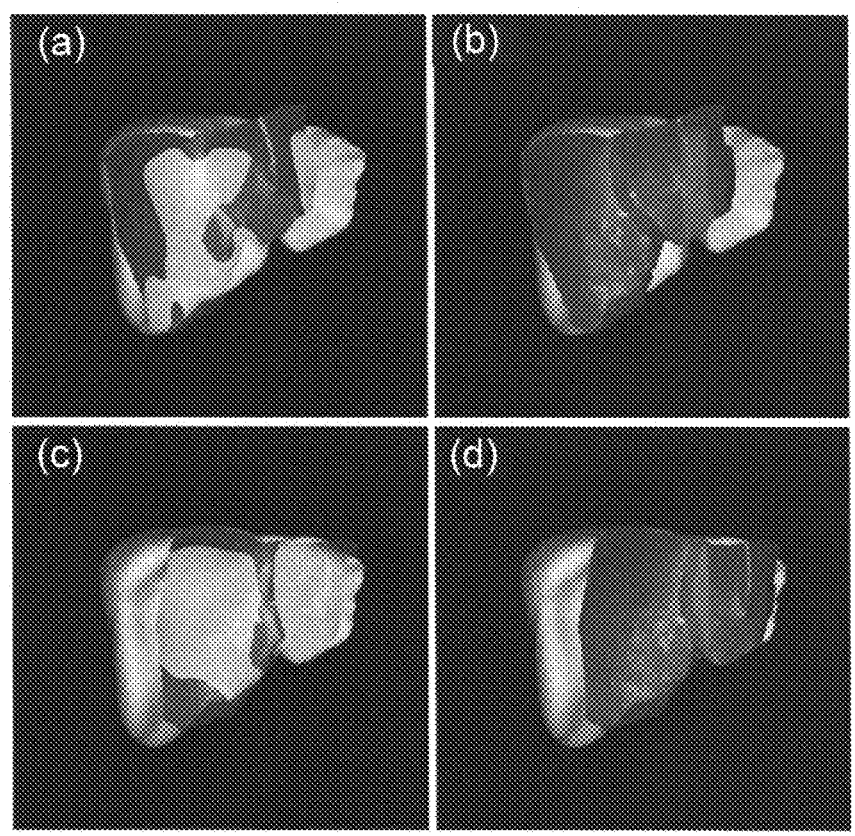

FIG. 32 shows clinical results for Patient 2 showing visualizations of the ICP registration (a), (b) and the patch ICP registration (c), (d). The LRS and ICP patches are highlighted for the ICP and patch ICP registrations in (b) and (d), respectively. The ICP registration shows an apparent misalignment which is corrected via the proposed method. Note that for this data set the CT image and LRS surfaces contained 53,459 points and 16,675 points, respectively. The CT image and LRS falciform regions consisted of 1,632 and 1,507 points, respectively.

Figure 29:
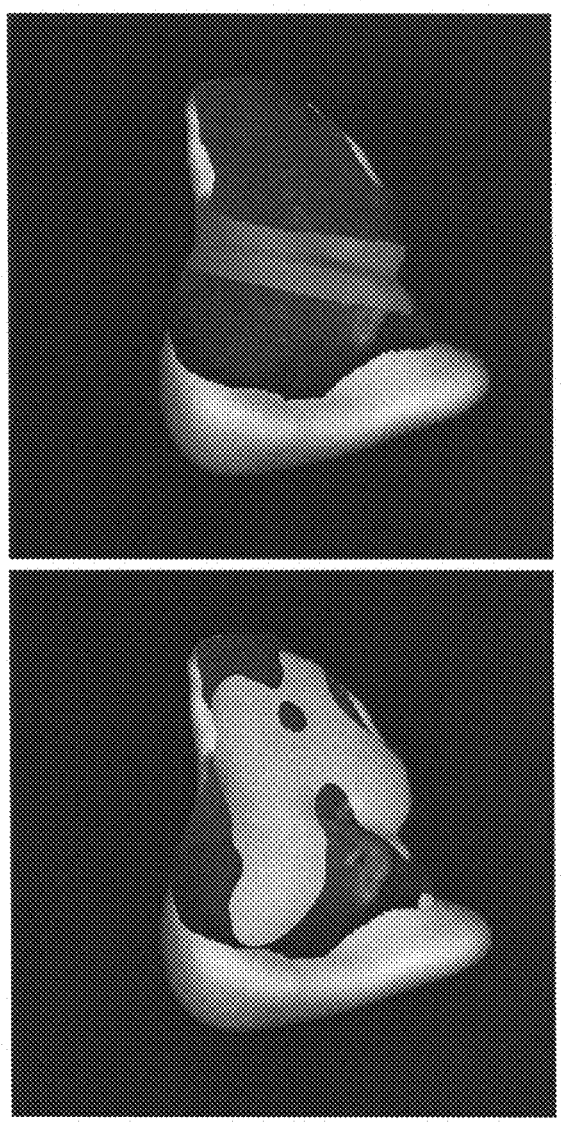
FIG. 29 shows traditional ICP registration results (a) and overlaid image and falciform patch regions (b) for the clinical data used in the robustness trials (Patient 3). Note the large contrast in the accuracy of the alignment in this case than that shown in FIG. 1. The RMS residual for this registration was 3.43 mm. Note that for this data set the CT image and LRS surfaces contained 57,873 points and 19,863 points, respectively. The CT image and LRS falciform regions consisted of 3,148 and 594 points, respectively.
Figure 33:
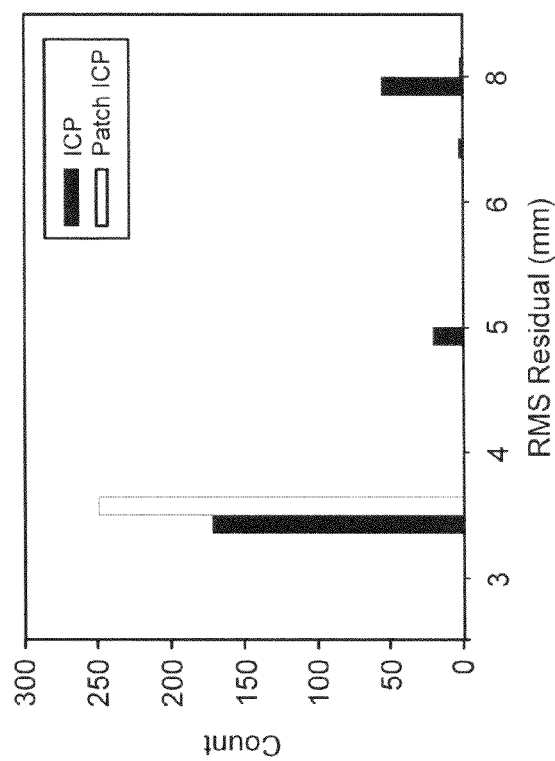

FIG. 33 shows a histogram representation of the RMS residual data obtained from robustness test performed on clinical data (Patient 3). The "gold standard" ICP registration is shown in FIG. 29 and this registration yielded an RMS residual of 3.43 mm. Note that only one patch ICP trial yielded a significantly greater RMS residual than the "gold standard".

FIG. 34 shows a comparison of an original slice (a), a manual segmentation (b) and a level set segmentation (c) of a liver of a patient.

Figure 35:
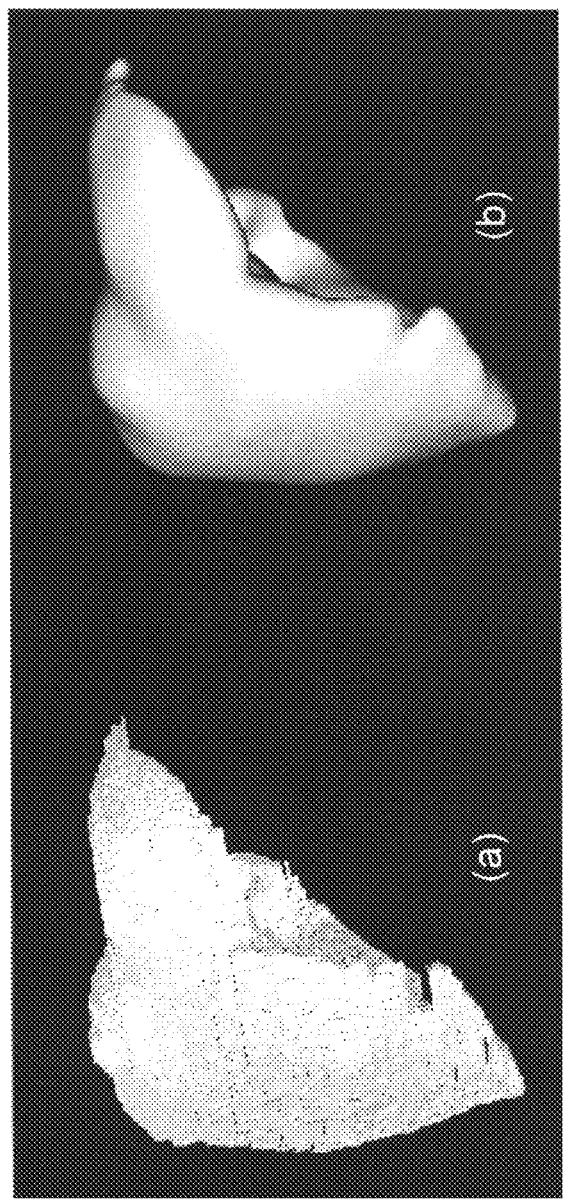

FIG. 35 shows a surface model generation from the segmented contours. The initial surface mesh (a) is generated using the marching cubes method, and refined (b) with a surface fitting technique that employs Radial Basis Functions [81], providing a smoother surface with less vertices, potentially increasing the speed and accuracy of the registration.

Figure 36:
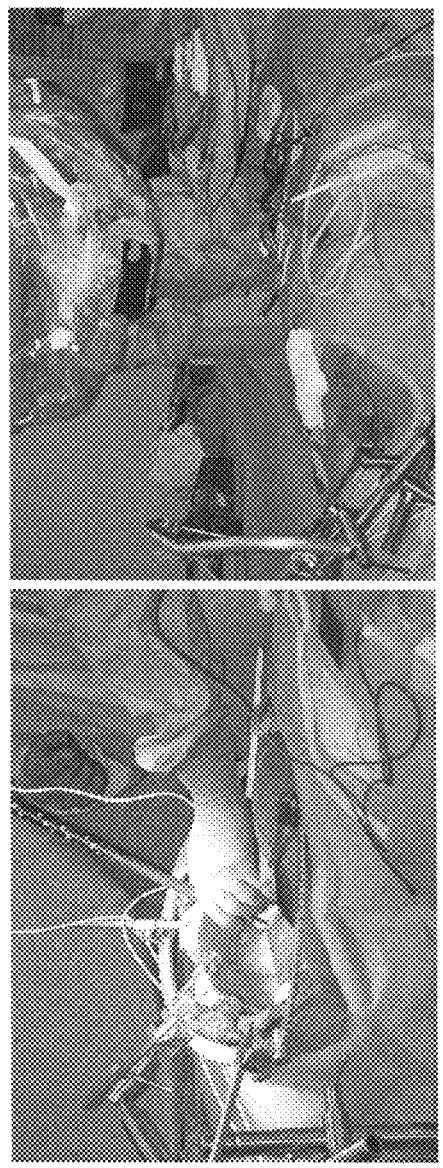

FIG. 36 shows a surface data acquisition in the OR. In the left image, the surgeon is digitizing points on the liver surface with the optically tracked probe. The right image shows the range scanner in position to acquire surface data of the liver intraoperatively.

Figure 37:
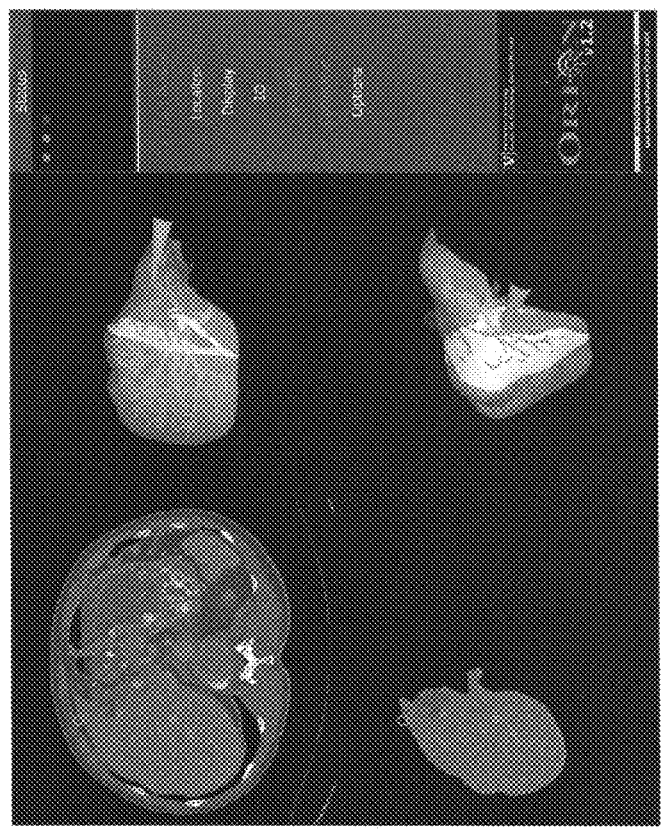

FIG. 37 shows a screen shot of range scan module in ORION surgical navigation software. From the top-left panel clockwise: the native tomogram, two different perspectives of the three-dimensional liver and the vasculature as segmented by MeVis, and a tomographic slice of the segmented liver.

FIG. 38 shows a time plot of respiratory data. The data is aligned according to the axes provided by the primary component analysis. The origin is the mean of the original respiration data.

Figure 39:
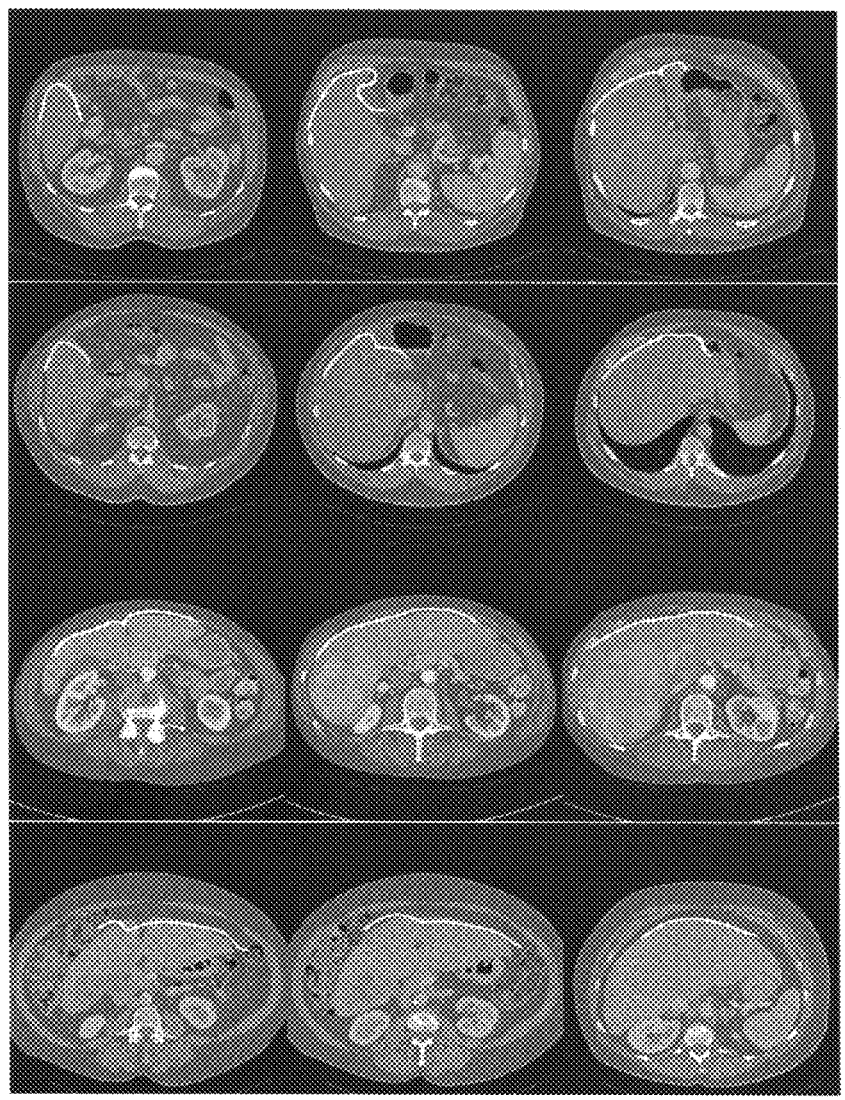

FIG. 39 shows ICP registration results. For each case, the registered range scan data is overlaid on top of three tomographic slices from the volume.

Figure 40:
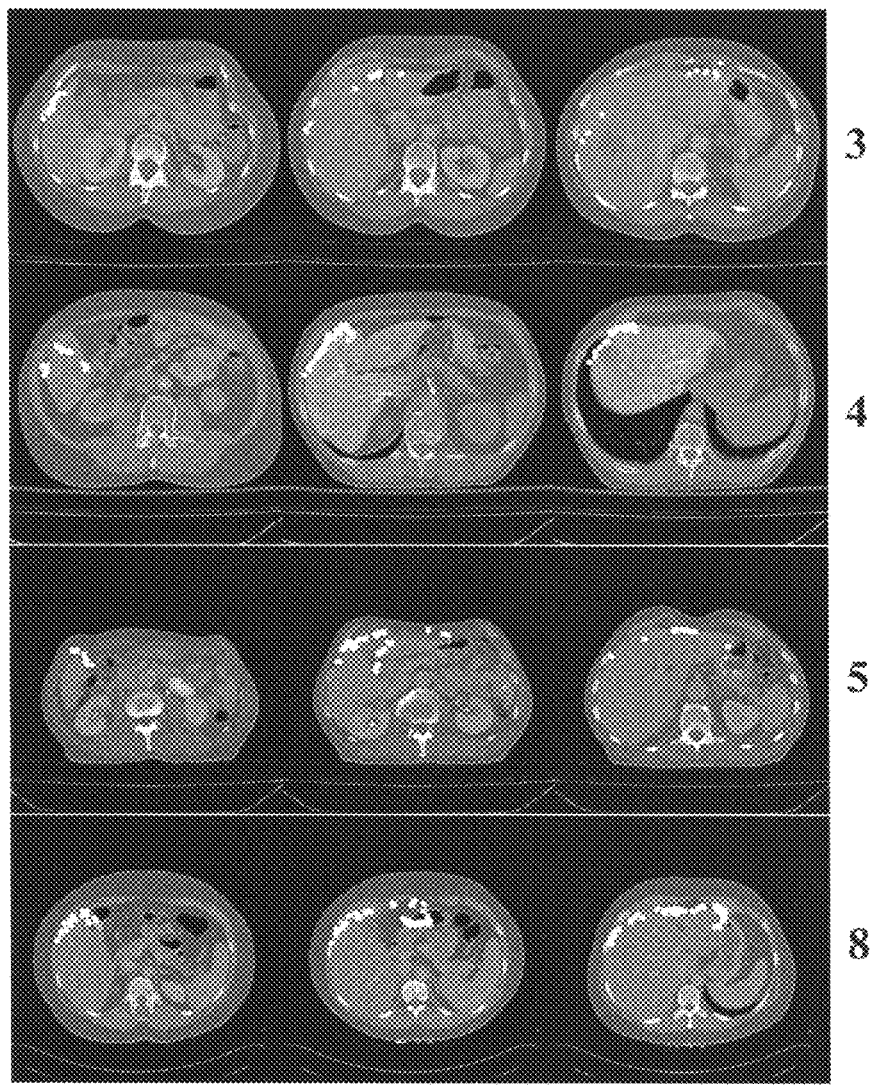

FIG. 40 shows ICP registration results. For each case, the registered probe data is overlaid on top of three tomographic slices from the volume.

Figure 41:
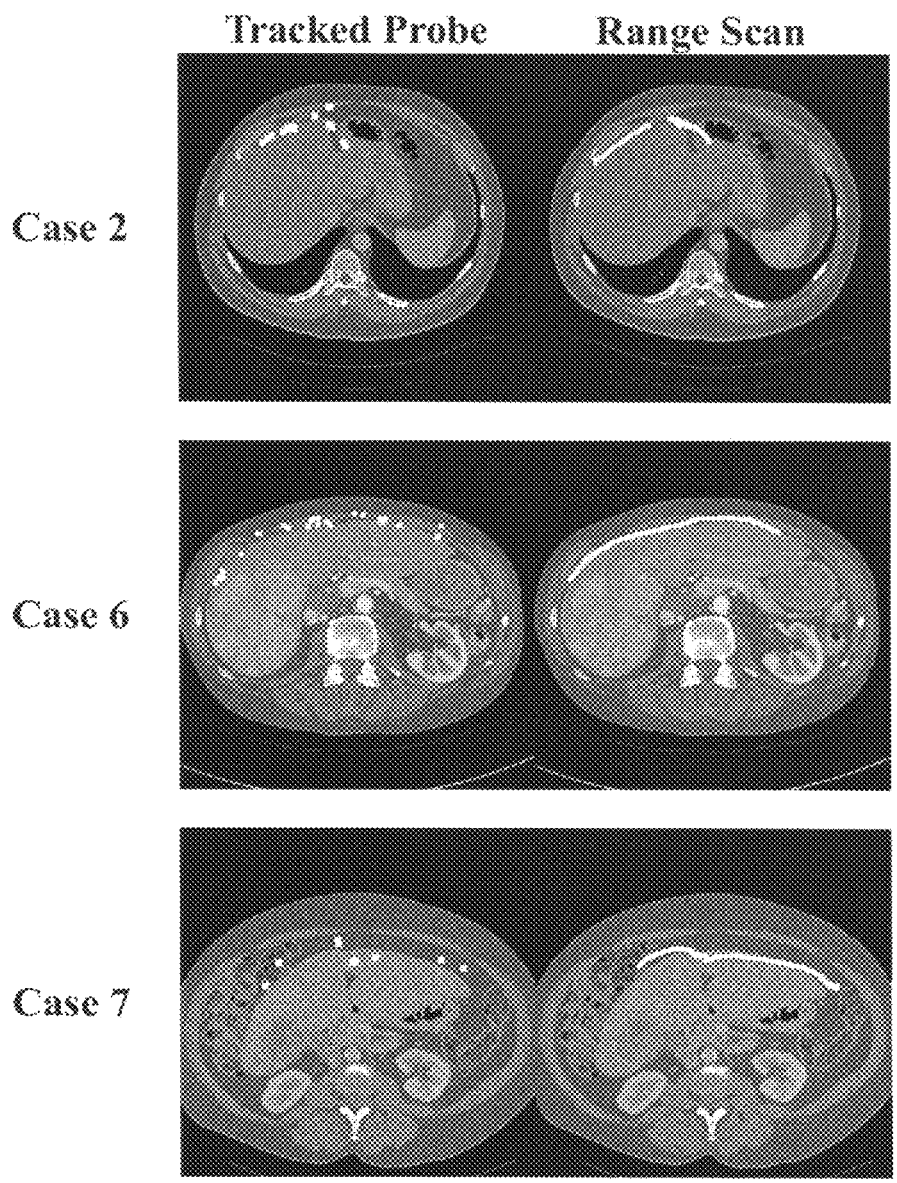

FIG. 41 shows a comparison of surface registrations using tracked probe (left column) and range scan (right column). Both data sets are overlaid on the identical slice from the image volume.

Figure 42:
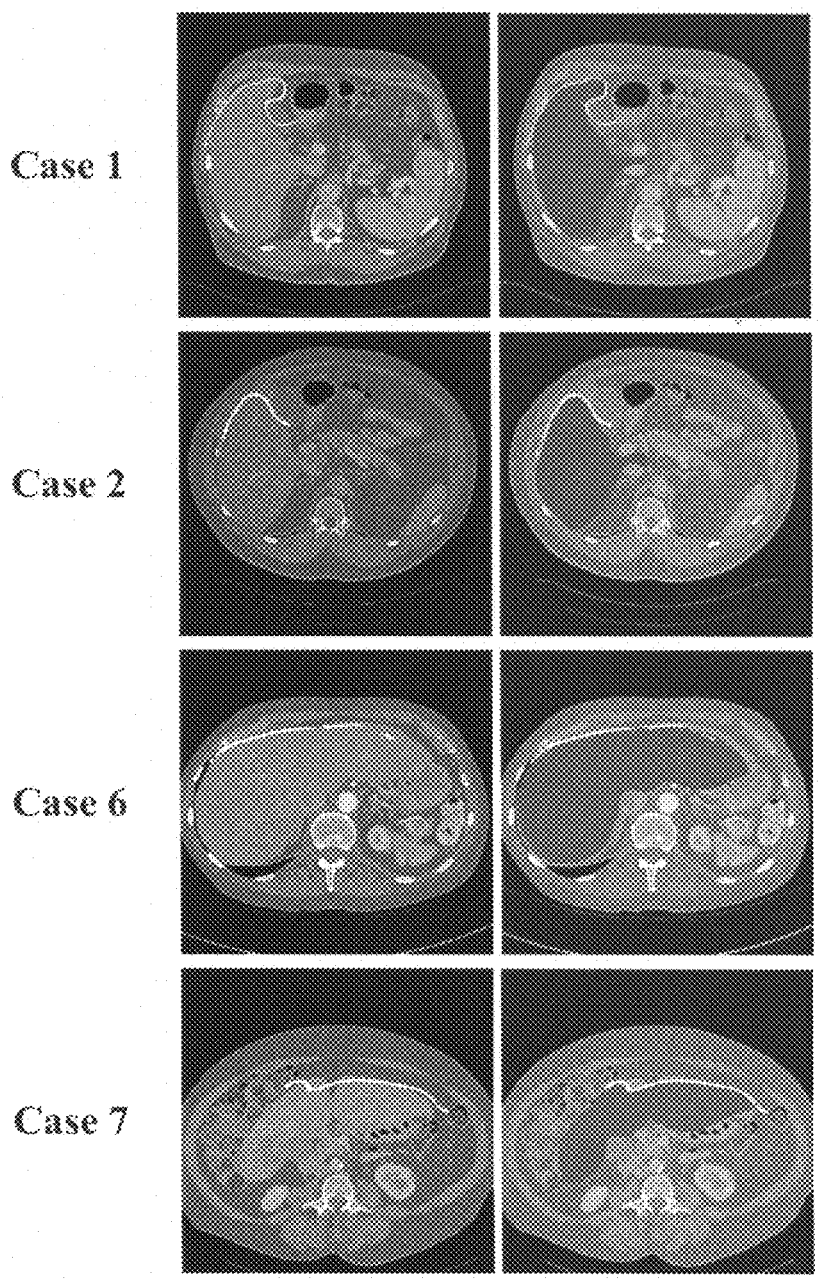

FIG. 42 shows (left column) original rigid registration of range scan data overlaid on to mograms, (right column) the deformed liver volume from the finite element model is overlaid in red. In the areas where the point cloud was used for the boundary conditions, there is improved agreement between the range scan surface and the deformed image surface.

Figure 43:
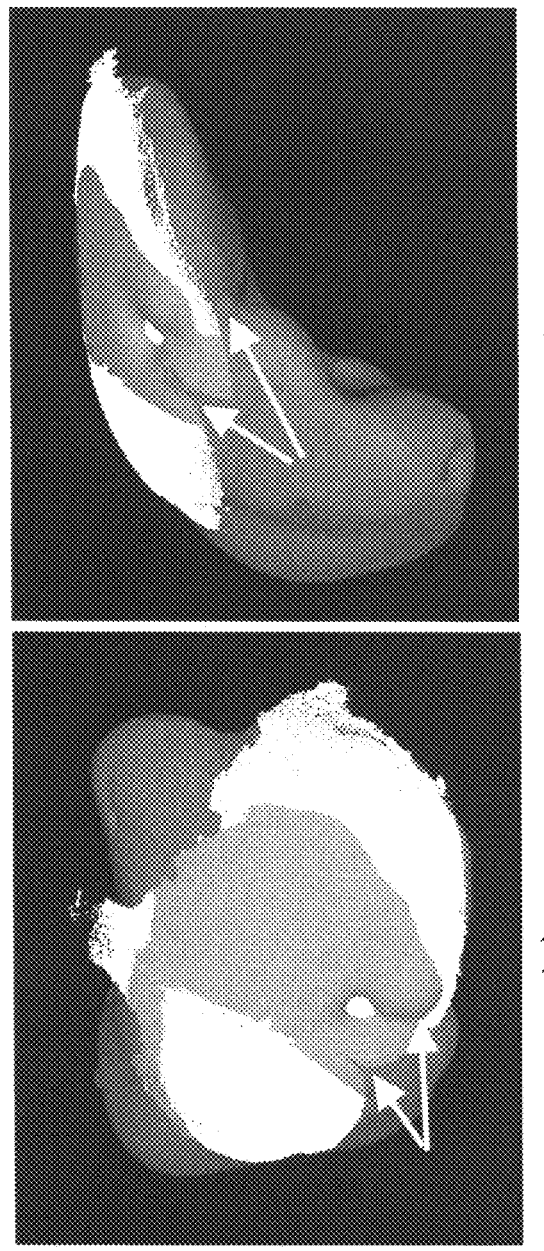

FIG. 43 shows the relatively planar range scan data results in misalignments during the surface-based registration, in case 7, and the qualitatively identified landmark, where the falciform ligament resided before surgery is rotated clockwise, as indicated by the white arrows.

DETAILED DESCRIPTION OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which has no influence on the scope of the invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner in describing various embodiments of the invention and how to practice the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "living subject" refers to a human being such as a patient, or an animal such as a lab testing pig.

As used herein, "registration", "map" and "alignment" are synonyms in the specification, unless the context therein clearly indicates otherwise.

As used herein, "organ shift" and "organ deformation" are synonyms in the specification, unless the context therein clearly indicates otherwise.

Overview of the Invention

The description will be made as to the embodiments of the present invention in conjunction with the accompanying drawings. In accordance with the purposes of this invention, as embodied and broadly described herein, this invention, in one aspect, relates to a method of compensation for intraoperative deformations of an organ of interest of a living subject, where the organ of interest of the living subject is a liver, heart, kidney, lung, stomach, brain, or soft tissues.

In one embodiment, the method includes the following steps: At step (a), an image of the organ of interest of the living subject is preoperatively acquired. The pre-operatively acquired organ image of the living subject comprises image data with respect to the organ surface geometry. The image data with respect to the organ surface geometry is obtained through the use of at least one of positron emission tomography device, electroencephalography device, computer tomography device, functional magnetic resonance imaging device, magnetic resonance imaging device, and ultrasound imaging device.

At step (b), an image (or intraoperative shape) of the organ of interest of the living subject is intraoperatively acquired by, for example, an optical device capable of obtaining frequency, intensity and geometric data with respect to the surface of the organ of interest of the living subject simultaneously. The optical device is a laser range scanner, or an optical stylus. The intraoperative shape of the organ of interest of the living subject may also be acquired by stereo pair technology. It would be also advantageous if the geometric surface is also referenced to the field of view or is textured by a digital image of the field of view.

At step (c), a first geometric surface of the organ of interest is generated from the intraoperatively acquired image of the organ of interest in step (b). At step (d), an atlas, [A], of deformations of the organ of interest is constructed from the pre-operatively acquired image of the organ of interest. The atlas [A] is in the form of an n×m matrix with n, m being positive integers. Step (c) is performed by generating a geometric volume of the organ of interest from the preoperatively acquired image in step (a); modeling deformations of the organ of interest based on the geometric volume of the organ of interest with a computational model; obtaining m model solutions of the computational model corresponding to the geometric volume of the organ of interest, where each model solution, A, represents a solution of deformation for n variables and corresponding to a set of parameters; and generating the atlas [A] in the form of an n×m matrix with each model solution, A, which is in the form of a n×1 matrix, forming a column of the matrix.

The geometric volume of the organ of interest is generated through segmentation of the pre-operatively acquired image of the organ of interest, and represented by a tetrahedral mesh with n surface nodes.

The model solutions are obtained by solving at least one partial differential equation modeled to represent the relationship between a deformation of the organ of interest and at least one force causing the deformation. The at least one partial differential equation is solved with boundary conditions corresponding to specific structures of the organ of interest, body force, material properties, vascularization, physiological changes related to tissue of the organ of the living subject, physical conditions or any combinations of them. The at least one partial differential equation is solved with the boundary conditions iteratively.

At step (e), a second geometric surface of the organ of interest is generated from the constructed atlas [A] of deformations of the organ of interest.

At step (f), the second geometric surface of the organ of interest is aligned to the first geometric surface of the organ of interest to determine at least one difference between a point of the first geometric surface and a corresponding point of the second geometric surface of the organ of interest. The alignment of the second geometric surface of the organ of interest to the first geometric surface of the organ of interest of the living subject is performed with a point-based registration, or a weighted point-based registration, where the weighted point-based registration comprises the step of using a salient-feature weighted correspondence, and wherein when the organ is a liver, the salient-feature comprises a falciform ligament region. The alignment of the second geometric surface of the organ of interest to the first geometric surface of the organ of interest of the living subject may also be performed with a registration that provides a surface-to-surface correspondence using at least one characteristic feature of the organ of interest of the living subject.

At step (g), the at least one difference is fed back to step (e) to generate a new second geometric surface of the organ from the atlas [A] of organ deformations of the organ of interest. At step (h), steps (e)-(g) are iteratively repeated for a predetermined number of iterations or until an error tolerance related to the at least one difference between a point of the first geometric surface and a corresponding point of the second geometric surface of the organ of the living subject is no greater than a predetermined threshold. Then, the intraoperative organ deformation is compensated. Note, here, as elsewhere in the specification, while the method is given in a number of steps in an order, it is understood that these steps do not have to be performed in that given order.

In another aspect, the present invention relates to a method of surface registration in image guided surgery. In one embodiment, the method includes the following steps:

At first, a surface of an anatomic structure (or an organ of interest) of the living subject is extracted from a tomographic scan, for example, CT, MRI, PET or SPECT images preoperatively acquired by any one of a number of conventional image processing algorithms. The pre-operatively acquired image of the anatomic structure comprises image data with respect to the surface geometry of the anatomic structure.

Then, details of the surface of the anatomic structure are extracted by any one of the following features: (a) user identification of surface features or visible structures, (b) surface curvature, (c) surface shape, (d) surface orientation within the patient, (e) distribution of surface normal orientation, and (f) potential for deformation. Areas of these details are collected and grouped into surface subsets called "patches". In other words, one or more first patches corresponding to the first surface of the anatomic structure are constructed, where each first patch contains a surface subset of physical space data related to a salient anatomical feature of the first surface of the anatomic structure.

An intraoperative determination of an internal anatomic structure is obtained by one of the following methods: (i) swabbing the surface with a tracked instrument, (ii) laser range scanning for surface determination, (iii) intraoperative ultrasound, (iv) imaging using a tracked laparoscope or endoscope, (v) surface extraction from a binocular scene such as provided by a binocular laparoscope or endoscope.

Once the intraoperative surface has been obtained, details corresponding to the surface parameters extracted from the preoperative images are obtained. These may include: user identification of surface features or visible structures, surface curvature, surface shape, surface orientation within the patient, distribution of surface normal orientation, and/or potential for deformation. The procedure constructs one or more second patches corresponding to the second surface of the anatomic structure, wherein each second patch contains a surface subset of physical space data from the second surface related to a corresponding salient anatomical feature of the first surface of the anatomic structure.

The one or more second patches are aligned to the corresponding one or more first patches, where each second patch is dynamically biased to a corresponding first patch. The alignment of the one or more second patches to the corresponding one or more first patches comprises the step of giving more weight to the patches than to the rest of the surfaces. Then, a registration of the second surface to the first surface with physical space data not contained in the first and second patches to indicate surgical position in both image space and physical space is performed, by increasing weight to the rest of the surfaces when final adjustments in the registration are made with all available surface information, using a point-based registration, preferably, a weighted point-based registration. The weighted point-based registration comprises the step of using a salient-feature weighted correspondence.

There is no expectation that extraction of these parameters will lead to exactly homologous patches in both spaces. However, the alignment of the patches will be initially weighted more heavily than that of the rest of the surface in the cost function of the alignment algorithm. As the alignment progresses, using techniques such as iterative closest point (ICP), chamfer matching or other techniques, the weight of the general surface alignment rises relative to the patch weight until final adjustments in the registration use all available surface information.

One advantage of the patch registration over standard surface ICP is that it captures additional information beyond the surface shape description and uses that to improve the registration. This means that patch techniques should work when only part of the organ or structure of interest is visible. This may prove critically important as one moves to minimally invasive techniques.

Because surface-based registrations are search processes, it is customary to provide an initial alignment to reduce the space that has to be searched. The second advantage of the patch registration is that the early high weighting of the patches can provide the initial alignment, thus removing a first step.

Biological surfaces tend to be smooth and rotationally symmetric about at least one axis. The third advantage of patch registration is that because of the weight applied to a patch, the patch counts more than a similar zone and thus tends to "anchor" the registration where without the patch it might find a solution with similar metrics but incorrect alignment.

Yet another aspect of the present invention relates to a system of surface registration in image guided surgery. In one embodiment, the system has a first imaging acquiring device for pre-operatively acquiring images of an anatomic structure of a living subject; a second imaging acquiring device for intra-operatively acquiring images of at least part of the anatomic structure of a living subject; and at least one computer coupled with the first image acquiring device and the second image acquiring device and adapted for performing the steps of:

i). generating a first surface of the anatomic structure of the living subject from the pre-operatively acquired images of the anatomic structure of the living subject;

ii). constructing one or more first patches corresponding to the first surface of the anatomic structure, wherein each first patch contains a surface subset of physical space data related to a salient anatomical feature of the first surface of the anatomic structure;

iii). generating a second surface of the anatomic structure of the living subject from the intra-operatively acquired images of the anatomic structure of the living subject;

iv). constructing one or more second patches corresponding to the second surface of the anatomic structure, wherein each second patch contains a surface subset of physical space data from the second surface related to a corresponding salient anatomical feature of the first surface of the anatomic structure;

v). aligning the one or more second patches to the corresponding one or more first patches, wherein each second patch is dynamically biased to a corresponding first patch; and vi). completing a registration of the second surface to the first surface with physical space data not contained in the first and second patches to indicate surgical position in both image space and physical space.

In one embodiment, the system further comprising a display device coupled to the at least one computer for displaying the registration dynamically to facilitate a diagnostic or surgical procedure.

In one embodiment, the first imaging acquiring device has at least one of positron emission tomography device, electroencephalography device, computer tomography device, functional magnetic resonance imaging device, magnetic resonance imaging device, and ultrasound imaging device. In one embodiment, the second imaging acquiring device includes a laser range scanner that is capable of obtaining frequency, intensity and geometric data with respect to the cortical surface of the living subject simultaneously. In another embodiment, the second imaging acquiring device includes an ultrasound imaging device. In an alternative embodiment, the second imaging acquiring device comprises a tracked instrument, an optical stylus, a tracked laparoscope or endoscope, or a binocular laparoscope or endoscope.

These and other aspects of the present invention are more specifically described below.

IMPLEMENTATIONS AND EXAMPLES OF THE INVENTION

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Compensation for Intraoperative Organ Shift

A. Image-Guided Liver Surgery System: The current image-guided liver surgery (IGLS) system is developed through collaborative efforts between researchers at Vanderbilt University, Washington University in St. Louis, and Pathfinder Therapeutics Inc. (PTI), and has been used to collect data in more than 15 clinical cases. This working prototype has been in development for over eight years. Preoperative CT and MR images are acquired from the liver of a patient one to two weeks before the procedure. The liver of the patient is segmented from these preoperatively acquired image volumes. This segmentation can be performed by manually outlining the contour of the liver surface. However, the manual procedure is often very slow and tedious and may require hours to complete. An alternative and more expedient semi-automatic method was developed by Dr. Benoit Dawant at Vanderbilt University which is based on the level-set technique [30, 31]. This method takes 5-15 minutes to run, and then up to 15 minutes of user interaction after the segmentation. From the segmented images, a 3D surface is tessellated using the Marching Cubes Method [32]. The tessellated 3D surface includes a mesh of connected triangles and is used for the surface registration. These methods are currently integrated into the current system and are used when making data available to the applicants.

Intra-operative surface data of the exposed liver of the patient is obtained with a laser range scanner (LRS). Laser range scanning uses the principle of triangulation to determine 3D points in space. A laser light is emitted from the LRS and strikes the surface of the liver. The reflected light is received by a CCD camera. Based on the reflected light pattern and the known trigonometric relationship between the laser emitter and the camera, the 3D location is computed. According to this system, a line of laser light sweeps across the surface of interest, as shown in FIG. 2a, for acquiring a dense point cloud (shown in FIG. 2b) to represent the surface of interest. In addition, a digital image of the liver is captured of the operative field and mapped to the point cloud thus generating a textured point cloud, as shown in FIG. 2c. For OR use, the laser range scanner is optically tracked and brought into the operative field when needed for acquiring a scan.

Figure 3:
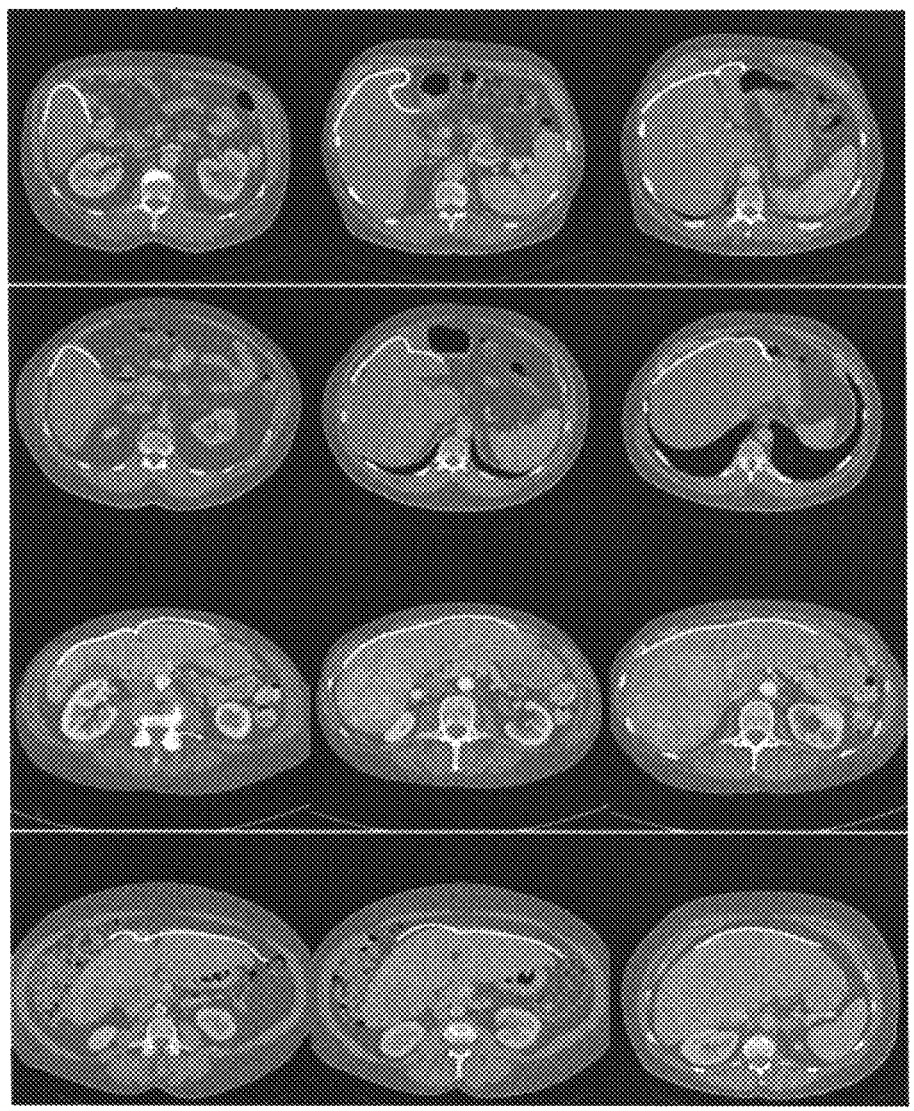
FIG. 3 shows physical-to-image registration results for four surgical cases using the LRS.

The range scan data is then registered with the preoperative surface using the iterative closest point (ICP) method, modified to use k-d trees for quicker closest point searches [33-36]. A point-based registration based on rough anatomic points serves as an input for the ICP. This initial registration restricts the search range of the ICP solution, thus improving time-to-solution and reducing the chance of falling into local minima. Retrospective registration results from four of the clinical cases are shown in FIG. 3, where three tomographic slices from the preoperative data are laid out in each row, and the registered range scan data is overlaid in white. Under careful inspection, the presence of deformation can be observed in these preliminary results.

Figure 4:
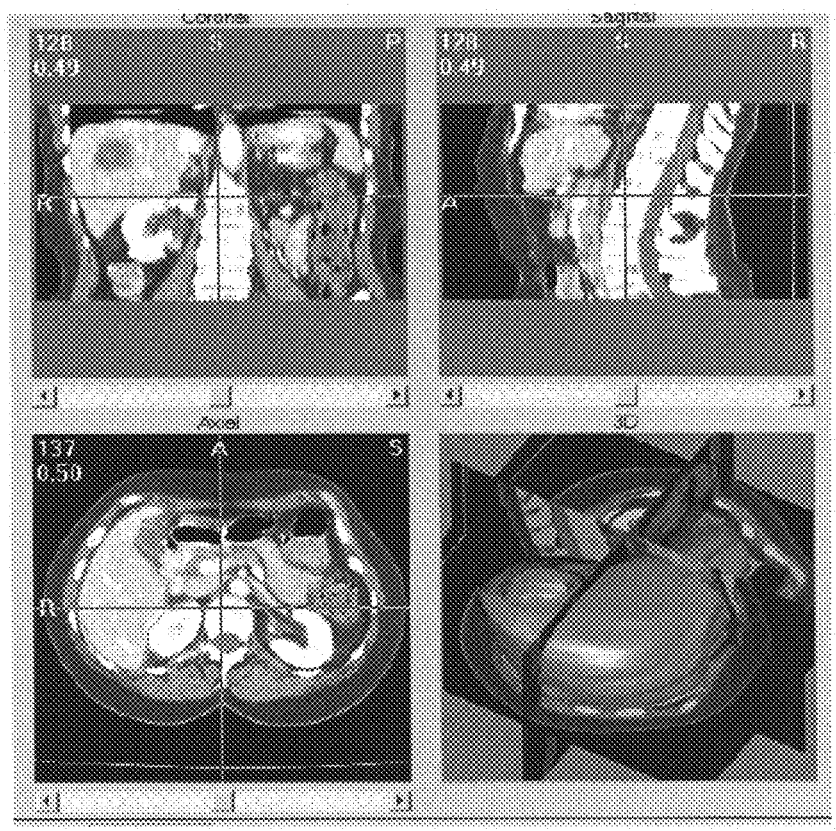
FIG. 4 shows a snapshot of a graphical user interface to facilitate the segmentation of the liver from tomographic images.

B. Segmentation of Liver Images for Model-Building and Determining Residual Liver Volume: In one embodiment, an FEM of the segmented liver is generated. Non-rigid organ-based registration provides more specific therapy for liver tumors over rigid based techniques by determining the amount of tissue removed during the surgery through a pre/post segmented liver volume comparison. This is then compared to what is predicted by the intra-operative surgical plan as initially digitized during the case. A critical component in this analysis is the accurate segmentation of the liver from the pre and post-operative CT and MR images. In one embodiment, the current method is using an innovative segmentation technique that has been evaluated in clinical practice and was developed by Dr. Benoit Dawant and researchers at Vanderbilt University. This level set-based method uses a new speed function that reduces leakage problems that are known to affect level set based methods [40], which has been evaluated at the Catholic University of Louvain in Belgium. The accuracy and repeatability of the method is compared with those of manual segmentation for determining liver volume in living liver transplant donors from MR images. For 18 living donors, two observers each performed two semi-automatic and two manual segmentations. Each measurement was timed and the average number of slice/volume is approximately 20. Actual graft weight was measured during surgery. The times to perform manual and automatic segmentation were compared. Accuracy and repeatability were evaluated with the Bland-Altam method. The key findings of this study were that (1) mean interaction time was reduced from 25 minutes with manual segmentation to 5 minutes with Dawant's method; (2) differences between the actual volume and the estimated volume ranged from −223 to +123 mL for manual segmentation and from −124 to +86 mL with the method; (3) automatic segmentation improved weight estimation in 15 out of 18 cases; and (4) inter and intra-observer repeatability (reliability) was improved using the semi-automatic method. The method developed is not fully automatic as it requires placing initial seeds within the structures to be segmented. In difficult cases, i.e., when boundaries between the liver and adjacent structures, heart, and intestine, are ill-defined, editing the contours according to the algorithm is also required, where placement of the seeds and contour editing is included in the total interaction time. To facilitate user interaction, a graphical user interface is developed to be shown in FIG. 4. This interface permits the placement of seed points, editing of contours, and visualization of tomographic volumes in the coronal, transverse, and sagittal directions. 3D segmented surfaces can be rendered and superimposed on the tomographic volumes. While the clinical validation study was conducted on MR images, which has been extended to CT images [30] and is also extendable to other types of images. Although a clinical study comparable to the one performed to test the algorithm on MR images has not yet been conducted on CT images, the preliminary results indicate a very good agreement between the method and manual delineation. In an exemplary embodiment, 6 CT volumes with an average number of slices equal to 196 (slice thickness ranging from 1 mm to 2 mm) were selected and the liver contours were delineated manually and with the method. Semiautomatic and manual contours were compared using a similarity index commonly used to compare segmentations defined as:

$$S = \frac{2N(C_1 \cap C_2)}{N(C_1) \cup N(C_2)} \quad (1)$$

in which N is the number of voxels within a contour and C1 and C2 are the manual and the semi-automatic contours respectively. Values of S above 0.8 indicate a very good agreement between delineations. The mean S value for the six volumes was 0.94 (min=0.92, max=0.95). It is expected that the method is successful and more useful within the CT context. Indeed, because of the large number of slices in CT volumes, segmenting the liver by hand in this modality is a daunting task. The average time required to segment 20 MR slices was 25 minutes. Extrapolating this number to 200 slices in CT (~4 hours) becomes quite alarming. Interaction time for the semiautomatic segmentation method does not grow linearly with the number of slices and is orders of magnitude faster than the manual.

C. Non-rigid Organ-based Registration: One object of the invention is to determine the extent of improvement by deformation correction both in the quantitative targets and in registration robustness. This can be achieved by the deformation compensation computational node according to the invention. It should be noted that the data necessary for the computational node is not unusual and should be available in most surgical guidance systems. At most, an added cost to other surgical systems would be the addition of a commercial laser range scanner which is quite reasonable when compared to the cost of an overall system.

The challenge for IGLS is more difficult than that of its neurosurgical counterpart. Undoubtedly, soft-tissue deformation is present but the nature of loading, the information available, and the tolerable margins for error are quite different. As opposed to neurosurgery, exploratory liver surgery does not have the confines of the cranium. In addition, surgical presentation of the organ often requires separation from the surrounding ligamenture and a presentation that differs considerably from its anatomical orientation within the body during preoperative scanning. While in neurosurgery data can be taken immediately post-durotomy, which allows for minimal differences between preoperative and intraoperative initialization, this is not the case for the liver whereby deformations induced by organ presentation are already in place when intraoperative data can be taken. This dramatic difference in organ shape is a specific challenge for image-guided liver surgery. Fortunately, the tolerance for localization is not quite as constrained due to the regenerative nature of the liver.

Figure 1:
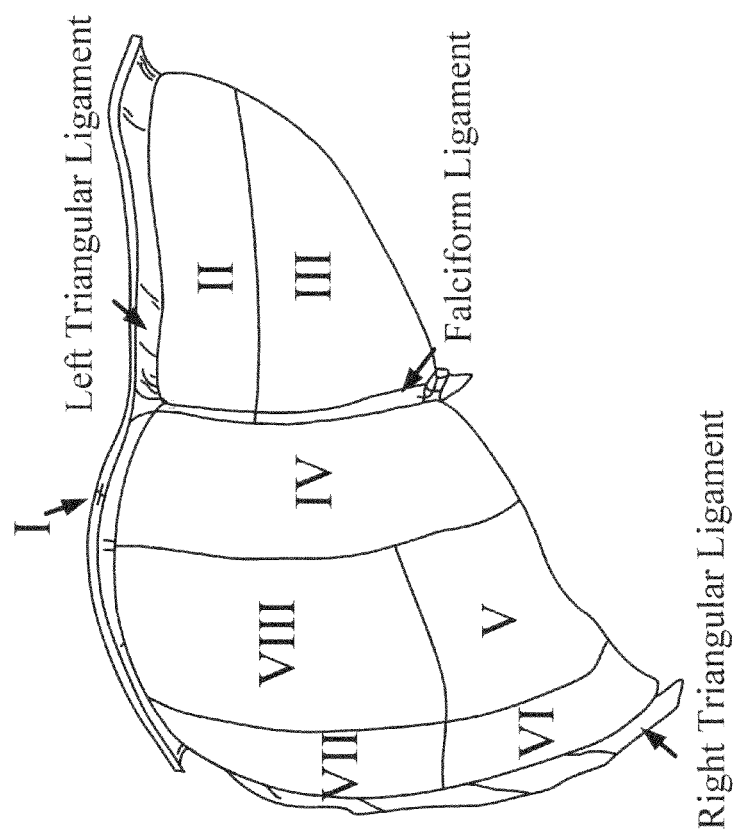
FIG. 1 shows anatomy of a liver of a living subject, with eight Couinaud segments and key ligaments labeled, where segment I is located posterior to the liver.
Figure 2:
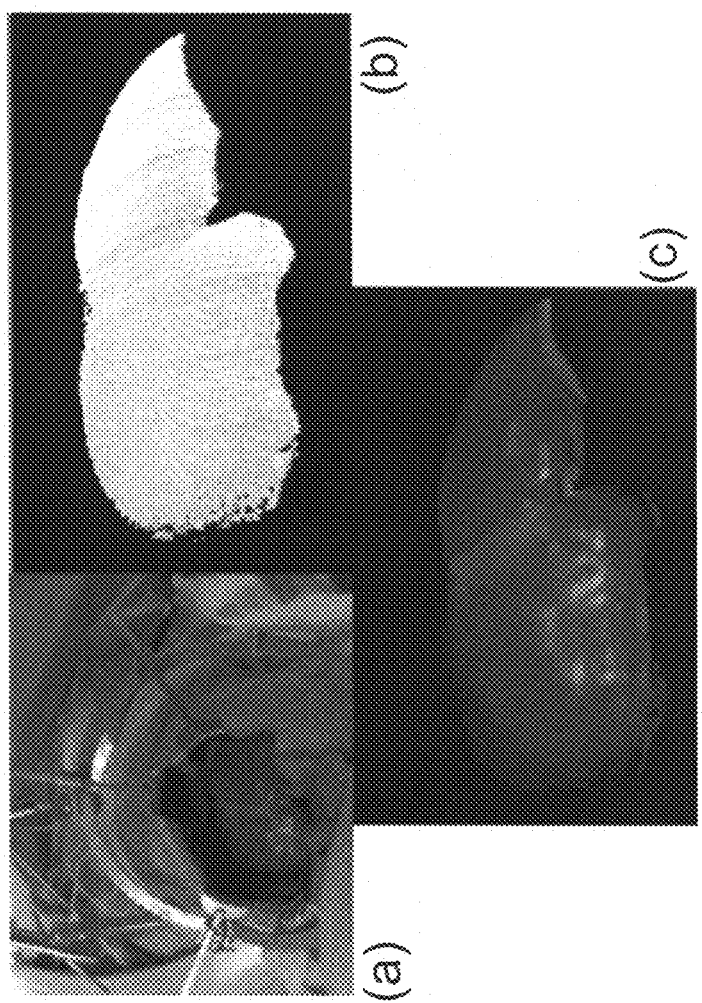
FIG. 2 shows (a) a digital photograph taken of the OR scene from the view of the range scanner; (b) range scanner setup in the OR; and (c) laser range scanner output showing a textured point cloud from the liver surface.
Figure 5:
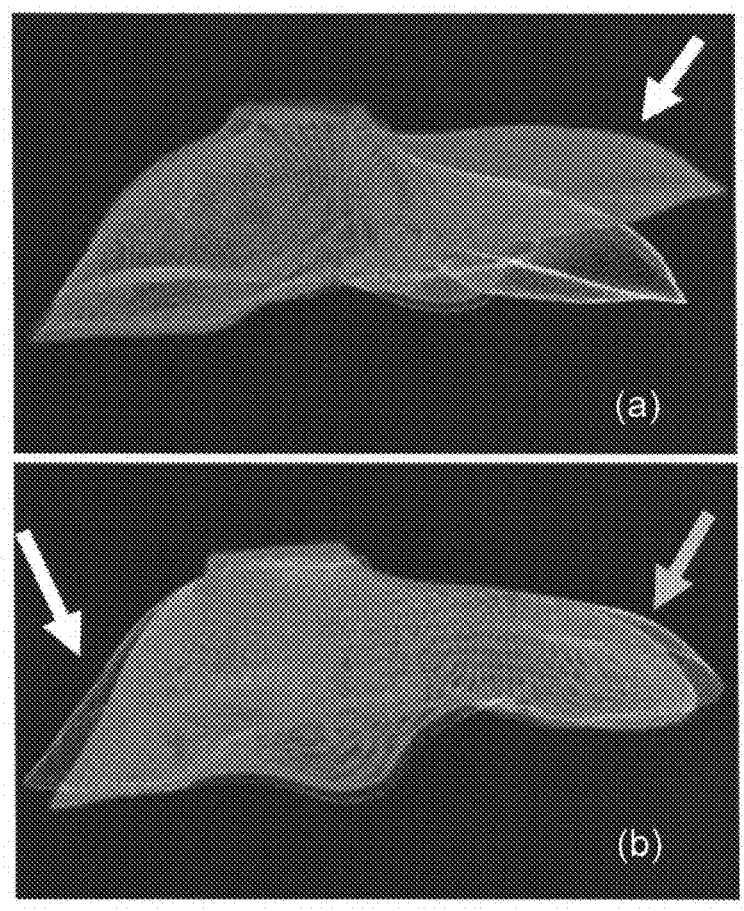
FIG. 5 shows (a) a liver phantom deformed by an anterior translation of the medial lobe, and (b) an iterative closest point registration between 2 surfaces (surfaces derived from taken by CT).
Figure 6:
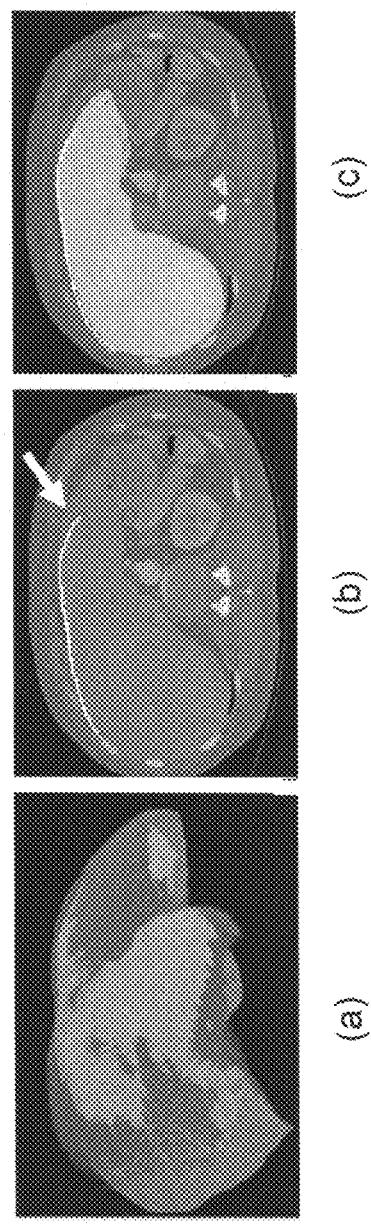
FIG. 6 shows (a) surface overlay of registered LRS point cloud and segmented preoperative CT surface (grey), (b) preoperative CT slice with contour overlay of registered LRS point cloud (arrow indicates approximate 1 cm difference between surfaces), and (c) overlay of deformed liver onto combined preoperative-LRS data tomogram show in FIG. 7b.
Figure 7:
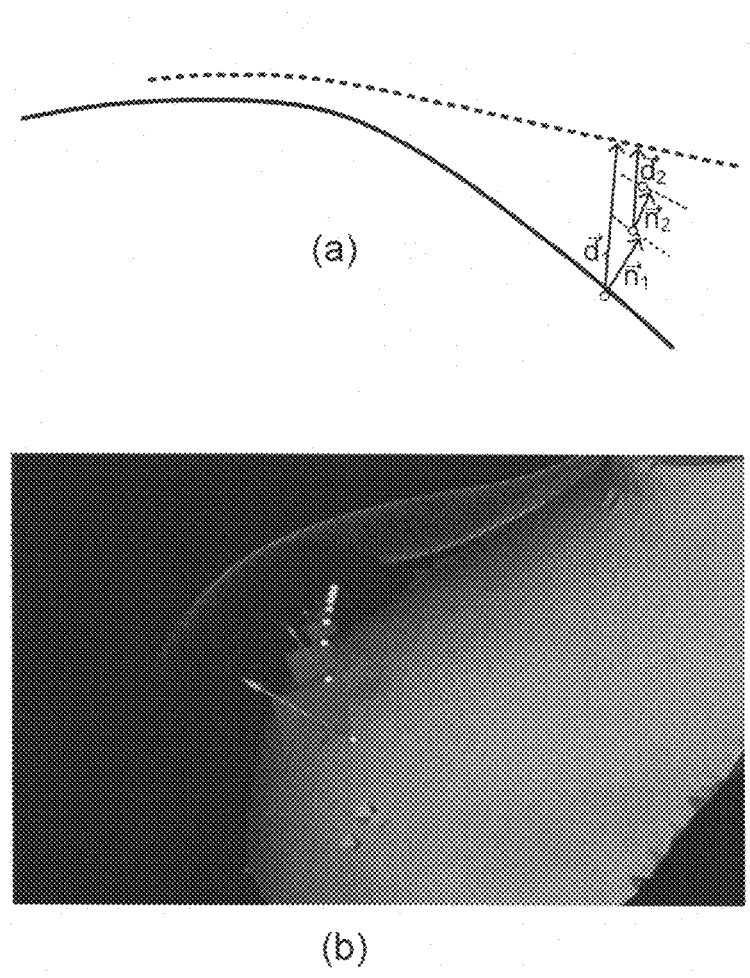
FIG. 7 shows an incremental strategy, (a) a portion of the closest point distance on a boundary is prescribed in a normal-to-the-boundary direction while allowing point to have lateral freedom along surface, and (b) visualized in three-dimensions.

FIG. 5 is an example of the challenges associated with deformations during organ presentation. FIG. 5a is a liver phantom with a possible deformation associated with organ presentation, and FIG. 5b shows the results of a rigid surface registration between the deformed and undeformed surfaces using the ICP method [41]. What is interesting about this result is that a standard surface registration method introduces error in areas that are minimally deforming while reducing errors in the deforming region (white arrow shows error introduction while gray shows error reduction). In the clinical example [39], as shown in FIG. 2, an equivalent registration is performed and the result is shown in FIG. 6a, where the LRS partial surface is aligned atop the respective patient's CT liver surface following ICP registration. The discrepancy in the registration is due to deformation and is designated by the white arrow in FIG. 6b. According to embodiments of the present invention, the inventors implemented a very basic approach [39] using the closest point correspondence after surface registration to provide a boundary condition mapping from one partial surface to the other and then allow the finite element model to generate remaining deformations, as shown in FIG. 6c. It can be seen from FIG. 6c how the deformed liver does match visually better the LRS contour which represents the intraoperative state. While the initial results in FIG. 6c are satisfying, more experience in the OR began to shape the challenges that needed to be addressed if the approach was to be more general and robust. It was evident that the initial alignment was very important. It has been experimented with a deformation identifying rigid registration (DIRR) which was based on phantom work [38], as described in Example 2 below. The DIRR is designed to generate an initial registration that was representative of FIG. 6a as opposed to FIG. 6b with the goal of allowing the FEM model to enforce deformation only on those surfaces experiencing it [38]. The hypothesis was that starting the non-rigid registration process from an initial condition that preferentially aligned minimally deforming regions was better than using one that minimized the error over the entire surface. In one embodiment, a novel cost function for the DIRR was developed in the form of:

$$f(S) = \sum_{i=1}^{N_S} \exp(-d_{S,i}^2/(2\tau^2)) \quad (2)$$

where for each point 'i' in the $N_s$ points of intraoperative data, a signed distance, $d_{s,i}$ to the non-deformed surface is calculated. The term $\tau$ is based on the standard deviation of a Gaussian function and is similar to the fuzzy correspondence work by Chui and Rangarajan [42]. Once this registration had been established, a series of incremental deformations are applied to the finite element model to align the preoperative and intraoperative state. FIG. 7 illustrates the incremental framework which was specifically designed to better account for geometric nonlinearities. Additionally, a linear elastic finite element model using a specially formulated normal-tangential boundary condition framework was utilized which allowed for displacements to be imposed that were normal to the organ surface but also allowed for lateral (i.e. tangential) degrees of freedom. This allowed for a more natural deformation to be applied to the organ. For example, in FIG. 8, a clear discrepancy can be seen where different boundary conditions are applied, i.e., vector displacement and stress free. In FIG. 8b, no distinction is shown due to the nature of the incremental solution and boundary condition formulation thus producing a more natural organ deformation.

Figure 9:
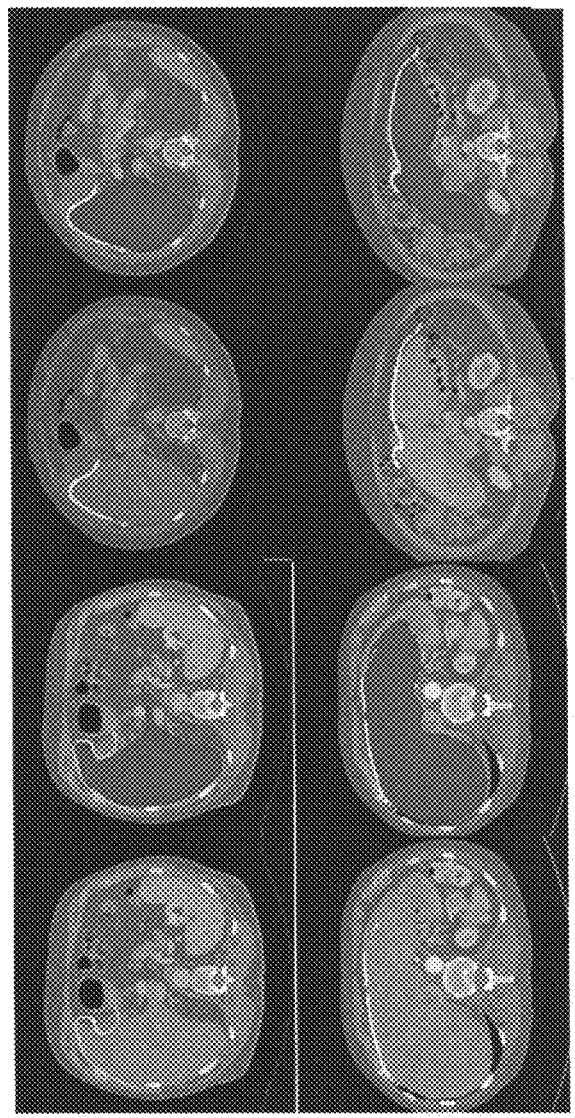
FIG. 9 shows results of model-updating approach for 4 clinical cases with: (red) deformed image volume, (CT) preoperative scan, and (white contour), intraoperatively acquired LRS scan.

This approach was tested in a set of phantom experiments, which some of the data is shown in FIG. 5, whereby an initial pre-deformation CT image volume was acquired and 2 realistic lobe deformations were applied to the phantom with subsequent repeat CT scanning. The phantom contained 6 subsurface tumor-like targets that could easily be tracked in repeat scanning and were used for validation and error assessment. Upon initialization by either ICP or the DIRR, the incremental model-correction framework was applied and average target registration error was tabulated. Table 1 lists the findings regarding the target registration error for subsurface targets after the full correction. When comparing to rigid ICP registration alone, the study demonstrates smaller target errors with model-correction and with either initialization method, i.e., the DIRR or ICP initialization. The study indicated improvement using the DIRR over the ICP method of initialization. It should also be noted that apart from these results, there were other important findings within [38]. For example, various strategies were employed within the FEM framework to account for large deformations that were of varying levels of computational efficiency. In addition to these phantom experiments, the method has also been preliminary tested on clinical cases in [43]. FIG. 9 illustrates an overlay of (1) the corrected image volumes in red, (2) the underlying preoperative CT scans, and (3) the intraoperatively acquired LRS data registered to the CT volume as shown by the white contour. In this study, the initialization was performed with ICP and the conformity of shape is encouraging given the better agreement between the red image volume and the white contour. Unfortunately, post-operative CTs were not taken in these cases or anatomical targets during the case for a more quantitative comparison. This however can be corrected by the methods of the present invention.

TABLE 1

Results of phantom deformation experiments showing target
error in millimeters for (a) using the complete surfaces
of the target and source for initialization, and (b) using
a realistic partial surface for to represent LRS data.

| | ICP-Complete | | DIRR-Complete | |
|---|---|---|---|---|
| | No Model | With Model | No Model | With Model |
| 1st Deformation | 5.7 | 2.7 | 9.9 | 1.7 |
| 2nd Deformation | 3 | 2.5 | 3 | 2.3 |
| 1st Deformation | 7.3 | 4.3 | 11.8 | 3.8 |
| 2nd Deformation | 3.8 | 3.5 | 3.4 | 2.4 |

The genesis of the DIRR was to try to secure alignment initializations that would enhance model-updating as evidenced in Table 1. While aspects of the DIRR were interesting, it became evident as OR experience continued that organ shape change was a more global event in many instances, as shown in FIGS. 8 and 9. The automatic delineation of a particular minimally-deforming region may not be possible in many clinical presentations. However, one feature that was continually noted from case to case was the identification of the falciform region on the liver surface which is reasonably identifiable on CT image volume renderings. In light of the sensitivity of the approaches to initialization, a newly proposed registration method is being currently investigated which is based on the concept of increasing the weighting of salient features such as the falciform region [44]. While the DIRR or standard ICP may be applicable in certain instances, more robust registration methods to handle the range of problems that can occur during clinical presentation would be desirable. Another aspect that became evident in OR experiences was that often the liver would deform in such a way that curvature would decrease. As a result, many of the registration methods would become confounded by local minima. FIGS. 10a and 10b demonstrates a clinical result whereby ICP has failed due to a lack of geometric features. In this case, the DIRR was not appropriate due to a more global shape change. FIGS. 10c-10d shows the corrected alignment using the new weighted salient-feature registration method. FIGS. 10b and 10d are the same as FIGS. 10a and 10c respectively, where the visualization has been modified to allow easy identification of the falciform regions.

D. Registration and Deformation Correction: One underpinning problem with image-guided techniques that continuously confounds large-scale adoption is the difficulty in accounting for soft tissue deformation. While pristine anatomical information and an abundance of functional imaging methods (fMR, PET, SPECT, etc.) are routinely acquired preoperatively, the translation of that information into a dynamic OR environment has been stymied. In recent years, the ability to co-register all of these forms of preoperative information has had significant advances e.g., [45-47]. However, sensitive anatomical landmarks, e.g., large subsurface vessels, could shift from their preoperative position due to intra-operative surgical deformations and injury could ensue. With respect to neurosurgery, rigid cranial constraints allow IGS to still have functional use within today's ORs despite deformations (although compensation for deformation is needed to improve IGS in this application also). With abdominal organs such as the liver, IGS application is considerably more challenging. The lack of landmarks, rigid or otherwise, for patient-to-image registration is one particular challenge. Additionally, in exploratory liver surgery, the surgical presentation of the organ is significantly deformed from its preoperative state. As a result, even if landmarks were available on the liver, the organ is already significantly distorted prior to patient-to-image registration. The methods underpinning the deformation correction strategy is to combine rigid and non-rigid techniques for organ-to-organ registration, i.e. segmented liver volume-to-acquired laser range scanned liver.

Figure 11:
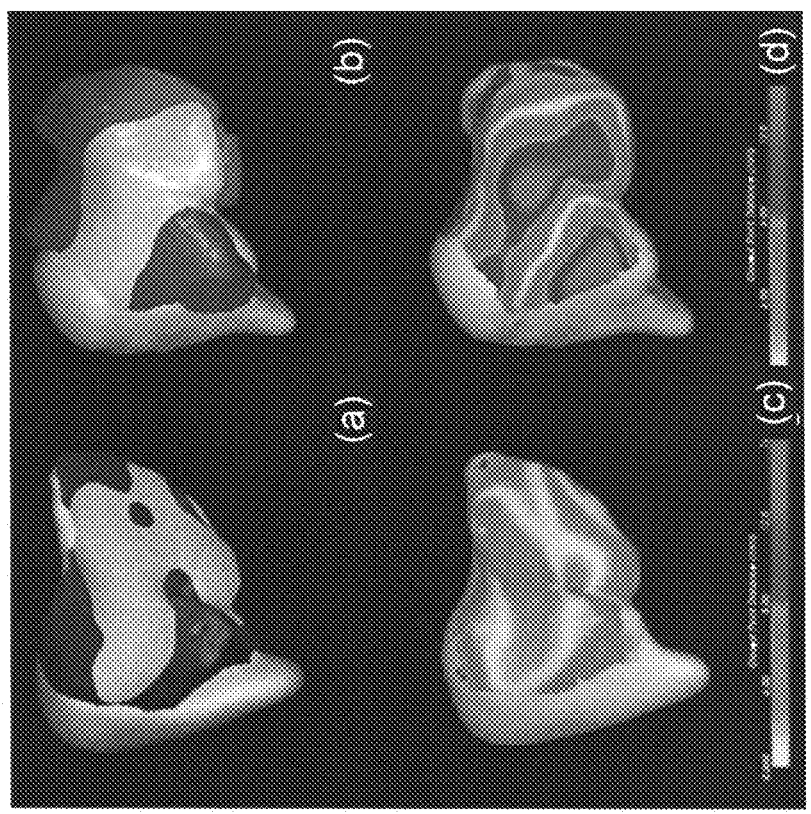
FIG. 11 shows (a) and (b) two clinical cases showing LRS-to-preoperative image registration, and (c) and (d) mapped closest point distance (color bar range is 0-16 mm for both (c), (d)).

In this embodiment, data that characterizes the shape of the visible organ surface during surgery will be obtained using the laser range scanning methodology. This data will be used to analyze the nature of soft tissue liver deformations, and to generate novel methods to correct for organ shift thus allowing for accurate patient-to-image registration. FIGS. 11a-11d show examples of how cases vary. FIGS. 11a and 11b show two example registrations between the liver surface as generated by the CT (gray) and the LRS surface (red). FIGS. 11c and 11d quantify the closest point distance between these two surfaces post-surface registration and demonstrate the variability in deformation that can occur. While the results from FIG. 12c may be acceptable, the results from 12d are more deleterious to guidance. This variability in organ registration is a significant hurdle for translating IGS techniques to the extracranial environment.

In previous work, the general approach that was investigated was to address this problem in five steps: (1) generation of a patient-specific computer model of the liver from preoperative CT images, (2) acquisition of the intraoperative organ surface using LRS, (3) application of an initial "best"-rigid alignment (e.g. DIRR from above), (4) non-rigid mapping of the preoperative organ to the intra-operative state using a finite element model of soft-tissue deformation, and finally, (5) the deforming of all preoperative images based on the deformation field as calculated by the model. In step (3), the term "best"-rigid is still being defined. For example, it is not clear that starting the non-rigid alignment of step (4) from an initial registration that minimizes the sum of the squared signed distance error is better than some other registration transformation (e.g. ICP, DIRR, or weighted salient-feature will all provide different initializations) [38, 48]. With respect to the DIRR, it was found that in many cases the amount of surface information needed to constrain the DIRR exceeded that which could be routinely acquired in the OR. Additionally, often the deformation was more global resulting in a reduction in geometric feature that would confound the DIRR with local minima, as well as ICP (see, for example, in FIGS. 10a and 10b). While investigation of this methodology is ongoing, expansion towards more robust initialization and computational efficiency is desired.

Accordingly, a weighted point-based registration approach was generated that uses a relatively novel weighted correspondence method based on salient features [44] and is presented in Example 3 below. The impetus for the development was the routine identification of the falciform ligament area within CT and LRS data. Briefly stated, the algorithm weighs salient features (such as the falciform) on both source and target surfaces more prominently for correspondence. The weights are exclusive in that only when a correspondence is determined between two salient features is the weight non-zero. This operation allows for a more aggressive initialization. In addition, the weights are dynamic and are described by the following expression, $$W_{PBR}(1) = W_{PBR,base} + (\Delta W_{PBR})\exp[-\alpha(i-1)] \quad (3)$$

Where $W_{PBR,base}$ is a baseline weight between salient features, $\Delta W_{PBR}$ is an initial amplification factor to more aggressively align these features in early iterations, and α is a decay rate for the amplification factor. Initial results using this approach have been encouraging and can be seen in FIGS. 10c-10d. The details of the salient feature weighting algorithm are described in Example 3 below [49] and continue to evolve as more experience is gained from the OR environment.

Figure 10:
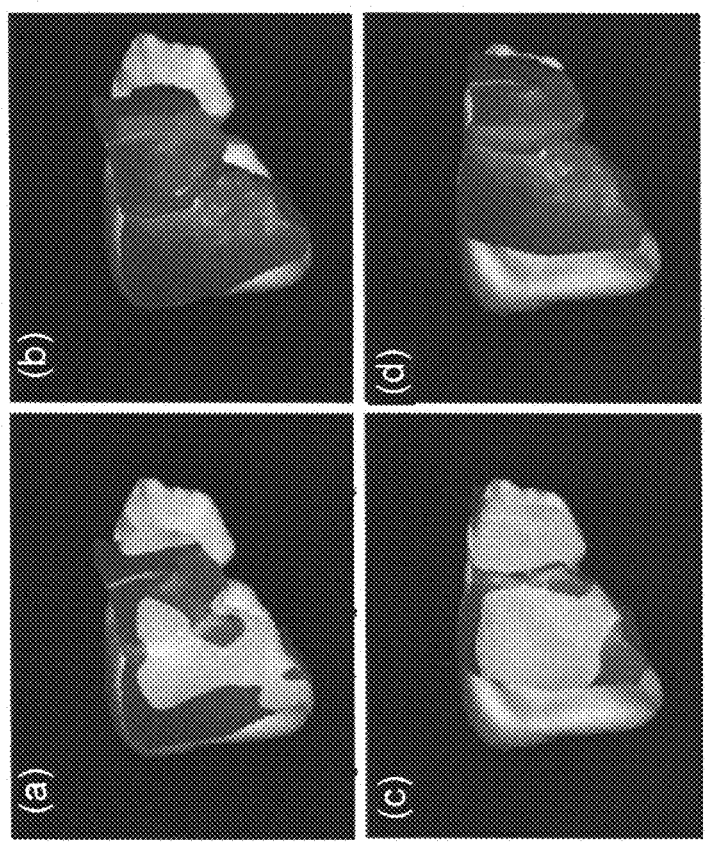
FIG. 10 shows clinical results showing visualizations of (a), (b) ICP registration, and (c), (d) the salient-feature weighted registration, where Falciform regions are highlighted.

While preliminary results with the incremental FEM approach, as shown in FIGS. 8, 9 and 10, have been encouraging and computational times associated with the framework are somewhat tractable, the need for a shift correction strategy that is more automated, more robust, faster, and equally as accurate would be desirable. To accomplish this, a novel approach is being investigated that regresses a deformed liver shape from an atlas of shapes such that it best fits LRS intra-operative surface data while simultaneously registering to that surface using the salient-feature weighted registration method. This approach can only be successful if an atlas of sufficient resolution can be generated. Based on OR experiences, it is hypothesized that an atlas of deformations could be pre-computed prior to surgery and would be sufficient to capture the dynamic OR events that affect liver shape. As part of that hypothesis, it is proposed that gravity may play an important role in correcting for liver deformations and needs to be included in the atlas of deformations. In FIG. 10c, a clinical registration result is shown and illustrates that the curvature of the intraoperative liver surface in (red) has become more planar than the preoperative segmented liver counterpart. While gravitational loading is experienced similarly both preoperatively during imaging, and intraoperatively during surgery, there is change to the supportive forces intraoperatively and the orientation of the liver with respect to gravity. During surgery, the liver is separated from its supportive constraints which allows for more degrees of freedom that would inevitably result in deformation. To correct this, the atlas of deformed liver shapes will contain solutions with varying surgical constraints and changes in the direction of gravitational loading. Based on OR experiences, dorsal regions of segments V-VIII are areas one would expect minimal deformation and would prescribe fixed or constrained displacements. Other regions would remain largely stress free with medial and lateral edges of the organ allowed to move along the abdominal wall surface but constrained to minimally deform in a direction normal to the surface. Similar approaches are being pursued within the neurosurgery context with considerable success [50-52].

As experience grows in the OR, other manipulations may be built into the atlas such as distinct lobe deformations similar to that in FIG. 5a. Another natural addition to the atlas will be variability in mechanical properties. Given the state of disease and other mitigating factors, it is possible that liver may contain varying degrees of fibrosis. As a result, the inclusion of mechanical parameters within the atlas may be necessary. This range will be determined in specific aim #3 and is anticipated to yield 3-4 values to capture the range.

Figure 12:
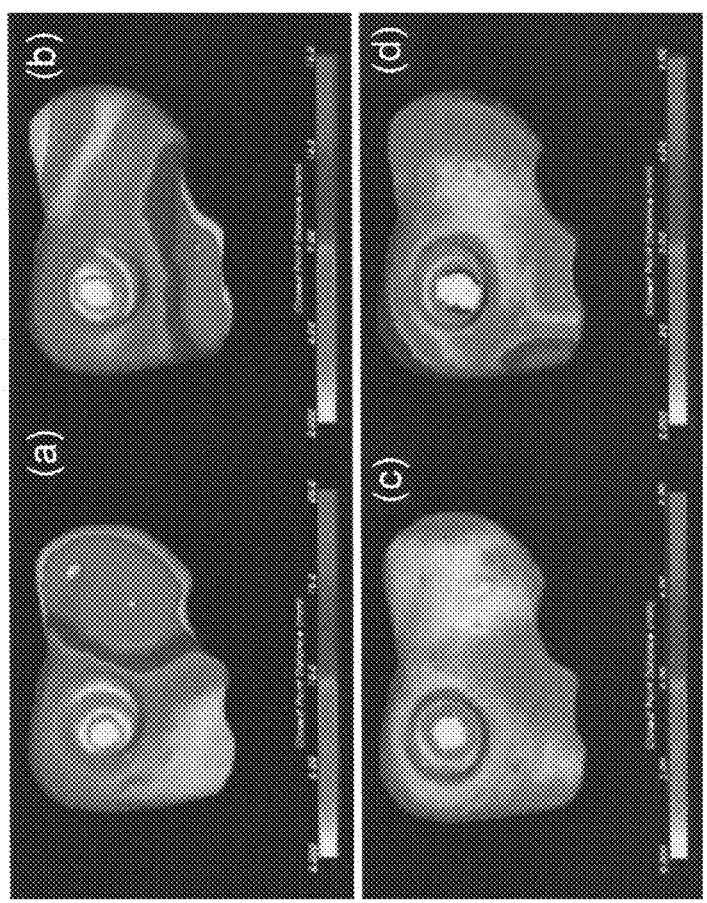
FIG. 12 shows (a) closest point distances from undeformed and deformed surfaces for deformation 1, and (b) deformation 2, and (c) and (d) same after ICAt registration, where color bar range for (a)-(d) is from 0 to 20, 18, 8, 6 mm, respectively.

In one embodiment, an initial atlas includes approximately 30-35 different organ orientations with respect to gravity, up to 5 different boundary condition realizations for each orientation, and up to 3-4 values of mechanical properties. This constitutes an atlas of approximately 700 solutions. On an 8-processor blade with a reasonably discretized FE mesh (about 100,000-150,000 elements), each solution takes approximately 45 seconds with the entire atlas being built in approximately 9 hours. Given the preoperative preparation time, this is sufficient; however, this will almost certainly change with the faster CPUs continually on the horizon. The approach to deformation compensation is a combined alignment and organ-to-organ shape conforming approach and is inspired by work from [53-58]. The algorithm begins with equally weighted regression coefficients that represent the weighting of each deformed shape from the atlas. From this shape called the source, correspondence between the source and the target (intra-operative laser range scanner data of the liver) is established using the salient-feature weighted closest point metric and a weighted point-based alignment [59] of the target is performed. Once achieved, a second closest Euclidean distance operation is calculated to establish correspondence. A new set of regression coefficients is calculated with $$[A]^T[A]\{\alpha\}+[\Lambda]=[A]^T\{s\} \quad (4)$$

where [A] represents the an n×m deformed shape atlas (where n is the number of points on the matching surface and m is the number of shapes within the atlas), $\{\alpha\}$ are the regression coefficients, $[\Lambda]$ is a regularization matrix (typically a diagonalized matrix based on the properties of [A] or other shape constraints), and $\{s\}$ is the reference shape as defined by the source and the closest point correspondence. While this equation is relatively simple, constraints to the range of regression coefficients, alternative regularization methods, and different correspondence methods are under investigation. Once the new shape is calculated, the process proceeds iteratively by performing another salient-feature registration, followed by surface fitting, and so forth. This specific formulation is called an iterative closest atlas (ICAt) method. The unique combination of techniques, such as weighted registration, regression, regularization, closest point, etc., embeds the ICAt method as a deformation correction strategy for image-guided liver surgery using sparse intra-operative data is significantly innovative. A preliminary result demonstrating the approach using the same phantom experiments of FIGS. 5-8, and Table 1 is shown in FIG. 12. The target registration error for the 6 tumor-like targets was 3.9 and 2.8 mm for deformations 1 and 2, respectively, comparing to Table 1b. While the results are comparable to the DIRR, the registration times have dramatically improved from 15-25 minutes for Table 1 results to 15-25 seconds in FIG. 12. Of note with these experiments is that the salient-feature weighting was not used in this result. It is anticipated that incorporation of the salient-feature weighting will add further improvement.

The rationale for pursuing atlas based techniques is that it allows one to deform the liver under a variety of deformation conditions that are more complicated than simply "pushing" on the organ. For example, deformation due to gravity represents a distributed load on the organ as opposed to a surface loading condition, i.e. applying a direct deformation to the organ surface. The subsurface deformation behavior associated with a distributed load is very different than a surface loading as shown in [60]. Building an atlas allows a range of deformed liver shapes under many different loading scenarios; and, given that information regarding material properties is unknown, atlas-based methods allow this information to be added relatively easily. Additionally, since information regarding posterior constraints on the liver is difficult, an atlas-based approach allows us to incorporate variability in these conditions quite easily which may in fact vary from surgeon to surgeon depending on their procedures. The last distinct advantage is that all FEM calculations are done preoperatively which makes model-compensation a reality for today's OR environment.

One aspect not mentioned above with respect to deformation is that during a procedure, the liver is in constant motion due to respiration. The liver motion is accounted in clinical experiments by suspending respiration during brief apneic periods. These apneic periods were performed at the same location in the respiratory cycle, so that the liver would reside approximately in the same location for every registration. This technique, which is controlled by the anesthesiologist, is most frequently utilized during thoracic procedures when lung expansion impedes the operative procedure. The level of anesthesia is monitored with continuous computerized EEG and computerized bispectral index (BIS), which provides a correlation between the depth of anesthesia and the possibility of the patient being awake during surgery. There are 2-5 brief apneic periods during a procedure, each lasting no more than four minutes.

E. Separate Compute Node Strategy: In order to achieve deformation correction capabilities for image-guided surgical systems in the liver, the initial realization will be performed on a blade configuration with 8 64-bit AMD Opteron 800 Series Dual-Core Processors as provided in the PRIMERGY BX630 eight socket AMD Opteron Processor server blade of Fujitsu. Since the blade contains 8 sockets and with each socket capable of supporting a dual-core processor, the unit has the capability to become a 16 core machine. This compact single blade system should allow for rapid calculation of highly resolved FEM meshes as well as image deforming capabilities. Although some may view a separate compute node strategy as cumbersome, the compact nature of a blade system allows its placement on the most surgical platforms thus eliminating a remote computing scenario and concerns over data transmission security. All data is ported to the correction node which includes the segmented liver image volume and LRS data. Currently PTI's system performs an iterative closest point registration on the main processor to provide physical-to-image registration. One of the objectives of the invention is to revite novel non-rigid registration methods on the correction node to compensate for organ deformation during surgical presentation. Accordingly, the general preoperative procedure entails that at least one day prior to surgery: (1) a CT liver image volume is acquired, (2) a preoperative planning session is performed (15-20 minutes) where segmentation and salient features are designated (salient feature will predominantly reflect the location of the falciform ligament region), and (3) once complete, automatic mesh generation, boundary condition deployment, and atlas solution generation are performed prior to the case. In one embodiment, within the operative setting, the organ is presented, laser range scan data is acquired, and the non-rigid registration method is performed followed by an updated (i.e. deformed) image set for the surgeon. The providing of LRS data through a secure socket connection to the node would initiate correction. Once completed, a new deformed image set is loaded into the visualization and guidance modules automatically.

F. Clinical Trial: In one embodiment, each of three early-adopter sites of the system is tasked with conducting a 15-20 patient study with the following guidelines. Patients are screened and given written consent before participating in this clinical trial. Subjects of interest are recruited based on the severity of their disease, and only those patients with single or multiple tumors requiring at least two anatomic segment resections are included in this particular trial. Prior to receiving any treatment, the patients undergo a physical exam, laboratory tests, and a chest x-ray to determine their overall medical condition as well as their ability to undergo surgery. The laboratory tests, physical exams and pre-operative treatment procedures (e.g., arteriography, portal venous embolization, etc.) utilized in this study are scheduled based on specific tumor type, disease setting and surgeon preference. These are all considered standard of care. Tomographic imaging (CT, MR, and/or PET) of the liver is the only imaging study that is necessary, which is also part of standard care for patients with liver tumors undergoing surgical resection. The abdominal CT scan is a triphase study of uncontrasted acquisition, venous phase contrast, and arterial phase contrast. The venous phase contrasted study is used for the image-guided surgery study, and its slice thickness is approximately 2.5 mm. The other phases have slice thickness of about 5.0 mm.

For participating patients, the surgeon localizes anatomic landmarks from the scans. These landmarks are also physically localized at the time of surgery. The liver's surface is segmented by the semi-automatic segmentation techniques discussed previously. The results from this method are reviewed by the surgeon (i.e., investigator at the clinical site) and modified if necessary. An ultrasound is done during the surgery to confirm the location of all tumors. All procedures above are standard therapy for a patient prior to hepatic resection. The preoperative segmented liver surface extracted from the CT is used in several stages of this investigation. From the scans, total functional liver volume is determined by subtracting tumor volume from total liver volume. The segmented scans are also used as part of the image to physical space registration process detailed below.

A standard laparotomy surgical procedure is performed, followed by liver mobilization. These are all standard procedures for major liver surgery. As previously mentioned, planned periods of apnea are used to decrease liver motion. With the addition of apneic periods and guidance, it is estimated that the entire operative procedure itself would potentially be lengthened a minimal amount (maximum 20 minutes duration). Liver ablation and resection procedures generally require at least 4-6 hours, so this would represent a very minimal alteration in the standard operative procedure. Collection of physical space points on the liver's surface takes place during the apneic periods. Before any surfaces are acquired, there is an apneic period to acquire anatomic landmarks with the optically localized surgical probe. Typically, 4 to 7 anatomic landmarks are acquired. The landmarks are chosen based on the ability to localize them accurately within both image and physical space. Landmarks may be anatomic (i.e. infrahepatic/suprahepatic vena cava, tip of the gall bladder, tip of the right lobe, portal vein bifurcation) or geometrically unique (inferior edge at segments IV and V, groove underneath falciform ligament, junction between segment III and IV). These landmarks are also identified and localized on the CT and/or MR image volumes or 3D reconstructions and used as targets to verify the accuracy of the registration process. The next apneic period is used for surface acquisition and image registration, which involves the laser range scanner and the other components of the IGLS device under investigation. The range scanner is mounted to a cart and swung into the sterile field, one to two feet away from the liver. Measures to protect the sterile field are under the surgeon's discretion. Note that this method does not require any contact with the patient. There is a brief period of positioning and calibration of the scanner, which takes less than one minute and does not require an apneic period. Once the scanner is in place, the apneic period begins and a laser range scan is acquired. The time required for the surface scanning process is 8-15 seconds and approximately 20,000 liver surface points are acquired during this time. The laser used is low power, considered eye-safe by the FDA and orders of magnitude below the Maximum Permissible Exposure level for skin as stated in the American National Standard for Safe Use of Lasers (ANSI Z136.1). Once a surface is acquired in the operating room, it is registered with the segmented CT and/or MR liver surface using the iterative closest point method. Once the mapping has been determined, the surgeon will use the preoperatively acquired images and corresponding surface and volume renderings to resect the tumor and surrounding tissue. This image-guidance augments the standard surgical procedure that is conducted. After the resection procedure is completed, a CT is acquired within 5 days. The parameters for these scans are the same as above. The liver is segmented from these scans using the semi-automatic methods, and results from this segmentation method will be reviewed by the surgeon and modified if necessary. Residual liver volume is calculated from these scans and expressed as a percentage of total functional liver volume calculated from the preoperative scans.

The data described above is used for a retrospective evaluation of the correction approach. Anatomical targets are designated by each site and used in validation of PTI's current approach. These same targets are available for retrospective analysis. In addition, information regarding salient features and their correspondence will be quantified, i.e., specifically closest point distances, and curvature assessments. The results shown in FIGS. 9-12 suggest the value of this evaluation strategy. In addition, at one site (St. Louis site), additional data is taken regarding the initiation of resection on the liver surface. More specifically, the optical stylus is used to designate spatially on the OR liver surface where a resection begins. This allows for two predicted respective volumes to be calculated based on a rigid registration approach and the novel correcting approach. The volumes are then compared to the OR volume collected as well as the one predicted by analyzing the pre-post CT image volumes. Given that exploratory liver surgery is not performed within an intra-operative imaging unit, the collection of this data and the analysis proposed provides sufficient validation for the approach.

G. Model Improvements & Mechanical Property Assessment: As mentioned above, it would be desirable to build in a realistic range of mechanical properties to the atlas. As FIG. 11 suggests, the extent of deformation can be different for two similar cases. While the discrepancy could be related to differences in organ presentation, the possibility that mechanical properties vary from patient-to-patient must not be neglected as a potential cause especially given the extensive range of functional tasks of the liver and the affects that lifestyle can have on the pliability of the organ.

Figure 13:
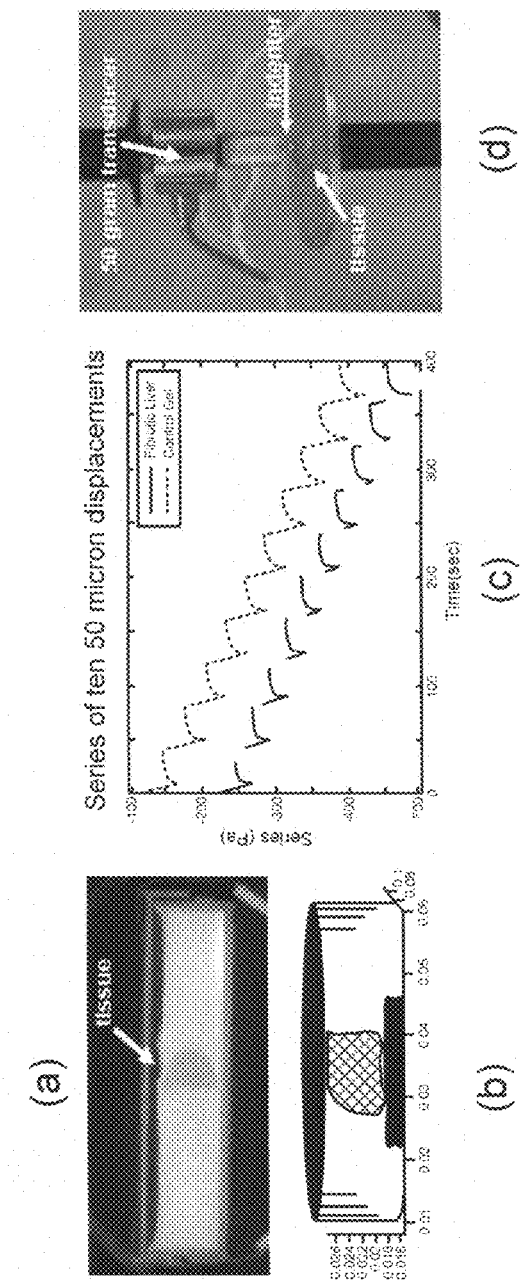
FIG. 13 shows (a) microCT of gel-tissue, (b) FEM mesh, (c) mechanical testing of gel-tissue, and gel control, and (d) indentation of a mouse liver.

As a result, interrogating liver ex vivo specimens from the OR at Vanderbilt University is proposed. In one embodiment, measurements of soft-tissue properties are performed using an experimental gel-tissue mechanical assay with the Enduratec ELF 3100 mechanical tester. The assay involves the following steps: (1) samples are immediately suspended post-resection within a polyacrylamide gel doped with CT contrast agent, (2) a microCT image volume is obtained, (3) mechanical testing in the ELF 3100 is conducted, and, (4) finite element model analysis is conducted. FIG. 13a shows the microCT of a gel-tissue suspension, where the tissue shown is a mouse liver. FIG. 13b shows the computational model built from the CT, which is sliced through part of the boundary so that the internal soft-tissue mass can be observed. FIG. 13c shows an example of mechanical testing with the ELF3100. In addition, a reference gel made from the same polyacrylamide stock is also made for independent tests to obtain background gel properties (one of the traces in FIG. 13c). Upon completion of testing, the computer model is used to simulate the compression and the mechanical properties of the tissue specimen are determined. It is important to note that viscoelastic effects have been observed in this data; but currently, analysis is performed after a dwell period to factor out transient effects. It is expected that in the future developing more sophisticated models which could include these effects as well as geometric nonlinearities. FIG. 13d shows a recent development towards indentation testing of tissue samples. While the model is used to determine properties for the gel-tissue assay, elastic indentation analysis theory is being used for determining properties with respect to FIG. 13d. Correlation of these testing methods increases the certainty of measurements.

Example 2

Compensating for Intraoperative Soft-Tissue Deformations Using Incomplete Surface Data and Finite Elements The IGLS requires the ability to identify and compensate for soft tissue deformation in the organ. The predeformed state is represented as a complete three-dimensional surface of the organ, while the intraoperative data is a range scan point cloud acquired from the exposed liver surface. The first step is to rigidly align the coordinate systems of the intraoperative and preoperative data. Most traditional rigid registration methods minimize an error metric over the entire data set. In this Example, a new deformation-identifying rigid registration (DIRR) is reported that identifies and aligns minimally deformed regions of the data using a modified closest point distance cost function. Once a rigid alignment has been established, deformation is accounted for using a linearly elastic finite element model (FEM) and implemented using an incremental framework to resolve geometric nonlinearities. Boundary conditions for the incremental formulation are generated from intraoperatively acquired range scan surfaces of the exposed liver surface. A series of phantom experiments is presented to assess the fidelity of the DIRR and the combined DIRR/FEM approaches separately. The DIRR approach identified deforming regions in 90% of cases under conditions of realistic surgical exposure. With respect to the DIRR/FEM algorithm, subsurface target errors were correctly located to within 4 mm in phantom experiments.

Methods

A. Overview: The details of the individual steps of model-updating image-guided liver surgery (MUIGLS) are described in the subsequent sections. Preoperative image data is acquired of the patient's abdomen using CT or MR scans. From these preoperative scans, the liver is segmented, and a three-dimensional surface is tessellated. This surface is used to determine a rigid alignment with respect to the intraoperative range scan data. Rather than perform this registration using the traditional ICP method, a new form of alignment that weights regions of the data that are minimally deformed is developed. The tesselated surface also serves as the input for generation of a tetrahedral volumetric mesh that will be the basis for a finite element model. Before running the FEM, boundary conditions are constructed based on the rigidly registered intraoperative data. The closest point distance between a boundary node of interest and the intraoperative, deformed surface is calculated. Execution of the model is repeated in an incremental fashion. Rather than using the entire closest point distance, a fraction of this value is used to prescribe the displacement boundary condition on the node. Each successive solution of the model updates the location of the mesh nodes, which triggers the calculation of new correspondences and boundary condition values. The model is repeated until the root mean square (RMS) closest point distances for all boundary nodes using the closest point boundary condition has reached some predetermined value. The results from the FEM are used to warp the preoperative image to match the intraoperative presentation.

Before explaining the methods used in MUIGLS, it is necessary to state some of the assumptions regarding image-guided liver surgery. From observing procedures in the OR, the liver is assumed to be an elastic substance. Unlike neurosurgery, there are no apparent fluid effects in the organ, so there is no shrinking or swelling and volume is preserved. The most obvious feature of the deformation appears to be a shape change, where one region of the liver surface changes relative position with respect to another region. Often the deformation can be concentrated in a central region of the liver whereby a significant amount of semi-rigid translation and rotation is experienced by areas in the organ periphery, i.e., a lever-arm effect occurs due to significant deformations located more central to the organ. Translational effects due to forces such as diaphragm motion have been discussed in previous research [24] and are taken into account by employing breath-hold protocols [36]. During the surgery, the liver may change shape because of manipulation by the surgeon or resection, and this will warrant a new registration. At that point, the laser scanner will acquire a new intraoperative surface, so that the registration and deformation compensation will be recomputed. "Minimally deformed" areas are considered to be those which undergo deformation no greater than a few millimeters as determined by visual inspection. The goal in MUIGLS is to reduce the amount of error from large scale deformations (1-4 cm) below the previously stated 1 cm level of target registration accuracy while not causing additional error seen in the minimally deformed regions.

Figure 14:
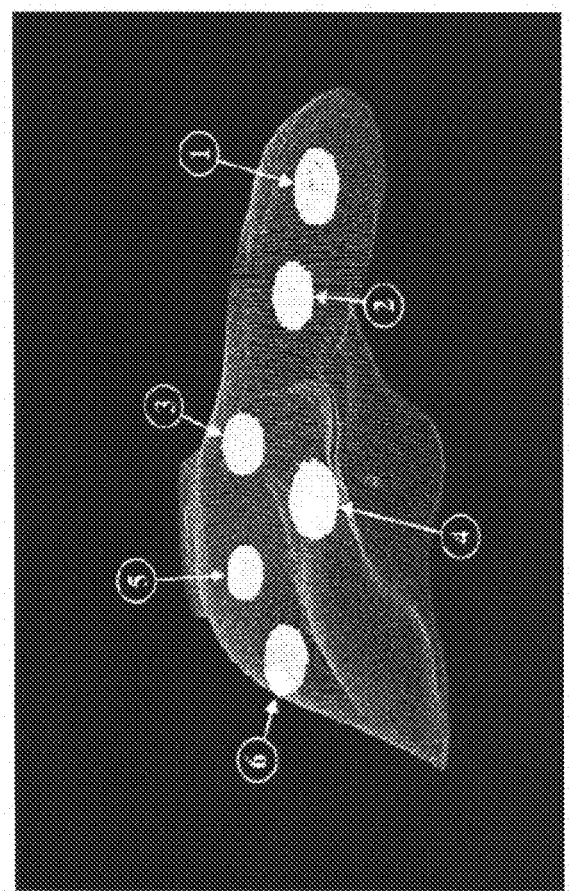
FIG. 14 shows a segmented CT surface of the liver phantom with subsurface tumors, where the labels for each tumor is used as a reference for the results.

B. Data Representation: Phantom studies were performed on a poly (dimethyl) siloxane (rubber silicone) model of the liver, which is attached to a plexiglass base. Two sets of point-based landmarks are used for the study. Surrounding the outskirts of the phantom are vertical cylinders also attached to the vertical base, where seven white Teflon spheres have been placed in machined holders at the cylinder tops to serve as fiducials for a point-based registration. Inside the liver are mock tumors made of styrofoam, which are spherical with a radius on the order of about 1-1.5 cm. The intensity of these tumors is approximately 20 times lower than the surrounding phantom, allowing for the tumors to be easily segmented with a simple region growing algorithm. The centroids of these tumors will serve as subsurface targets for accuracy studies. The position of the targets within the phantom is shown in FIG. 14. To induce a deformation in the phantom, an object of height about 38.0 mm is placed underneath a region of the model. A large nylon screw pinned down other regions of the phantom and kept them stationary. Two different sites were chosen for deformation. These locations were chosen to mimic some of the physical manipulations that a surgeon may perform during a procedure. The first deformation occurred under the left lobe, where tumors 1 and 2 experienced the most shift, while the second site was at the middle of the inferior ridge, underneath segments III, IV, and V. For this case, the largest shift occurred at tumors 4 and 6. CT scans and range scans were taken while the phantom was in the nondeformed state and for each one of the deformed states. Corresponding slices from the nondeformed tomogram and one of the deformed volumes are shown in FIG. 15, where corresponding CT slices are acquired from (a) nondeformed and (b) deformed image. The plastic object placed below the liver produces the deformation. The height of the object is approximately 38 mm.

C. Identification of Deformation: According to one embodiment of the present invention, the first step in MUIGLS is the rigid alignment between the preoperative and intraoperative coordinate systems. Although conventional rigid registrations are relatively easy to implement, they are also susceptible to misalignment caused by deformation. It is possible to reduce the effects of deformation on rigid registration by identifying areas that are minimally deformed and using only landmarks in these regions for the registration. The effects of identifying minimally deformed regions are illustrated with the ICP algorithm that is a common method of registering two surfaces. The ICP algorithm relies on the closest point distance metric. For the i-th point in data set X, the closest point distance $d_{cp,i}$ is defined as the minimum distance from this point to a landmark in the other data set Y $$d_{cp,i} = d(X_i, Y) = \arg\min|_{y \in Y} dis(X_i, y) \quad (5)$$

Figure 16:
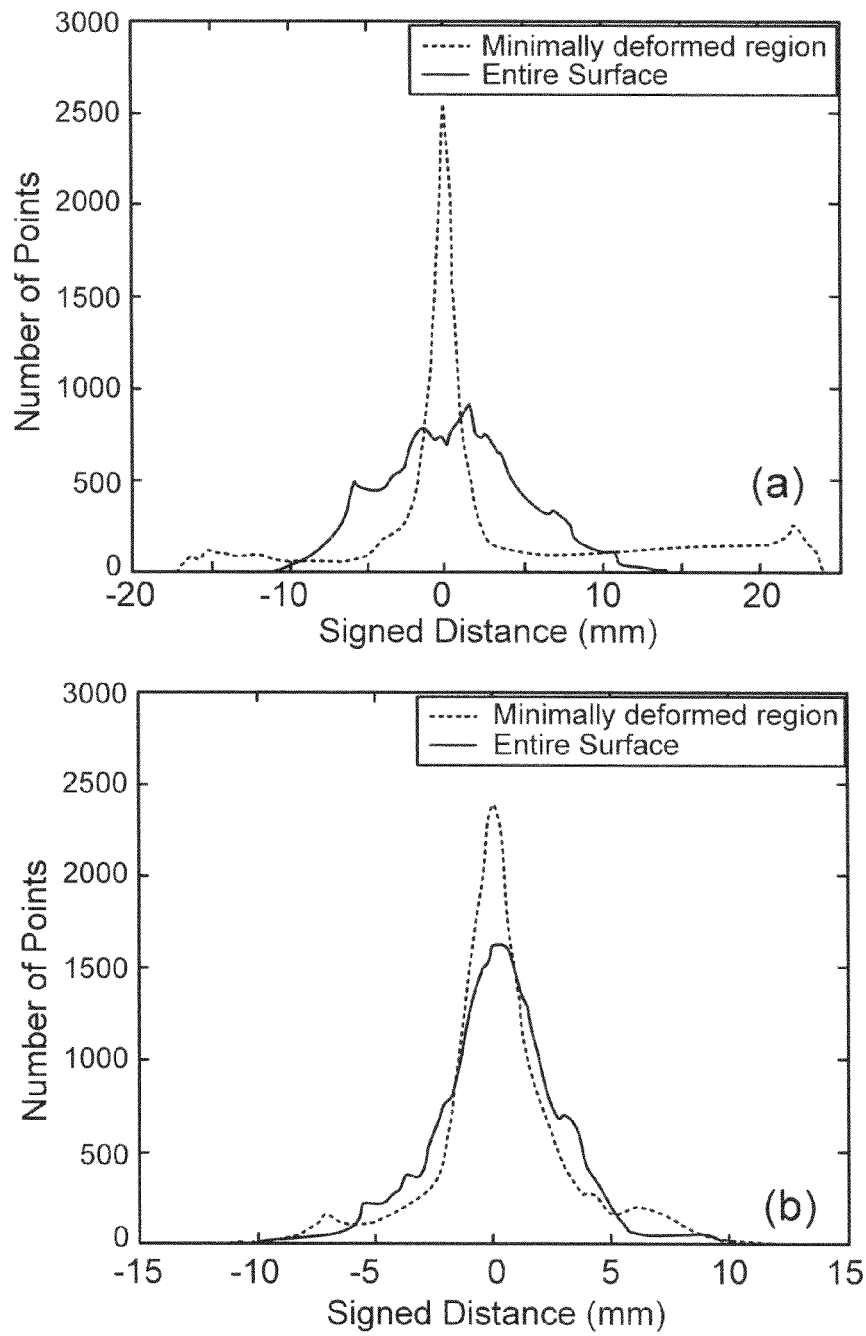
FIG. 16 shows a histogram of signed distance distribution for rigid alignments between a nondeformed surface and the surface deformed at (a) the left lobe and (b) the inferior ridge. The solid line indicates that the alignment is performed by registering the entire surface with the ICP algorithm. The dashed line is acquired with the same registration method, but this time only regions of the surface that were visually identified as "minimally deformed" are used in the registration.

In the ICP algorithm, the RMS residual of closest point distances over the entire surface is the cost function that is minimized through the iterative process. However, more information can be obtained when examining a histogram of the signed distance value distribution at a given alignment. As shown in FIG. 16, a histogram of the signed distance distribution for rigid alignments between a nondeformed surface and the surface deformed at (a) the left lobe and (b) the inferior ridge. The solid line indicates that the alignment is performed by registering the entire surface with the ICP algorithm. The dashed line is acquired with the same registration method, but this time only regions of the surface that were visually identified as "minimally deformed" are used in the registration.

The signed distance indicates how far a point is outside of the surface (positive) or inside (negative). In this figure, the alignments were obtained using ICP: one scenario used the entire surface in the registration, while the other used only areas that were visually identified as minimally deformed. When using the entire surface in the registration, the signed distance histogram has a narrow band of values distributed in a relatively uniform fashion, as displayed by the solid lines in FIG. 16. When only the minimally deformed regions are registered using ICP, the histogram of signed distances has a much sharper peak at the histogram bins closest to zero, as indicated by the dashed lines. This alignment also produces a larger range of distance values that are associated with the deformed areas shown in FIG. 4a and play no role in this selective ICP alignment.

Often, information about the surface regions which are minimally deformed is not available a priori. A DIRR algorithm that aligns two surfaces according to the minimally deformed areas without any manual identification of these regions is developed. For each point i in the $N_S$ points of intraoperative data, a signed distance, $d_{s,i}$, to the nondeformed surface is calculated. These distance values are then used in the following cost function:

$$f(S) = \sum_{i=1}^{N_S} \exp\left[\frac{-d_{s,i}^2}{2\tau^2}\right] \quad (6)$$

The Gaussian term is similar to one used for fuzzy correspondence in the work of Chui et al. [42]. As more points approach a closest point distance of zero, the output value of the cost function will increase. At the same time, this cost function does not cause significant penalties for points which have large signed distances to the target surface that are associated with deformation. The parameter that controls the behavior of the cost function is the standard deviation of the gaussian function, $\tau$. This parameter usually ranges between about 0.5-2.0 mm. Currently, the cost function is optimized using Powell's method as implemented in the VXL library. The parameters for the optimization are the six degrees of freedom that represent the rigid transformation that is applied to the intraoperative-data. Unit quaternions represent the rotation.

In many cases, it is necessary to speed up calculations and provide smoother objective functions. The underlying surfaces of segmented preoperative data and intraoperative data were represented by radial basis functions (RBFs). A biharmonic RBF was used to interpolate the signed distance between any point in three dimensional space and the surface. The zero isocontour from the resulting RBF function represents the fitted surface. To make this method computationally efficient for large data sets, a special implementation which provides for the fast evaluation and solution of RBFs was used, developed by FarField Technology (FastRBF, Far Field Technology, Christchurch, NZ).

To test the DIRR algorithm, points sets from the deformed range scan and CT data were registered to the minimally deformed surfaces. These areas were manually designated from the surface by visual inspection and knowledge regarding the location of the object deforming the phantom. The minimally deformed areas were the only points used in an ICP registration, which served as a "ground truth" alignment to produce the same effect in the closest point histogram distribution as observed in FIG. 16. Then, the DIRR was performed without the aid of identifying the deformed surfaces. The results were compared to the ground truth using the six subsurface targets representing the tumor centroids. Like many registration algorithms, the DIRR needs an initial guess that roughly aligns the two surfaces. The initial alignment is achieved by identifying four landmarks on the phantom surface to serve as fiducials in a point-based registration.

To test the sensitivity of the DIRR to initial alignment, the position of each fiducial was randomly perturbed up to 1 cm away from its original position for 1000 trials. The results from the DIRR were compared against the ground truth and categorized as either a success or a failure. A success was defined as any registration where all tumor errors were less than 5.0 mm, which was confirmed by visually inspecting the resulting alignment.

D. Deformation Correction Using Finite Element Modeling: After the rigid alignment between the two coordinate systems has been established, the next step is to model the deformation using a finite element model. The mesh used in the model is constructed from the preoperative tomographic volume, which represents the nondeformed state of the organ. The first step in mesh generation is to segment the liver from the rest of the abdomen. Segmentation is performed either manually or using a semi-automatic method that is a modification of the level-set method. The manual segmentation requires many hours to perform, while the level-set method can usually be completed in 30 min to 1 h. From the segmented organ volume, a surface is tesselated using either the marching cubes method or the aforementioned surface fitting algorithm using RBFs. The surface is represented as a set of polygons and serves as input to the mesh generation software. This software uses the boundary description to generate a tetrahedral grid volume of the entire liver shape.

The deformation of the liver is modeled using a linear stress-strain relationship for an isotropic, three-dimensional solid. If static equilibrium is assumed, then $$\nabla \cdot \sigma = \vec{B} \quad (7)$$

where $\sigma$ is the stress tensor and B is the body force vector. Stress can be related to strain by the following relationship:

$$\sigma = C\epsilon \quad (8)$$

where C represents the material stiffness matrix. For a Hookean solid, C depends on two properties, Young's Modulus, E, and Poisson's ratio, $\nu$. The displacement vector, u, is the value that will be solved for, and it is related to normal strain $\epsilon$ and the shear strain $\gamma$ by $$\epsilon_x = \frac{\delta \mu_x}{\delta x}, \epsilon_y = \frac{\delta \mu_y}{\delta y}, \epsilon_z = \frac{\delta \mu_z}{\delta z}, \quad (9)$$

$$\gamma_{xy} = \frac{\delta \mu_x}{\delta y} + \frac{\delta \mu_y}{\delta x}, \gamma_{xz} = \frac{\delta \mu_x}{\delta z} + \frac{\delta \mu_z}{\delta x}, \gamma_{yz} = \frac{\delta \mu_y}{\delta z} + \frac{\delta \mu_z}{\delta y}, \quad (10)$$

where $\vec{u} = \{\mu_x, \mu_y, \mu_z\}$ is the cartesian displacement. By combining equations (7)-(10), a system of partial differential equations can be expressed in terms of the displacement vector, $\vec{u}$, to form the Navier equation $$\frac{E}{2(1+\nu)}\nabla^2 \vec{u} + \frac{E}{2(1+\nu)(1-2\nu)}\nabla(\nabla \cdot \vec{u}) = \vec{B} \quad (11)$$

The partial differential equation is solved using the Galerkin weighted residual technique with linear basis functions. The system of equations that solves for the displacement vectors at every node in the mesh can be written as $$[K]\{\vec{u}\} = \{b\} \quad (12)$$

Figure 17:
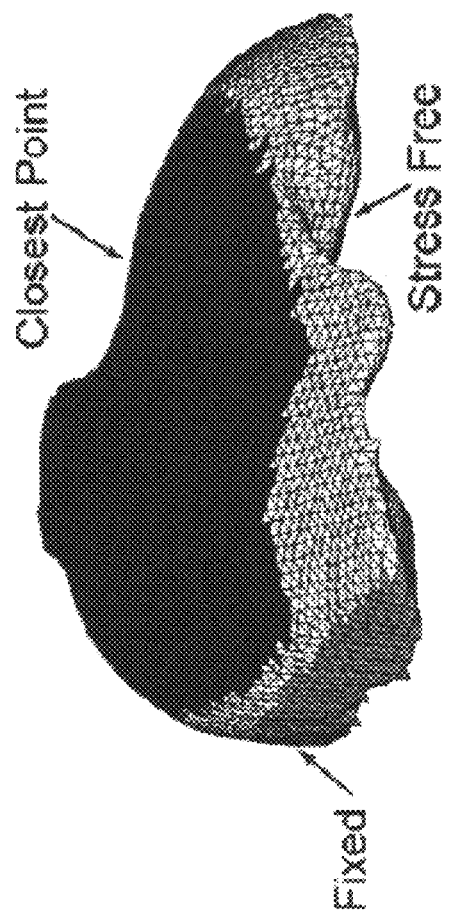
FIG. 17 shows an example set of boundary conditions for the liver phantom mesh. The dark grey represents the boundary nodes that obey the mixed "closest point" boundary condition formulation. The medium grey value denotes fixed regions, while the light grey boundary conditions are stress free.

One fundamental component to employing the finite element method is the prescription of boundary conditions. These boundary conditions are derived from knowledge of the forces applied to the liver within surgery as well as information from the intraoperative data. There are three different types of boundary conditions implemented in the model. The first set of boundary conditions are categorized as "fixed," a set of Dirichlet conditions representing immobile regions of the organ. Typically, obscured regions of the right lobe that rest against other parts of the viscera belong to the fixed category. "Stress-free" boundary conditions are the second category, which represent regions unrestricted by force. The final type will be referred to as "closest point" boundary conditions. These nodes play the most significant role in modeling the deformation and are considered a mixed boundary condition, in that, of the 3 vector components, one component is Dirichlet while the remaining two are Neumann conditions. An example of how the different regions of the organ are classified according to boundary condition type is illustrated in FIG. 17, where the dark grey represents the boundary nodes that obey the mixed "closest point" boundary condition formulation. The medium grey value denotes fixed regions, while the light grey boundary conditions are stress free.

The details in implementing the "closest point" boundary conditions are critical to successfully recovering the deformation in the approach. It should be noted that the initial DIRR is also integral to the prescription of boundary conditions; i.e., at the initiation of deformation, the closest point distances are directly related to the DIRR registration. Furthermore, with such a large amount of deformation present intraoperatively, improper correspondence can lead to boundary conditions that would cause improper nonrigid alignments and unrealistic distortions of the organ shape.

In this embodiment, two measures are taken to avoid improper correspondence when setting the displacements for the boundary conditions: 1) manipulation of the finite element equations such that the equations are sensitive to the organ surface geometry; 2) implementation of incremental solutions with a moving grid. The first involves modifying the conventional finite element method such that the weighted residual vector equations at the boundary are expressed in a coordinate reference that is designated to have one coordinate axis normal to the organ surface and the remaining two being tangent to that surface (as opposed to traditional Cartesian coordinate references). With respect to modeling anatomical organs and their deformations, there are some aspects to the application of boundary conditions that are particularly challenging to traditional Cartesian representations. For example, in the application of displacement boundary conditions to the liver, it is often desirable to express the movement of the boundary in a direction that is relative to the geometric shape, i.e., the coordinate system associated with directions that are approximately normal and tangential to the organ surface. One strategy is to take the desired normal displacement and convert this to its Cartesian counterparts, i.e., $$\begin{Bmatrix} dn \\ dt_1 \\ dt_2 \end{Bmatrix} = \begin{bmatrix} \vec{x}\cdot\vec{n} & \vec{y}\cdot\vec{n} & \vec{z}\cdot\vec{n} \\ \vec{x}\cdot\vec{t}_1 & \vec{y}\cdot\vec{t}_1 & \vec{z}\cdot\vec{t}_1 \\ \vec{x}\cdot\vec{t}_2 & \vec{y}\cdot\vec{t}_2 & \vec{z}\cdot\vec{t}_2 \end{bmatrix} \begin{Bmatrix} dx \\ dy \\ dz \end{Bmatrix} \quad (13)$$

where $\vec{n}$, $\vec{t}_1$, and $\vec{t}_2$ represent an orthogonal coordinate system with the normal (to the organ surface) and tangential axes, respectively. In this case, the inverse relationship in equation (13) would be used since the transformation shown is from Cartesian to normal-tangential space (n-t space). In these equations, the application of a displacement normal to an organ surface can be achieved; however, the ability to relate mixed boundary conditions within the n-t space framework is not possible using equation (13). For example, it may be desirable to allow an organ surface to slide along a supporting wall yet not deform in a direction normal to the wall, i.e., through the wall. In another situation, the deformation may need to be applied in a direction normal to the organ surface yet allow for sliding of tissue along the displacing surface (e.g., depressing the organ with a smooth object like a retractor). This type of boundary condition requires stress-free conditions tangent to the direction of constraint/motion and restricted normal displacements, e.g., $$\sigma_{t1}=\sigma_{t2}=0, u_n=0 \text{ (or } \alpha^*d_{cp,i}) \quad (14)$$

where $\sigma_{t1}$ and $\sigma_{t2}$ are stresses applied tangent to the organ surface, and $u_n$ is a displacement normal to the surface. In this instance, the framework described in (13) cannot achieve these degrees of freedom in organ movement behavior.

A better approach than using equation (13) is to rotate the equations of equilibrium for nodes concerned with the boundary into an n-t space coordinate reference. This process usually involves the use of rotational matrices (sensitive to the organ boundary) being applied at the local element assembly level $$[R]_i[K]_i[R^T]_j\{u\}_j=[R]_i\{b\}_i \quad (15)$$

where the premultiplication by $[R]_i$ on the left and right-hand side rotates the equilibrium equation and body force components ($[R]_i$ is the matrix shown in equation (13) and would be associated with the normal and tangential coordinates reference of the i-th node), and the $[R^T]_i$ multiplication rotates the displacement coefficients from Cartesian to the n-t space (i, j refer to i-th weighted residual equation, and j-th displacement coefficient, respectively). Careful attention must be paid to the determination of the rotational matrix, [R], and to the arrangement of rotational multiplications (note, that $[R^{-1}]$ is orthogonal and equivalent to $[R^T]$). This approach to n-t space calculation has been reported by Engelman et al. [63]. Based on the experience with realistic anatomical deformations in the brain and liver, this type of boundary condition formulation has great utility in prescribing tissue-mimicking deformations [48]. With respect to the approach, the "closest point" boundary condition is of the form expressed in equation (14) and is only possible through the formulation described by equation (15). More specifically, in these surface regions, the liver is prescribed to deform normal to the organ surface a designated amount (based on a fraction, α, of the closest point distance, $d_{cp,i}$) and is also allowed to slide tangentially to accommodate that motion.

Figure 18:
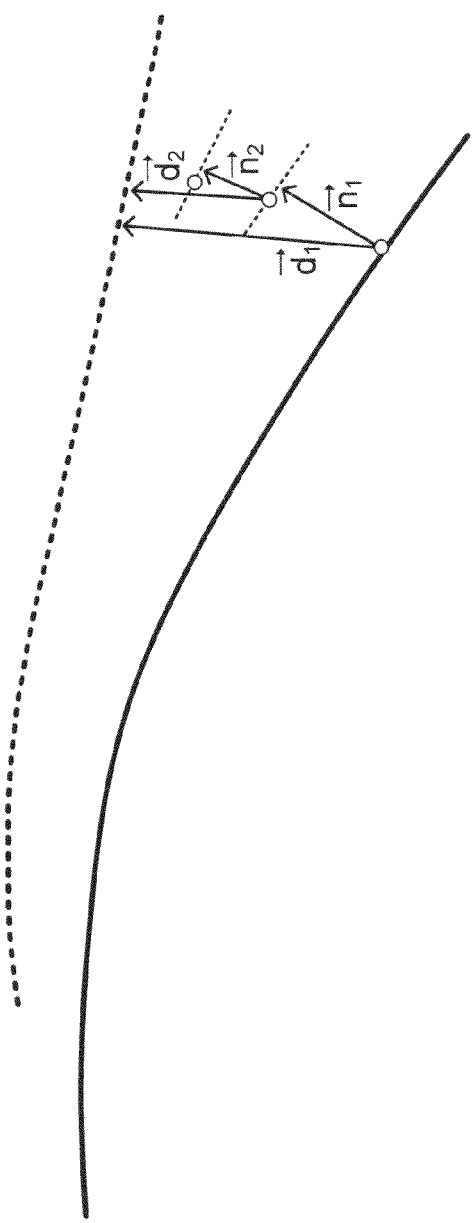
FIG. 18 shows implementation of "closest point" boundary conditions using normal tangential space. The closes point distance for the boundary node at increment 1, $\|\vec{d}_1\|=d_{cp,1}$, is determined. From $d_{cp,i}$, a normal distance, $\|\vec{n}_1\|=\alpha\ d_{cp,i}$, is computed for use in the "closest point" boundary condition where $\alpha$ is the solution scale fraction that scales the closest point distance in the incremental framework. The new position of the boundary node, denoted by the small circle, lies on a plane that is a distance of $\alpha\ d_{cp,i}$ along the direction $\vec{e}_{n1}$ away from its original location. The mixed formulation of the "closest point" boundary condition shown in equation (14) gives the node freedom to slide along this plane through the stress-free boundary conditions imposed on the two tangential axes. The same process is repeated for the second and subsequent increments.

The second measure to improve correspondence involves an incremental approach for the model-updating process. The technique uses an incremental application of the displacement boundary conditions in conjunction with a moving grid. The displacement increment size is not fixed; but rather, it is based on an attenuation of the value obtained from the closest point operator, which is recalculated before each incremental solution of the model. The advantages of this approach are that it avoids geometric nonlinearities and provides more realistic deformations by recalculating the surface normals based on the current deformed grid. Others have used similar approaches in the brain and have found the incremental approach to moderately improve the fidelity of the deformation modeling [72]. According to the invention, one of unique features is that the moving grid is being used within the updates to calculate new surface normals and closest point distances. In one embodiment, a stopping criterion used to halt the incremental updates is defined as the RMS distance to intraoperative data from all closest point boundary nodes. Once the average closest point distance is within about 1-2 mm, a final increment is calculated and applied. FIG. 18 shows the relationship for the first and second increments of the approach. The closest point distance between the boundary node position at the time of the first increment and the intraoperative data is calculated $\|\vec{d}_1\|=d_{cp,1}$. The normal distance, $\vec{n}_1=\alpha^*d_{cp,1}*\vec{e}_{n1}$, is calculated where α is the fraction by which the closest point distance is scaled, and $\vec{e}_{n1}$ is the unit vector associated with $\vec{n}_1$. The "closest point" boundary conditions are then set with the attenuated closest point distance designated as a Dirichlet condition along the normal direction and stress-free conditions for the two tangential axes, as described by equation (14). After the finite element model is calculated, the new position of the node (small circle) will lie on a plane formed by the tangential axes. This plane is a distance $\|\vec{n}_1\|$ away from the node's original plane. However, the node is not confined to reside along the normal due to the tangential stress-free conditions; therefore, the point to point distance is not required to equal $\|\vec{n}_1\|$. After the position has been updated, a new closest point distance $\|\vec{d}_2\|=d_{cp,2}$ and normal distance for the boundary condition $\vec{n}_2=\alpha^*d_{cp,2}*\vec{e}_{n2}$ are calculated.

With respect to the solution of equation (13), a sparse format and iterative solver were implemented using the Portable, Extensible Toolkit for Scientific Computation (PETSc) package [73], which is capable of solving large linear systems in parallel. For these experiments, the matrix was preconditioned using an incomplete LU factorization and an iterative solver based on the generalized minimal residual (GMRES) method [74].

Experiments were performed on the phantom data in order to examine the effects of various parameters involved in the incremental approach. For every finite element experiment, the partial surface from a deformed range scan data set was used to drive the model. Target registration error (TRE), as defined in Fitzpatrick et al. [75], was calculated using the subsurface tumors. The target positions from the nondeformed mesh were updated through the model and compared to the actual positions obtained from the CT volume of the deformed organ.

The implementation of "closest point" boundary conditions is an important factor with regards to accurately localizing targets. The cartesian representation for this category of boundary conditions was tested against rotating the node into a local normal-tangential coordinate system and prescribing the mixed boundary conditions as described above. Another factor affecting the closest point calculations was the initial alignment that was used to transform the intraoperative data. As a result, five separate registration methods were used to provide the initial alignment prior to performing FEM model-based compensation. The methods are shown in Table 2.

TABLE 2

Initial Alignment Methods for Intraoperative Range Scan Date In The FEM

| Alignment | Method | Non-deformed Surface | Deformed Surface |
| --- | --- | --- | --- |
| FID | Fiducials | N/A | N/A |
| ICP-WHOLE | ICP | COMPLETE CT | Complete CT |
| ICP-PARTIAL | ICP | COMPLETE CT | Partial Range Scan |
| DIRR-WHOLE | DIRR | COMPLETE CT | Complete CT |
| DIRR-PARTIAL | DIRR | COMPLETE CT | Partial Range Scan |

Since idle time is undesirable during surgery, the incremental finite element approach must be designed to be as expedient as possible. Computation time can be reduced through two measures. First, the number of increments can be decreased, which is achieved by increasing the solution scale constant responsible for attenuating the closest point distances before setting the boundary condition values, i.e., as the solution scale approaches unity, the number of increments decreases. The second method for reducing computation time is to make every incremental execution of the model faster. Within each successive solution of (12), the majority of computation is devoted to rebuilding the stiffness matrix and recalculating the preconditioner, which are necessary due to the dynamic grid. These steps can be completely avoided after the first increment by using the original mesh for every iteration, updating the boundary nodes and conditions separately, similar to the approach of Platenik et al. [72]. In this case, only the right-hand side is affected, and the individual solutions from each increment can be summed to determine the final displacements. When solving the model multiple times, the quality of the dynamic grid could degrade. To avoid a problem with mesh quality, the original mesh is used for each iteration, but the normals and boundary nodes are separately maintained and updated after each iteration. Since the normals vary, the rotation matrices will change and the stiffness matrix must be rebuilt. Thus, more computation time is likely required per incremental solution, but the original mesh structure is preserved, possibly enhancing performance of the solver by improving the condition number of the stiffness matrix in equation (12).

Results

Figure 19:
FIG. 19 shows various alignments of intraoperative range scan of phantom with the preoperative surface: (a) Using the surrounding extrinsic fiducials, (b) Using the complete surface data with ICP registration, and (c) using only the manually identified minimally deformed regions for the ICP. (c) serves as the ground truth for experiments testing the DIRR algorithm.

A. Deformation Identification: The "ground truth" for the rigid alignment involves manually identifying minimally deformed regions on the CT surface through visual inspection, and then using these regions in an ICP registration. When registering the minimally deformed region of the surface to the original volume, the RMS of the closest point distances was 0.9 mm (max closest point distance=3.3 mm) for the first deformation case using approximately 10,000 points, and 1.0 mm (max=3.4) for the second deformation, where the partial surface contained approximately 8800 points. As a comparison, the RMS of the closest point distances was 4.2 mm (max=14.3) and 2.6 mm (max=10.8 mm) for the two data sets when using the whole surface in the ICP registration. The differences between the fiducial registration, the whole surface ICP, and the "ground truth" alignment based on ICP using only the minimally deformed regions are displayed in FIG. 19, (a) using the surrounding extrinsic fiducials, (b) using the complete surface data with ICP registration, and (c) using only the manually identified minimally deformed regions for the ICP. FIG. 19c displaying the ground truth indicates a better alignment of the left side of the surface compared to the alignment obtained from the external fiducials, and will serve as the ground truth for experiments testing the DIRR algorithm.

To initialize the DIRRs optimization, four points representing landmarks on the surface were used for a fiducial-based registration. The fiducial registration error (FRE) is defined by the following equation [75]

$$FRE = \sqrt{\frac{1}{N}\sum_{i=1}^{N} |Rx_i + t - y_i|^2} \quad (16)$$

where N is the number of landmarks in point sets x and y, and R and t are the rotation and translation parameters that represent the rigid registration. The FRE for these initial registrations were 5.8 and 5.3 mm for the two cases using deformed CT data and 5.8 and 8.5 mm for range scan data. Since it is difficult to localize surface landmarks with a high degree of precision or accuracy, the position of the landmarks was perturbed by a distance of up to 1 cm. From these random perturbations, the initial alignment given to the DIRR was varied over 1000 trials. Table 3 shows the results of the DIRR registration experiments, with trials classified as a "success" or "failure" based on the definition given above. In all trials, the complete non-deformed surface from the CT data was used. For the deformed surface, columns two and three indicate the results when using complete surface data from CT volumes, and columns four and five display the results when using only the partial surface acquired from the range scanner.

TABLE 3

Results from the DIRR Algorithm. These Values are the Mean Distance, mm, from the Centroid Location Using the DIRR Alignment to the Corresponding Centroids at Ground Truth

| | Complete CT | | Incomplete Range Scan | |
| --- | --- | --- | --- | --- |
| | DIRR Success | DIRR Failure | DIRR Success | DIRR Failure |
| Deformation 1 | | | | |
| Trials | 999 | 1 | 903 | 97 |
| Tumor 1 | 1.6 | 26.4 | 3.6 | 19.2 |
| Tumor 2 | 1.2 | 139.2 | 2.9 | 15.0 |
| Tumor 3 | 0.5 | 11.2 | 1.8 | 7.6 |
| Tumor 4 | 0.7 | 7.2 | 0.9 | 5.0 |
| Tumor 5 | 0.5 | 9.7 | 2.5 | 4.1 |
| Tumor 6 | 0.8 | 9.4 | 1.4 | 4.3 |
| Mean | 0.9 | 13.9 | 2.2 | 9.2 |

TABLE 3-continued

Results from the DIRR Algorithm. These Values are the Mean
Distance, mm, from the Centroid Location Using the DIRR Alignment
to the Corresponding Centroids at Ground Truth

|  | Complete CT | | Incomplete Range Scan | |
| --- | --- | --- | --- | --- |
|  | DIRR Success | DIRR Failure | DIRR Success | DIRR Failure |
| Deformation 2 | | | | |
| Trials | 1000 | 0 | 972 | 28 |
| Tumor 1 | 1.4 | N/A | 4.1 | 22.9 |
| Tumor 2 | 1.2 | N/A | 3.5 | 16.4 |
| Tumor 3 | 1.3 | N/A | 2.4 | 10.8 |
| Tumor 4 | 1.8 | N/A | 3.9 | 7.7 |
| Tumor 5 | 1.4 | N/A | 2.2 | 11.1 |
| Tumor 6 | 1.9 | N/A | 3.2 | 7.0 |
| Mean | 1.5 | N/A | 3.2 | 12.7 |

B. Finite Element Modeling Experiments: The two material properties that describe a linearly elastic surface are Young's modulus, E, and Poisson's ratio, v. Both properties were varied to determine their effect on the model. Young's modulus did not affect the model while varying it between 30 and 400 kPa. This material property would have an impact if there was heterogeneity in the model, such as incorporating different material properties for stiff tumors. When varying Poisson's ratio between 0.3 and 0.495, the model did exhibit some change. The RMS distance between boundary nodes was 0.7 mm over the range of parameter values, with some individual nodes moving as much as 8.0 mm between solutions. The largest movement in the subsurface targets was 0.5 mm. Although varying the properties did not significantly affect these modeling studies, it could play a larger role as the model becomes more advanced.

Figure 20:
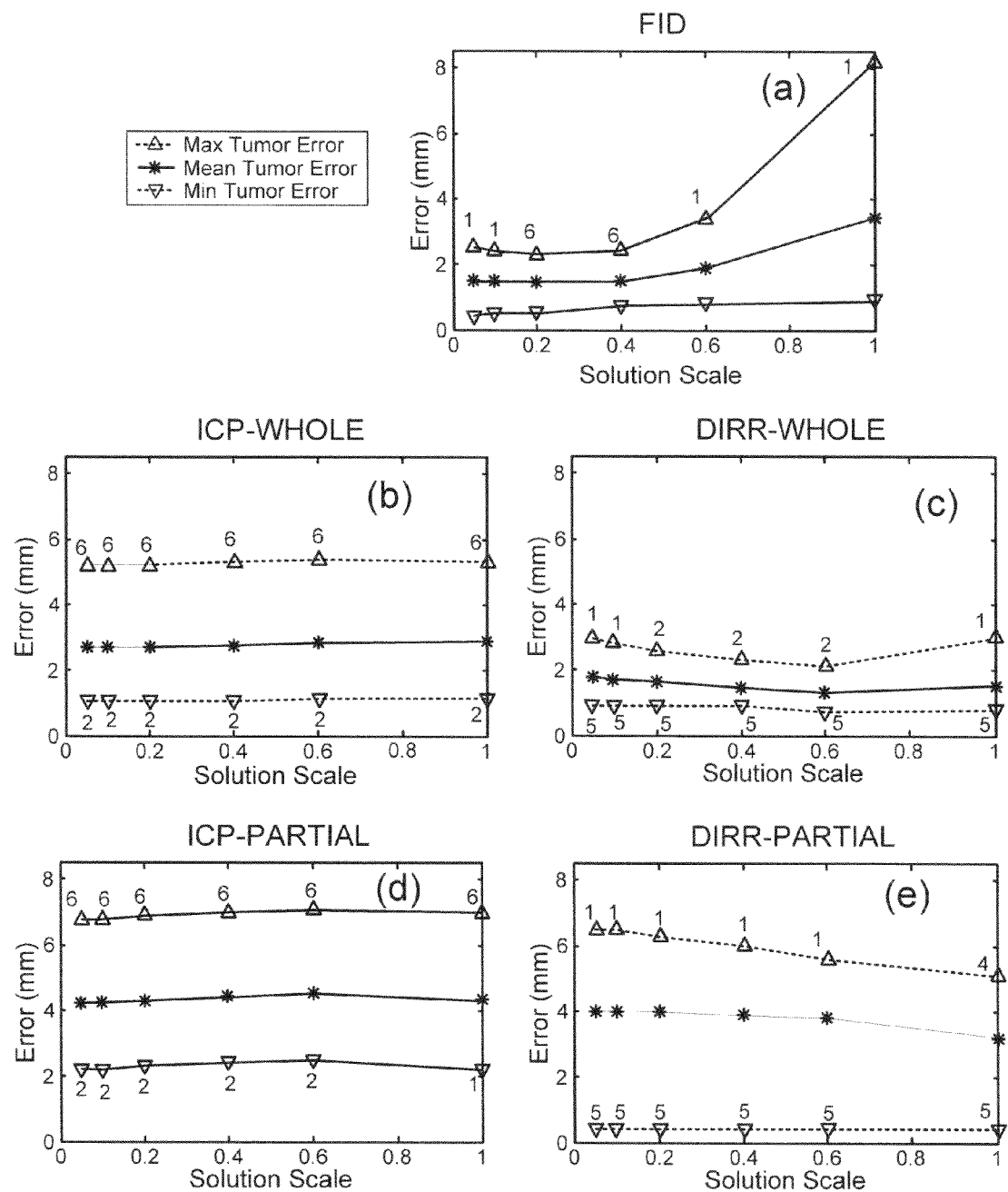
FIG. 20 shows tumor error after modeling the first deformation case with varying solution scale. The mean error is plotted along with the minimum and maximum errors labeled with the tumor number from FIG. 16 where they occurred.
Figure 22:
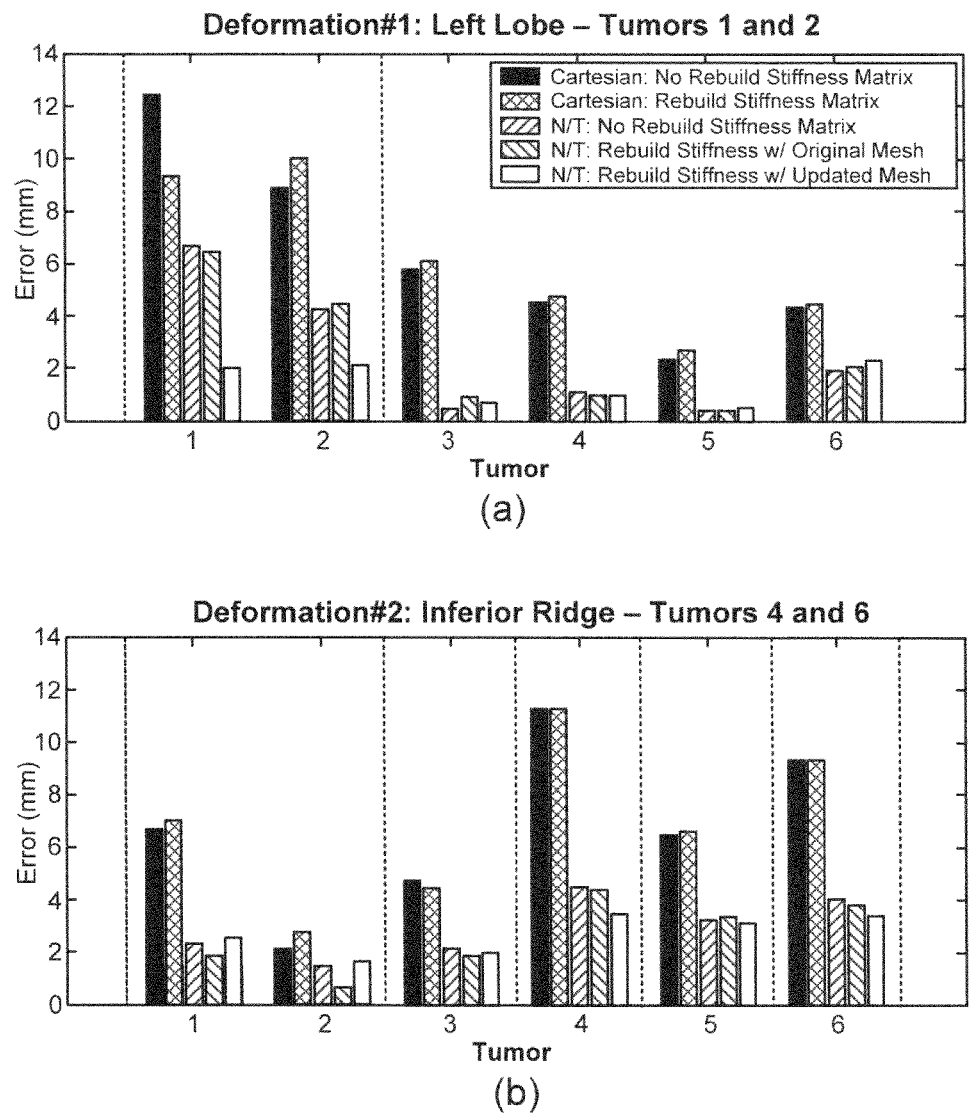
FIG. 22 shows tumor errors from FEM model while varying implementation of boundary conditions and the construction method of the preconditioner and stiffness matrix. The initial rigid alignment used here was based on the external fiducials.

The solution scale, $\alpha$, of equation (15), is a constant that represents the fraction of the closest point distance used for the boundary condition values. Before every increment, the updated closest point distance is calculated for each node and then scaled by this constant. The incremental FEM model was tested with six different values for the solution scale constant, ranging from 0.05 to 1.0. FIG. 20 shows the effects of the solution scale on the model for the first deformation case when aligning the intraoperative range scan data with each of the initial rigid alignments listed in Table 2 on the intraoperative data. In the second deformation set, varying the solution scale produced no significant effect on the model. The relationship between solution scale and the number of increments is shown in Table 4. To better understand the effects of the approaches highlighted in Table 4 with respect to individual targets, FIG. 21 reports target error associated with each mock tumor shown in FIG. 14 (a solution scale of 0.2 was used for all results shown). The next set of experiments focused on the implementations of the boundary conditions and the stiffness matrix. While holding the solution scale fixed at 0.2 and using an initial alignment based on fiducials or ICP, the model was run, testing the normal-tangential description of boundary conditions against the cartesian boundary conditions. For both of these implementations, the model was tested using both a moving grid and a static grid. For the normal-tangential method, an additional test was performed to use the original static mesh, but to use updated closest points and normals. Ultimately, this requires rebuilding of the stiffness matrix with each increment. The results are shown in FIG. 22 (where the FID alignment was used) and FIG. 23 (ICP-PARTIAL alignment).

TABLE 4

Relationship of the Solution Scale
with the Number of FEM Increments

| Data Set | Registration | 0.05 | 0.1 | 0.2 | 0.4 | 0.6 | 1.0 |
| --- | --- | --- | --- | --- | --- | --- | --- |
| Deformation 1 | FID | 52 | 27 | 14 | 8 | 5 | 1 |
|  | ICP-WHOLE | 27 | 14 | 8 | 5 | 4 | 1 |
|  | ICP-PARTIAL | 29 | 15 | 9 | 5 | 4 | 1 |
|  | DIRR-WHOLE | 45 | 23 | 12 | 7 | 5 | 1 |
|  | DIRR-PARTIAL | 44 | 23 | 12 | 7 | 5 | 1 |
| Deformation 2 | FID | 41 | 21 | 11 | 6 | 5 | 1 |
|  | ICP-WHOLE | 13 | 7 | 5 | 4 | 3 | 1 |
|  | ICP-PARTIAL | 12 | 7 | 5 | 3 | 3 | 1 |
|  | DIRR-WHOLE | 16 | 9 | 6 | 4 | 3 | 1 |
|  | DIRR-PARTIAL | 18 | 10 | 6 | 4 | 3 | 1 |

It is important to understand how the various components of the MUIGLS approach affect the localization of tumors.

Table 5 summarizes the effects of both registration and finite element modeling on target accuracy. The finite element modeling results come from the best scenario, where normal-tangential boundary conditions are used on a moving grid. In the column for the ICP-WHOLE alignment, the first deformation case yields a difference in the mean error when comparing the before and after model application. When employing the DIRR-WHOLE method, a more marked reduction occurs in the regions where the greatest amount of shift has occurred (tumors 1 and 2), as it has been identified by the DIRR. There are still improvements in the second deformation case, where the deformation is less significant.

TABLE 5

Improvement of Tumor Error, MM, as a Result of Finite Element Modeling

| Tumor | ICP WHOLE | | DIRR WHOLE | | ICP PARTIAL | | DIRR PARTIAL | |
| --- | --- | --- | --- | --- | --- | --- | --- | --- |
|  | Before Model | After Model | Before Model | After Model | Before Model | After Model | Before Model | After Model |
| (a) Deformation 1 | | | | | | | | |
| 1 | 6.6 | 1.9 | 32.6 | 2.5 | 7.0 | 2.8 | 33.3 | 5.6 |
| 2 | 4.9 | 1.0 | 21.3 | 2.6 | 6.8 | 2.3 | 22.0 | 4.2 |
| 3 | 8.0 | 3.9 | 2.0 | 1.4 | 8.4 | 5.5 | 4.2 | 3.1 |
| 4 | 6.3 | 1.7 | 1.6 | 1.3 | 8.1 | 3.5 | 6.5 | 5.3 |
| 5 | 2.5 | 2.3 | 1.2 | 0.9 | 5.4 | 4.9 | 0.6 | 0.4 |
| 6 | 6.0 | 5.2 | 0.6 | 1.2 | 8.0 | 6.9 | 3.9 | 4.2 |
| Mean | 5.7 | 2.7 | 9.9 | 1.7 | 7.3 | 4.3 | 11.8 | 3.8 |
| (b) Deformation 2 | | | | | | | | |
| 1 | 2.9 | 2.1 | 1.9 | 1.9 | 3.5 | 3.1 | 3.3 | 2.9 |
| 2 | 1.8 | 1.3 | 1.6 | 1.0 | 2.0 | 1.2 | 1.6 | 1.1 |

TABLE 5-continued

Improvement of Tumor Error, MM, as a Result of Finite Element Modeling

| Tumor | ICP WHOLE | | DIRR WHOLE | | ICP PARTIAL | | DIRR PARTIAL | |
|---|---|---|---|---|---|---|---|---|
| | Before Model | After Model | Before Model | After Model | Before Model | After Model | Before Model | After Model |
| 3 | 1.3 | 1.5 | 1.7 | 1.2 | 1.9 | 1.4 | 1.2 | 1.2 |
| 4 | 4.3 | 3.5 | 4.6 | 3.6 | 5.3 | 5.3 | 4.2 | 3.8 |
| 5 | 3.8 | 3.5 | 2.8 | 2.3 | 4.1 | 4.5 | 3.3 | 1.4 |
| 6 | 4.2 | 3.0 | 5.8 | 3.6 | 6.1 | 5.5 | 6.8 | 4.0 |
| Mean | 3.0 | 2.5 | 3.0 | 2.3 | 3.8 | 3.5 | 3.4 | 2.4 |

Discussion

A. Deformation Identifying Rigid Registration: The most common form of determining correspondence is based on the closest point distance operator. For most surfaces and correspondence strategies, closest point distances are used as initial estimates of correspondence, allowing the iterative alignment of images to naturally bring points to their true one-to-one correspondence. With the presence of deformation, the closest point operator becomes less reliable as a means of determining correspondence. Many groups have proposed modifications to the closest point operator in order to achieve a more accurate correspondence estimate [42, 75-79].

Establishing correspondence with a closest point distance can be inaccurate when a large deformation is present. Rather than establish correspondence, the DIRR algorithm computes the signed distance to the underlying target surface, often represented by RBFs. The signed distance values are used to drive the Gaussian term in the cost function (2), which rewards transformations where there are many points with small signed distances. When the cost function is at a maximum, it is associated with minimally deformed regions that are well-aligned. At the same time, the cost function does not penalize large signed distances associated with deformation.

The DIRR algorithm performs better when given a complete representation of the deformed surface. When perturbing each of the fiducials in the deformed set by 1 cm, there was only one failure in 1000 trials for the first deformation case while there were no failures for the second case. Both sets of trials came within 2 mm from the ground truth alignment. The partial surfaces from range scan surface data reach a successful alignment 90% of the time or greater. One strategy to improve success could be to use a priori information regarding the extent of deformation. Similar to the manually delineated deformation results, this information could be incorporated into DIRR semiautomatically, by manually classifying regions of the surface according to the confidence that deformation is or is not taking place. This confidence measure could be used to weight each point in the cost function accordingly.

Other sources of error regarding the DIRR include inaccuracies due to surface acquisition. These errors more than likely arise from range data acquisition and to a lesser extent the surface extracted from the segmentation of the tomograms. A discussion on the sources of error in range scans and how they pertain to image-guided surgery can be found in [36]. While the surface fit using the RBF data gets rid of some of the input noise, detail is lost as well. There is also the possibility that small regions of deformation (1-3 mm) are not being accounted for in either the partial ICP or DIRR algorithms, which is not in the scope of this study.

B. Modeling Considerations: In most cases, the FEM model provides significant improvement over results from rigid registrations alone, as indicated by Table 5. The largest improvement in accuracy comes from rotating the boundary nodes into a normal-tangential coordinate system. By implementing mixed boundary conditions, which allow the nodes to move along the plane tangent to the surface, the results suggest that organ shift is better accommodated. When using the Cartesian boundary conditions, the lack of interaction is observed by a distinct delineation where a transition of boundary condition types occurs, which is illustrated in FIG. 24. Specifying the displacement in the direction of the normal is intuitive if one were to examine the deformation from these experiments as a series of small increments. At every increment, the actual displacement should closely align with surface normals. Allowing the node to freely move in the tangential direction resolves any discrepancies between the true direction of deformation and the one specified by the surface normal. However, unlike these phantom experiments, there might be a situation in which the deformation is not in the direction of the normals for the acquired intraoperative surface. At this point, the DIRR becomes more important. By identifying the deformation through the rigid registration, it would be possible to determine the vector that describes the orientation of the deformation with respect to the finite element mesh which could then serve in place of the mesh's surface normal.

Due to the incomplete nature of the intraoperative data acquisition, the initial rigid alignment used to set up the closest point boundary conditions also plays a significant role. In both deformation cases, the transformation obtained from the DIRRWHOLE alignment provided very good results. However, when using an incomplete surface in the DIRR-PARTIAL alignment, small misalignments arise, especially rotations that were not recovered by the model and led to larger inaccuracies. The rigid fiducials from the images also provided good results, although the errors were lower in the first case, since there was little difference between the resulting registration and the one determined using DIRR. In both cases, the ICP algorithm did not perform as accurately as other alignments, since the alignment misregisters minimally deformed surfaces and eliminates the meaning of holding these areas fixed in the boundary conditions.

Given the time sensitive nature in the operating room and the significant costs that can be associated with running the finite element model numerous times, the selection of parameters for this model must focus on limiting the number of increments while maximizing the accuracy. One of the quickest ways to limit the computational intensity is to keep the solution scale as high as possible, i.e., large increments. The incremental approach has the greatest effect when geometric nonlinearities are more significant. In the first deformation case, there was a significant effect with the FID alignment, where the model must resolve the rigid registration between FIGS. 19a and 19c in addition to the large shift, which is on the order of 3 cm in some areas. There are limited effects from the solution scale for ICP-WHOLE, ICP-PARTIAL, and DIRR-WHOLE, since there is less shift to resolve. In each of these three alignments, the lowest mean tumor error occurred at a solution scale less than 1. While the mean tumor error for these alignments varied less than 0.5 mm over the full range of solution scale values, there were some instances of individual tumor errors improving 1-2 mm. Finally, there were adverse effects for the DIRR-PARTIAL alignment. In this case, as mentioned above, there was a slight misalignment, which compounded with the incremental approach. The solution scale had very little effect on the smaller deformations observed in the second deformation case, as there are less issues with determining correspondence.

Another way to reduce computation time is to eliminate the steps where the stiffness matrix was rebuilt. From the results of FIG. 22, there was a decrease in targeting accuracy when implementing this time-saving tactic, mainly at the tumors where the most shift was present. The error was also higher when using a static grid and rebuilding the stiffness matrix with updated surface normals to preserve mesh quality. However, when aligning the surface with ICP, these measures became more effective.

Since the model is primarily driven by intraoperative data, the method by which boundary conditions are chosen for each node can play a significant role in the resulting accuracy. If nodes that are specified to have closest point boundary conditions are located where there is minimal coverage provided by intraoperative data, inaccurate values for boundary conditions could result. One way to limit these inaccuracies is to use RBF fitting to construct a distance map associated with the intraoperative data, providing a more complete representation of the data and accurate closest point distance calculations for the boundary conditions at the cost of greater pre-processing time. In this example, it is determined if the deformation could be identified and corrected from partial surface data alone, which has the capability to acquire sub-surface information intraoperatively using coregistered ultrasound [75], which could improve the accuracy of this method.

Considering the numerous amount of nonrigid registration algorithms available, it might seem more intuitive to implement one of these methods instead. In fact, deformable algorithms that use feature and geometric information are being considered in future studies as a means of comparison. The main challenge that arises with many of these methods is how to deform the preoperative mesh in regions where there is no intraoperative data present to provide corresponding features to drive the nonrigid algorithm. Using fixed boundary conditions to hold these regions immobile does not accurately represent the deformation that is occurring in the operating room. In fact, most of the boundary on the underside of the phantom or the liver is allowed to deform and is prescribed stress-free boundary conditions. This method appears to be more intuitive than to modify a nonrigid transformation to simulate stress-free boundary conditions in areas where the intraoperative data is incomplete.

Arguably though, the advantage of FEM-based compensation is that the deformation behavior can be grounded within an analysis of the continuum as relayed within a partial differential equation describing elastic mechanics. As a result, compensation is based on the physics of deformation rather than a process of polynomial interpolation. While it is true that polynomial basis functions are often at the core of FEM, the process of prescribing the correct boundary conditions for modeling deformation has a distinct link to physical quantities such as displacement, strain, force, and stress.

C. The Role of Surface Coverage: The incomplete surface data seems to provide the largest challenge for developing the model-updated framework. If the partial coverage of the range scanner is uneven and does not capture enough points over the minimally deformed region, then the cost function (2) will result in values different from those acquired with a complete, uniformly sampled description, as obtained from the CT data. This uneven coverage could lead to a shift in the location of the desired minimum. As a result, this alignment could have inaccuracies with regards to identifying deformation and establishing accurate correspondence. The same effect is also observed when using only the minimally deformed regions of the partial range scan surface in an ICP registration.

In the first deformation case, the DIRR-PARTIAL algorithm results in a slight rotation normal to the deformation in the first case. This rotation places the ridge of the intraoperative data over the wrong area of the surface. As a result, the correspondences are incorrect and improper values are used for the boundary conditions, leading to higher inaccuracies than other initial alignments. The second deformation case shows another challenge regarding intraoperative data acquisition that involves accurately capturing the deformation. Both range scans were acquired from the top view of the phantom, while much of the deformation in the second case is occurring at the inferior ridge. If range scan data would have been more focused on the site of deformation, the algorithms would have performed better.

While partial surface data can have a significant effect on identifying and subsequently correcting for deformation, the uneven coverage is a more important issue. Simulated range scans were created by taking the CT data from deformed sets and eliminating the points representing the bottom region of the phantom. Initial studies using these data sets show good convergence with the DIRR. For the first deformation case, a successful registration, as defined in Section II, was 99.6% over 1000 trials using the simulated range scans, and 96.5% for the second case. Both data sets were closer to the results provided by the complete CT sets than the range scan surfaces. This data can be used in the future to determine the effects of coverage on the DIRR and deformable models.

Among other things, the present invention recites a method for identifying and compensating shift using only surface data. The goal of the DIRR was to provide the same rigid registration that would occur if only the minimally deformed regions of the surface were used. The DIRR accomplished this objective to within 2 mm when using a complete description of a deformed surface and 4 mm for a partial surface. The finite element model resulted in improvements over the rigid registration when closest point boundary conditions were represented in a normal-tangential framework. The incremental approach had a modest effect for cases of large deformations. The model achieved the best accuracies when initial alignments were provided from complete descriptions of the deformed surface (ICP-WHOLE, DIRR-WHOLE). However, the FEM also performed better when aligned using DIRR compared to ICP alignment for both representations of the deformed surface (complete CT and partial range scan).

Example 3

Robust Surface Registration Using Salient Anatomical Features—a Patch Approach

This example relates to how to implement a surface based registration method that utilizes the homologous, salient anatomical features to ensure convergence to reasonable solutions under conditions of poor initial alignment. Additionally, the robustness and feasibility of the implemented algorithm are demonstrated, relative to the traditional ICP based method, using both phantom and clinical data.

Method

A. Overview: The implemented weighted patch ICP algorithm in this embodiment is effectively a novel, non-obvious extension of the WGF algorithm proposed by Maurer et al. The homologous anatomical features, or patches, will be used to both bias point correspondence determination as well as play a more significant role in the PBR performed at each iteration of the algorithm. The weighting scheme used to bias the PBR is dynamic over the course of the algorithm where the homologous patch regions play an overwhelming role early in the registration process to ensure the patches are initially aligned and a more supportive role at later iterations in the algorithm.

For the following explanation, let $S=\{s_m\}$ for $m=1,\ldots,N_S$ be the source point set and $T=\{t_n\}$ for $n=1,\ldots,N_T$ be the target point set. Assume that the point sets S and T each contain a single set of patch points that describe a homologous anatomical feature used to drive the registration. Further, let $\{p^S_m\}$ and $\{p^T_n\}$ be binary arrays, where an array value of 0 describes the non-patch point indices and a value of 1 describes the patch point indices. Let $\{w_m\}$ be a set of weights where $w_m=1$ for $p^S_m=0$ and $w_m=W_{PBR}$, a dynamic weighting factor used to bias the PBR at each iteration, for $p^S_m=1$.

B. Point Correspondence Determination: In order to bias the point correspondence determination for the patch point sets, a weighting factor, $w_{PC}$, is introduced, where $0<w_{PC}\ll 1$. The weighting factor is used to bias the closest point operator, Cm, by significantly decreasing the Euclidian distances (d) between patch point pairs via the following relationship:

$$d_{m,n} = \begin{cases} w_{PC}\|s_m - t_n\| & \text{if } p^S_m = p^T_n = 1 \\ \|s_m - t_n\| & \text{otherwise} \end{cases} \quad (17)$$

Figure 25:
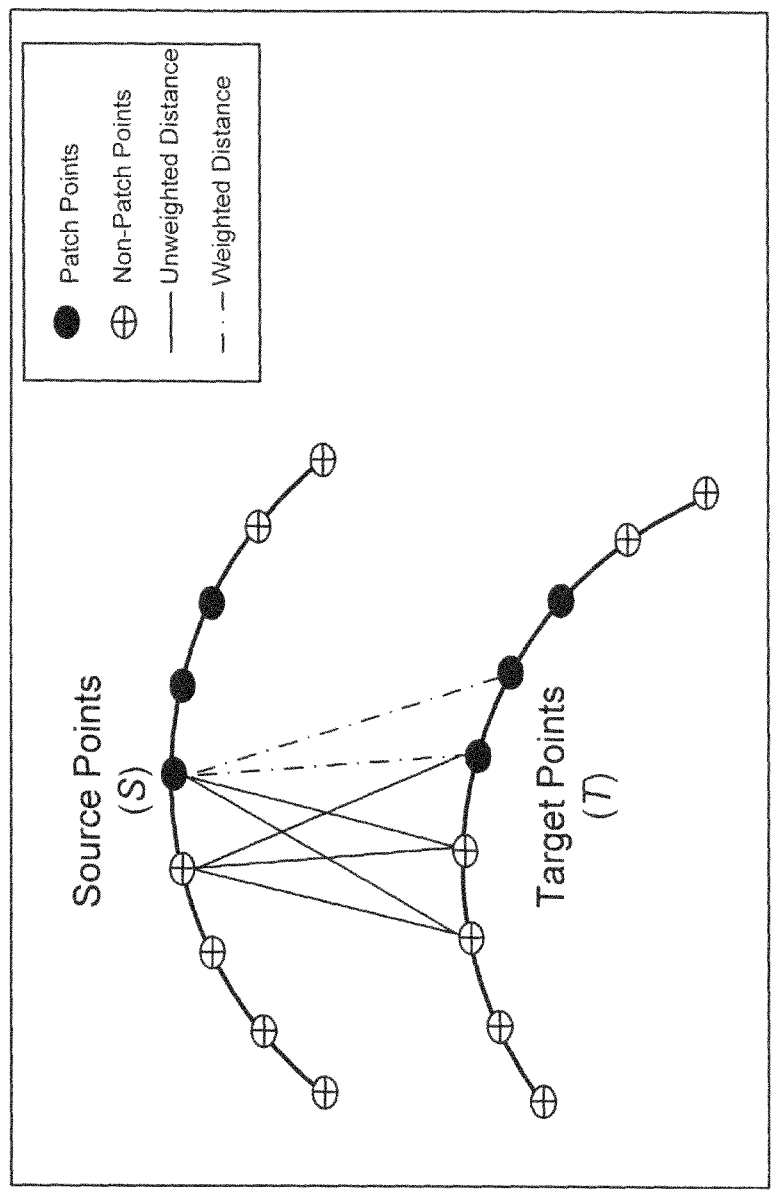
FIG. 25 shows a graphical depiction of the weighted point correspondence method. Only the Euclidean distances computed from source patch point to target patch point are biased by the weighting factor $w_{PC}$ (i.e., dashed lines). The point correspondence determination for non-patch points is not effected by the weighting (i.e., solid lines).

In other words, Euclidean distances identified as being between source and target patch points are multiplied by the fractional weighting factor ($w_{PC}$). Since the weighting factor is presumably, a very small fraction, the corresponding point found for a source patch point will primarily be contained within the target patch point set. FIG. 25 shows a pictorial representation of the weighted point correspondence method. Biasing the point correspondence determination alone, however, will not be enough to facilitate a robust surface alignment under conditions of poor initial pose and soft tissue deformation. As described in the next section, biasing the rigid PBR performed at each iteration will provide increased robustness according to this embodiment of the present invention.

C. Weighted Point Based Registration: Once point correspondence has been determined, the weighted rigid PBR method described by Maurer et al. [59] is implemented. This method seeks to find the rigid-body transformation ($\Omega$) that minimizes the following objective function ($f$):

$$f(\Omega) = \sqrt{\sum_{m=1}^{N_M} w_m \|C_m(s_m, T) - \Omega(s_m)\|^2} \quad (18)$$

where $\{w_m\}$ is a set of weights letting $w_m=1$ for $p^S_m=0$ and $w_m=W_{PBR}$, where $W_{PBR}\geq 1$, for $p^S_m=1$. The weighting factor ($W_{PBR}$) serves to increase the role of the patch points within the determination of the transformation, $\Omega$. A closed form solution for the special case of $w_m=1/N_m$ for $m=1,\ldots,N_m$ has been presented by Arun et. al. [70]. The solution is based on the singular value decomposition of the covariance matrix of the position vectors in the two spaces. The closed form solution presented by Maurer et al., which is valid for all $w_m>0$ is an extension of the aforementioned solution.

In the WGF algorithm presented by Maurer et al. [59], the weights used within the PBR for the geometrical features used in the registration (i.e. $W_{PBR}$) remain constant throughout the registration process. This implementation is modified by creating a dynamic scheme by which the patch point weight, $W_{PBR}$, is dynamic as the algorithm progresses.

D. Dynamic Weighting Scheme: Being that FLE and soft tissue deformation, the initial alignment provided by the anatomical fiducial based PBR can be quite poor. In order to circumvent incorrect, local minima convergence issues, the alignment of the homologous patch is made to play a very strong role early in the weighted patch ICP algorithm. However, due to segmentation inaccuracies and the fact that a one-to-one correspondence between source and target patch regions most likely will not exist, it is important that the bias in the PBR towards the patch regions to be less significant as the registration continues. In other words, since patch region identified in the source data will not likely contain the entire target patch point set and by biasing the registration too heavily throughout the registration process could lead to convergence to an incorrect local minima. In order to circumvent these problems, the remainder of the surface data is allowed to play a more significant role as the registration proceeds. By employing this dynamic weighting, the patch regions serve as an anchor at later iterations within the algorithm such that deformation will not cause a divergence in the final registration result. The following equation describes the behavior of the dynamic weighting scheme, where $W_{PBR}$ is described as a function of iteration (i, i$\geq$1):

$$W_{PBR}(i)=W_{PBR,base}+ \lfloor W_{PBR,max}-W_{PBR,base}\rfloor\exp[-\alpha(i-1)] \quad (19)$$

Figure 26:
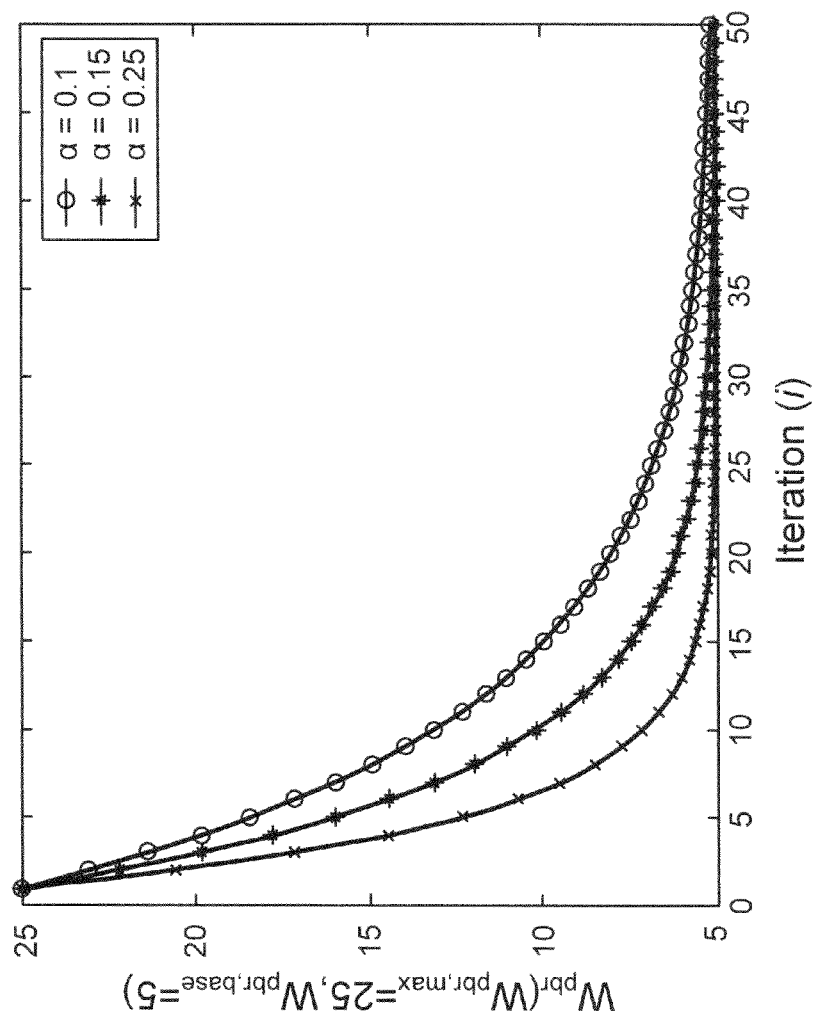
FIG. 26 shows plots of dynamic PBR weighting factor function with various relaxation parameter ($\alpha$) values. Decreasing the value of $\alpha$ increases the length of time that the patch region dominates the PBR at each iteration. As the value of $\alpha$ approaches to zero the PBR weighting scheme becomes more akin to that proposed by Maurer et al. [59].

In the above equation, $W_{PBR}$, max is the maximum patch PBR weight factor and corresponds to the patch weight at the very first iteration of the algorithm. The weight factor $W_{PBR}$ approaches $W_{PBR,base}$, the baseline patch weight where $W_{PBR,max}\geq W_{PBR,max}\geq 1$, as i becomes significantly large. The rate at which $W_{PBR}$ approaches $W_{PBR,max}$ is determined by the relaxation constant $\alpha$, where $\alpha\epsilon[0, 1]$. A graphical representation of Equation (19) and the effects of the relaxation constation $\alpha$ are graphically described in FIG. 26.

E. Validation: Quantitative robustness experiments and qualitative visual assessments were performed using both phantom and clinical data were performed to compare the proposed weighted patch ICP algorithm with a traditional ICP implementation.

Figure 27:
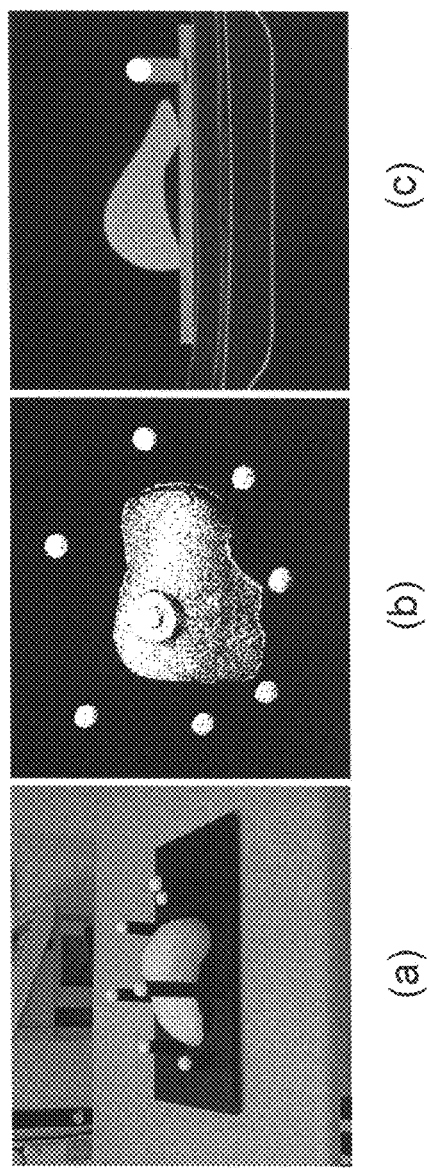
FIG. 27 shows digital photograph (a), raw LRS scan (b) and sample CT slice (c) of imaging phantom. The silicon liver model, located in the center of the phantom, is surrounded by a set of seven white Teflon spheres. These spheres, which can be localized in both LRS and CT image spaces, are used in the determination of the "gold standard" ICP registration and serve as targets in the robustness studies.
Figure 28:
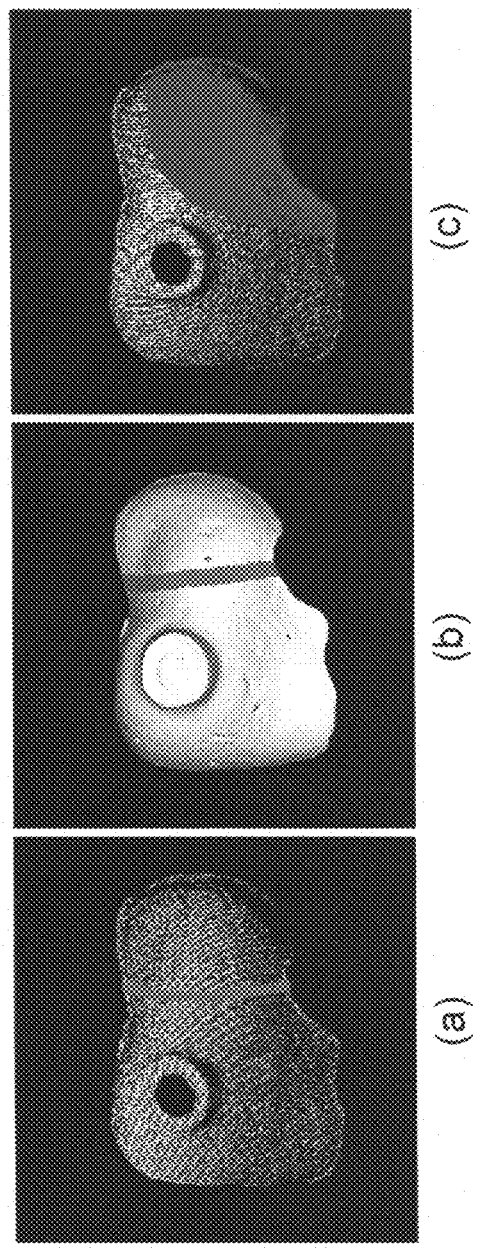
FIG. 28 shows phantom LRS simulated falciform patch selected from full scan (a) was used to delineate the homologous region in the CT image surface (b). To more accurately simulate the typical LRS surface field of view obtained during surgery, a subregion of the LRS was manually selected for use in the robustness trials.
Figure 30:
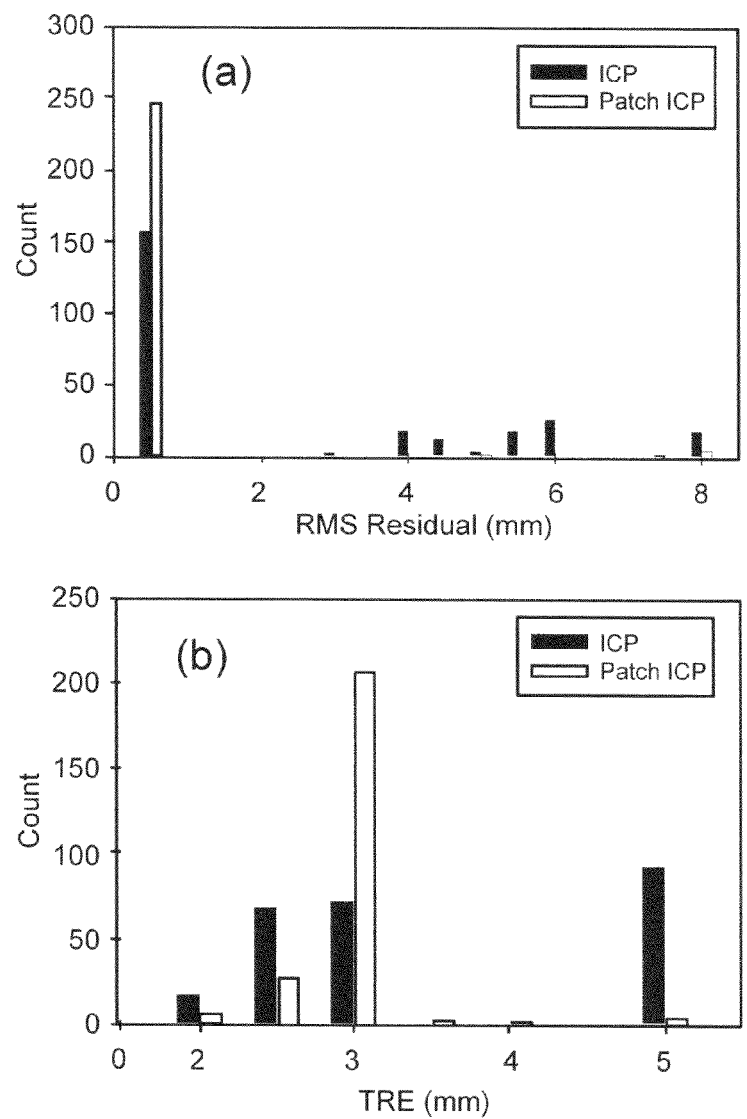
FIG. 30 shows histogram representations of the RMS residual (a) and TRE (b) results from the phantom robustness trials. Note that for these trials the "gold standard" RMS residual and TRE values were found to be 0.621 mm and 2.31 mm, respectively. Note the far greater number of ICP RMS residual results that fell >2 mm and TRE results that were >5 mm as compared to the weighted patch ICP results.

F. Phantom Experiments: In order to quantitatively compare the developed weighted patch ICP algorithm with the traditional ICP method, the imaging phantom shown in FIG. 27 was constructed. Poly (dimethyl) siloxane (rubber silicone) was used to fabricate a liver model. The liver model was surrounded by seven Teflon spheres (Small Parts Inc., Miami Lakes, Fla.), imageable using both CT and LRS modalities. The sphere points were localized in the LRS scan using a least squares sphere fitting method described by Ahn et. al. and served as point based fiducials for determining the "gold standard" ICP registration and targets for the robustness experiments. Once the fiducials and surfaces were extracted from both CT and LRS images, a PBR was computed using the seven sphere fiducial points. This PBR served as an initial alignment registration from which the "gold standard" ICP registration was computed using the entire LRS surface. A simulated falciform patch region was manually selected from the full LRS data as shown in FIG. 30. The "gold standard" ICP registration was then used to extract the analogous region on the CT image surface of the liver phantom. The CT image falciform region contained all the points within a 3 mm radius of each of the LRS surface falciform points. This was done to simulate segmentation errors in accurately delineating the homologous patch region on the image surface (shown in FIG. 28). Additionally, only a sub region of the LRS data was used in the robustness studies since the LRS scans acquired intraoperatively very rarely contain the amount of surface information shown in the complete LRS scan. The region was selected based on the inventors' experience of the most scanned regions during the observed surgical procedures (shown in FIG. 28). The number of points contained within the CT image liver surface and simulated falicform region were 106,661 and 2,936, respectively. The number of points contained within the full and partial liver LRS scans was 34,546 and 12,367 with 1,125 and 802 falciform points in each of the respect full and partial scans.

The robustness trials involved perturbing the LRS data from the "gold standard" ICP alignment with a random six degree-of-freedom, rigid-body transformation to simulate a variety of initial alignments. The transformations were computed by generating a set of six random parameters (three translation and three rotation). The rotation parameters ($\theta^x$, $\theta^y$, $\theta^z$) were generated by a uniformly distributed random number generator and set to obtain values between −45° and 45°. The translation parameters ($t^x$, $t^y$, $t^z$) were also generated using a uniformly distributed random number generator and set to obtain values between −50 mm and 50 mm. The robustness trials were run over 250 perturbations per registration method and the data compared in terms of sphere target registration errors (TRE) and surface RMS residuals.

The parameters used for the ICP implementation for these trials were a maximum iteration number of 1000 and convergence criterion of 1e$^{-4}$ mm RMS residual difference between iterations. The parameters used for the weighted patch ICP registration were as follows: 1000 maximum iterations, $W_{PBR,max}$=150, $W_{PBR,base}$=25, $w_{PC}$=1e$^{-4}$, $\alpha$=0.01, and a convergence criterion of 1e$^{-4}$ mm RMS residual difference between iterations.

G: Clinical Examples: Three sets of clinical data obtained from liver resections performed at Barnes-Jewish Hospital in St. Louis, Mo. were used for this portion of the validation experiments. The first two sets of patient data were used to visually determine the effectiveness of the proposed patch ICP registration algorithm. In each of theses cases, poor initial alignment conditions and significant soft tissue deformation let to incorrect ICP alignments. A third set of clinical data for a Patient 3 was used to perform robustness tests similar to those described for the phantom experiments. The ICP registration for the third set of clinical data was determined as a successful registration based on visual alignment evaluation, as shown in FIG. 29. For all the clinical registrations, the same parameters (outlined previously) were used for both the ICP and weighted patch ICP registration algorithms. Additionally, the same robustness study parameters were used for the perturbation transformations. The robustness data is reported in terms the RMS residual relative to the "gold standard" ICP registration.

Results

A: Phantom Experiments: The PBR calculated between the CT and LRS sphere point sets yielded an FRE of 1.358 mm. The "gold standard" ICP registration based off this PBR gave a TRE of 2.31 mm and an RMS residual of 0.612 mm. The histogram results for the 250 perturbation trials with respect to both RMS residual and sphere TRE values are shown in FIG. 30. The mean RMS residual over all trials was found to be 2.58±2.81 mm for the ICP trials and 0.856±1.60 mm for the patch ICP trials. The mean TRE values were found to be 57.32±76.54 mm for the ICP trials and 8.093±37.14 mm. Based on the TRE distributions, the trials that resulted in TRE values of >5 mm were considered failed registrations (the mean TRE values >5 mm for the ICP trials was found to be 149.68±46.102 mm and 267.10±17.952 mm). Given this criterion, it was found that the traditional ICP registration provided an incorrect registration in 93 of the 250 trials, which the patch ICP algorithm failed on only 5 trials.

B: Clinical Examples: The qualitative clinical results for patients 1 and 2 are shown in FIGS. 31 and 32, respectively. For both data sets, the patch ICP registration provides a much more reasonable alignment. Most noticeably, for patient 1, as shown in FIG. 31 the ICP registration resulted in a gross misalignment of the surfaces where the LRS scan of the anterior liver surface was aligned with the posterior surface. The improvement in the surface alignment provided by the weighted patch ICP algorithm is also visible in FIG. 32. Specifically, the alignment near the umbilical fissure is significantly improved relative to the ICP registration result.

Additionally, the robustness results, shown in FIG. 33, provide further evidence of the increased robustness of the proposed method. While the final RMS residual between the two surfaces is not the most objective measure of registration accuracy, it is highly unlikely that registrations that result in large RMS residuals correspond with reasonable alignments. While it is possible that incorrect alignments may still provide small RMS residuals, based on the data provided it is reasonable to conclude that the proposed algorithm is much more robust to different initial poses based on the fact that only a single registration out of the 250 trials resulted in a RMS residual significantly larger than the baseline ICP registration.

Discussion

The preliminary data presented from both the phantom and clinical studies provide strong evidence that the invented weighted patch ICP algorithm is more robust to poor initial alignment than the traditional ICP method. Additionally, the patch ICP registration algorithm provided much improved registrations for two of the sets of clinical data where the traditional ICP method resulted in large misalignments.

One of the primary advantages of the disclosed algorithm is the use of the dynamic PBR weighting scheme described by Equation (19). This dynamic weight factor allows for the registration to be significantly biased towards patch alignment at early iterations, while utilizing this patch alignment as an anchor at later iterations. By lowering the PBR weight factor of the patch points at later iterations the remaining surface information is utilized to provide a more unbiased alignment of the surfaces. Additionally, the dynamic weighting scheme also compensates for segmentation errors in the delineation of exactly homologous patch regions. Since the non-patch regions of the surfaces play a more significant role later in the registration process, the registration is given the opportunity to refine to a more globally correct alignment. Based on the current implementation, more favorable results can be facilitated by being a little more conservative in the segmentation of the LRS anatomical patches which being a bit more liberal in the preoperative anatomical feature delineation. As long as homologous target patch points exist for all source patch points (the opposite does not have to be true), the current implementation will not cause a bias towards an incorrect registration.

Another favorable quality of the disclosed method is the ease at which the method could be incorporated into current IGLS procedures. The additional time required to delineate the pertinent anatomical features from either LRS data or via digitization with a tracked probe would represent only a modest increase in the amount of time required to perform the surface based registrations during surgery. Additionally, implementing the algorithm with K-d-trees to perform the closest point searches allows the algorithm to nearly as fast as a traditional ICP registration. Preliminary results suggest that increase in time required to perform the weighted patch ICP registration is modest in comparison to the traditional approach.

While the preliminary data is promising, a number of caveats exist with the proposed algorithm in its current form. In contrast to the ease of accurately delineating the falciform region within the LRS data, the ability to accurately segment the falciform region, based on the surface groove, is highly dependant on patient anatomy, image quality, and the quality of segmentation. Additionally, the current implementation is not robust to outlier points which significantly limit the effectiveness of the algorithm. Future work will be geared towards determining the optimal weighting parameters with respect to convergence and robustness as well as an exploration of the utility of the disclosed weighted patch ICP method to deformation compensation schemes.

Accordingly, the preliminary results of the disclosed weighted patch ICP algorithm suggest that this method is more robust to poor initial alignments than the traditional ICP based approach. Additionally, the incorporation of the disclosed algorithm would require little additional effort over the current technique. Future work may involve determining the optimal algorithm parameters with respect to convergence time and robustness. Additionally, the algorithm should be validated, relative to the ICP based method, with respect to providing relevant displacement data for model updating purposes.

Example 4

Image-Guided Liver Surgery: Concepts and Initial Clinical Experiences

Image guided surgery (IGS) provides navigational assistance to the surgeon by displaying surgical probe position on a set of preoperative tomograms in real-time. In this study, the feasibility of implementing IGS concepts into liver surgery was examined during eight hepatic resection procedures. Preoperative tomographic image data was acquired and processed. Accompanying intraoperative data on liver shape and position was obtained through optically tracked probes and laser range scanning technology. The preoperative and intraoperative representations of the liver surface were aligned using the Iterative Closest Point (ICP) surface matching algorithm. Surface registrations resulted in mean residual errors from 2-6 mm, with errors of target surface regions being below a stated goal of 1 cm. Issues affecting registration accuracy include liver motion due to respiration, the quality of the intraoperative surface data, and intraoperative organ deformation. Respiratory motion was quantified during the procedures as repeatably cyclical, primarily along the cranial-caudal direction. The resulting registrations were more robust and accurate when using laser range scanning to rapidly acquire thousands of points on the liver surface and when capturing unique geometric regions on the liver surface, such as the inferior edge. Finally, finite element models recovered much of the observed intraoperative deformation, further decreasing errors in the registration. Image-guided liver surgery has shown the potential to provide surgeons with important navigation aids that could increase the accuracy of targeting lesions and the number of patients eligible for surgical resection.

Materials and Methods

A. Image Acquisition and Segmentation: Preoperative image volumes were acquired by Computed Tomography (CT) or Magnetic Resonance (MR). Both modalities used tri-phase studies which produce an uncontrasted image volume, a volume with arterial phase contrast, and a third volume where the contrast has washed out of the arteries and provides more emphasis on the venous vasculature. This imaging protocol is standard for patients undergoing liver tumor resection. The pixel spacing for these images ranged from 0.6 to 1.0 mm. The preferred slice thickness was 2.0 mm, though in these studies, the acquired volumes ranged from 0.8-5.0 mm. Forth is study, it is highly desirable that the tomographic slices do not overlap.

From the resulting tomograms, the liver was segmented from the surrounding abdominal viscera. Two methods of segmentation were performed. The first involved the authors manually outlining the contour of the liver, which can take 4 hours or longer. To greatly reduce user interaction, the group has developed a semi-automatic method [31, 34] that is based on the level set technique [80]. This method was specifically designed to identify the edges of the liver, which can be difficult to discern near the ribs and heart. After segmentation is completed, there is a brief review and user interaction phase with the surgeon to further refine the segmentation. Corresponding results from an example manual and automatic segmentation of a CT slice are shown in FIG. 34. The segmented contours are used to generate a three-dimensional surface model using the marching cubes methods [34]. Further refinement is performed using surface fitting software (FastRBF Toolkit, Far Field Technology, Christchurch, NZ) involving radial basis functions (RBFs). This method provides a smoother representation with less points, as illustrated in FIG. 35.

B. Intraoperative Data: To digitize individual points in three-dimensional space, the OPTOTRAK3020 (Northern Digital, Waterloo, Ontario) optical localization system was used. The system consists of an infrared camera, which determines the position and orientation of specialized probes embedded with infrared diodes (IREDs). Points are digitized by placing them in contact with the probe tip. The OPTOTRAK system is capable of acquiring single points with a root mean square accuracy of 0.1 mm. Surface data is generated by sweeping the probe across the entire organ, allowing the tracking system to rapidly collect digitized points on the surface. For this study, the rate that position was updated was set to 40 Hz. FIG. 36 displays the OPTOTRAK system in use, acquiring points on the liver surface.

Dense surface representations were acquired intraoperatively with a commercially available laser range scanner (RealScan 200C, 3D Digital Corp, Bethel, Conn.).This method serves as a complimentary means to acquire surface data. The range scanner uses the principle of optical triangulation to rapidly capture thousands of three-dimensional points in a noncontact fashion. The laser used is very low power, a class I eye-safe laser, orders of magnitude below the Maximum Permissible Exposure level for skin as stated in the American National Standard for Safe Use of Lasers (ANSIZ136.1). FIG. 38 shows the range scanner acquiring data in the operating room. In addition to collecting three-dimensional surface data, the scanner simultaneously acquires a video image of the scene, and texture maps the appropriate color information onto each three-dimensional point. The texture mapped point data is extremely useful in identifying the exposed liver surface from the resulting range scans and segmenting them from the rest of the intraoperative scene. FIG. 2 shows the video image acquired by the scanner, along with the three-dimensional point cloud, and how this data is combined to form the texture mapped data.

To have relevance in the surgical suite, the output points of the range scanner must be reported in reference to the OPTOTRAK localization system. To that end, individual infrared diodes (IREDs) that are tracked by the OPTOTRAK camera are rigidly attached to the scanner. A calibration procedure was developed to link the position of the IREDs with the ranges canner system, and tracking studies were performed [32]. A more robust method of IRED placement on the range scanner was developed, allowing for tracking with sub-millimetric errors [35].

C. Rigid Registration: The surface of the liver has been chosen as the feature for registration. Intraoperative surface data is acquired using the range scanner or the tracked probe. This data is then registered with the surface model generated from the preoperative tomographic image volume using the Iterative Closest Point (ICP) method [14]. To make the searching process more efficient, k-d trees were used [34].

The ICP registration method can be susceptible to gross misalignment if a suitable initial estimate is not provided. Anatomical landmarks on or near the liver is identified and used to obtain an initial registration. Before the procedure, a set of four to five landmarks are identified in the image volume by the surgeon and their three-dimensional image coordinates are recorded. Typical land marks include the inferior tip of the liver, the lateral tip of the right lobe, the portal vein bifurcation, and the junction of the inferior vena cava with the liver. In some instances, unique geometric features on the exposed liver surface are used. Then, the corresponding position of these landmarks is identified intraoperatively by touching them with the tracked probe and recording the probe's position. Once the position of each anatomical landmark has been acquired, a point-based registration is computed that minimizes the root mean square distance between corresponding anatomical landmarks. Due to the possibility of deformation and the difficulty in localizing landmarks, the resulting transformation is not accurate enough for guidance, but it usually can provide an acceptable guess that is close enough to result in ICP reaching a suitable minimum.

This registration method was used to test the quality of the semiautomatic segmentation. If the semiautomatic segmentation can provide nearly the same alignment as a meticulous manual segmentation, then it would reduce pre-processing time significantly. Both segmented surfaces are used to calculate a registration on the same intraoperative data. As a result, the registrations generate two intraoperative surfaces, which differ only in position and orientation. The distance between these two surfaces was calculated and used to determine how similar registrations these two segmentations provide.

D. Intraoperative Deformation: The liver is a soft tissue that can undergo deformation due to a number of surgical loads (resection, immobilization, repositioning). Deformation could compromise the accuracy of targeting lesions if only a rigid mapping is used to register between the intraoperative data and the preoperative images. Thus, a biomechanical model of the liver using the finite element method (FEM) is implemented to handle deformation. FEM analysis provides a powerful tool for modeling soft tissue deformation and has been applied to the brain shift problem in neurosurgical procedures [39]. Efforts to implement finite element modeling in liver resections have been limited to virtual reality and surgical simulation, where accuracy of the deformation is sacrificed to achieve realistic deformations at real-time frame rates for the purposes of training and planning. To begin the analysis, a volumetric mesh is generated from the patient's preoperative images and it serves as the model used to solve a system of partial differential equations that simulates the patient's liver undergoing a deformation. The simulation is driven by boundary conditions that describe the forces interacting with the liver surface. Some regions of the liver are held fixed, while other move freely. The third and most important category of boundary condition deforms points on the liver surface to order to match them with intraoperative representation.

E. Surgical Navigation Software: The Operating Room Image-Oriented Navigation (ORION) system was created at Vanderbilt University to handle the tasks required for an image-guided surgical procedure. ORION was developed using Microsoft Visual C++6.0 and Win 32 API. Under the current framework, ORION is capable of rendering updates at a rate of 30-40 frames per second. For this study, new components were developed in ORION that involved fast surface registration, communication with the laser range scanner, and three-dimensional rendering of the liver surface. In addition, the group has collaborated with MeVis (Center for Medical Diagnostic Systems and Visualization Bremen, Germany) to incorporate their vascular segmentation and representation capabilities for surgical planning into ORION, so that it can display the probe position with respect to their models of the vasculature, tumors, and resection planes. A screen shot from ORION during one of the procedures is shown in FIG. 37.

F. Clinical Acquisition: Institutional Review Board (IRB) approval was obtained at both Vanderbilt University Medical Center and Washington University School of Medicine for the intraoperative acquisition of liver surface data. Informed consent was obtained from eight patients (5 at Vanderbilt University, 3 at Washington University) undergoing standard liver tumor resection procedures. Of these 8 cases, only one patient was undergoing resection for a primary tumor; the other seven cases presented with metastatic liver tumors. Three of the patients were female, five of the patients were male, and their mean age was $59.4 \pm 9.2$ years. The results presented from case 6 of this group have been previously published by the group in [35]. To determine the extent of liver motion due to respiration, the surgeon placed the tracked probe on the liver surface of the patient. The probe is held at the same location on the liver surface for 30-60 seconds, which corresponds to 4-10 breathing cycles. For the entire duration, the three-dimensional location of the probe tip is recorded at a rate of 40 Hz and used to analyze the behavior of motion due to respiration. First, noise was removed from the data points using a moving average filter. Then, the three-dimensional path representing the liver point's motion during these respiratory cycles was examined using principal component analysis (PCA). PCA reorganizes the coordinate system so that it is aligned with the three axis where the variance is the greatest. If PCA indicates that the variance along one of these axes is greater than the other two, it signifies the path that the point travels during respiration is primarily along one-dimension.

For the purpose of registration, planned periods of apnea were used to decrease respiratory related liver motion. These apneic periods were part of the approved IRB protocol and each occurred at the same point in the respiratory cycle, so that the liver would reside approximately in the same location for every registration. There were 2-5 brief apneic periods, each lasting no more than four minutes, over the course of the procedure. During each apneic period, physical space data was acquired for the registration process. First, point based landmarks were digitized with a sterilized, tracked probe for the purposes of determining an initial estimate of the registration that served as input to the ICP algorithm. After the initial alignment, surface data was captured, either with the probe or the range scanner. The probe was placed in contact with the liver and swept across the surface. The range scanner attaches to a surgical arm that stays out of the operating field while not in use. When ready to scan, the surgical arm is swiveled into the intraoperative scene, as shown in FIG. 36. After a brief setup for positioning the scanner and determining the correct parameters, the surface is scanned. The scanner has the potential to acquire anywhere from 15,000 to 45,000 points on the liver surface. The number of points acquired is dependent on the organ size and the area of liver surface visible to the scanner. In four of the eight cases, range scan data of the liver surface was available. In all but one case, surface data was acquired using an optically tracked probe.

Results

A. Respiratory Motion: Table 6 shows the results from the principle component analysis of respiratory motion. No respiratory data is available for case 2. Two sets of data from different time points during surgery were available for case 8. For each case, the fraction of motion that is attributed to the primary axis is shown, along with the average motion in mm between peak inhalation and peak exhalation that the liver moves along the primary axis. FIG. 38 shows time plots of respiratory data from cases 4 and 8. The three plots represent each of the three primary axes as determined by the PCA. The origin represents the mean position of this data.

TABLE 6

Principle Component Analysis of respiratory motion data. No respiratory data was acquired in case 2, and two separate sets of respiratory data were acquired on case 8.

| Case | Primary Axis Motion Fraction | Motion along primary axis |
|---|---|---|
| 1 | 87% | 12.5 ± 1.2 (n = 5) |
| 3 | 97% | 11.2 ± 3.5 (n = 4) |
| 4 | 91% | 17.1 ± 1.4 (n = 21) |
| 5 | 74% | 6.8 ± 1.8 (n = 13) |
| 6 | 80% | 14.1 ± 1.7 (n = 7) |
| 7 | 80% | 11.9 ± 2.0 (n = 6) |
| 8a | 96% | 24.6 ± 1.9 (n = 8) |
| 8b | 98% | 29.7 ± 1.2 (n = 8) |

B. Surface Registration: The segmented surfaces used for registration studies contained 45,000 to 80,000 vertices. However, differences between manual and level set segmented surfaces for an individual subject were no greater than 3,000 vertices. Tables 6 and 7 show the results from registration experiments. The cases were split into two categories based on the type of intraoperative data used. The second column provides the number of intraoperative surface points, rounded to the nearest 100. The values in the 3rd and 4th columns represent the root mean square surface residual error (with the maximum closest point distance given in parentheses) of the registrations from the manual and level set segmented surfaces, respectively. The final column contains the root mean square and maximum point distances between the two registrations. From Tables 6 and 7, it is clear how many more points are acquired when using the range scanner. While the individual surface registration errors are not significantly different, the differences between the two registrations are much higher when using a tracked probe, indicating that there are noticeable differences between the registrations obtained by using different segmentation methods.

TABLE 7

Surface registration experiments with cases with range scan data. The number of physical space points was rounded to nearest 100. The 3rd and 4th columns provide the root mean square residual and maximum closest point distance (in parentheses) for the registrations. The difference between the registrations is displayed in the final column.

| Case | Scan Points | Manual | Level Set | Difference |
|---|---|---|---|---|
| 1 | 19000 | 6.2 (18.7) | 6.4 (19.8) | 1.8 (3.2) |
| 2 | 20000 | 5.0 (18.4) | 5.0 (16.7) | 2.2 (3.3) |
| 6 | 29000 | 2.3 (11.9) | 2.3 (11.5) | 1.4 (2.7) |
| 7 | 48000 | 5.5 (19.2) | 5.2 (18.5) | 3.5 (5.7) |

TABLE 8

Surface registration experiments with cases with tracked probe data. The number of physical space points was rounded to nearest 100. The 3rd and 4th columns provide the root mean square residual and maximum closest point distance (in parentheses) for the registrations. The difference between the registrations is displayed in the final column.

| Case | Probe points | Manual | Level Set | Difference |
|---|---|---|---|---|
| 2 | 1600 | 6.5 (24.9) | 6.7 (23.4) | 2.3 (5.2) |
| 3 | 500 | 5.7 (20.9) | 5.0 (19.4) | 19.5 (35.6) |
| 4 | 1500 | 5.0 (14.6) | 4.9 (19.8) | 5.6 (7.7) |
| 5 | 700 | 6.0 (17.1) | 5.9 (17.1) | 6.5 (10.0) |
| 6 | 2400 | 3.0 (20.0) | 3.0 (21.2) | 1.2 (1.9) |
| 7 | 1900 | 6.4 (24.8) | 6.4 (26.4) | 2.9 (5.5) |
| 8 | 2200 | 6.5 (20.5) | 6.0 (17.9) | 3.7 (5.5) |

FIGS. 39 (range scan data) and 40 (tracked probe data) show a graphical representation of the registration results. In these figures, the intraoperative data is overlaid onto the corresponding tomographic slices. In three cases, both tracked probe data and range scan data of the liver surface were available, and each modality was used for a surface registration. A comparison of the resulting registrations is shown in FIG. 41, where both data sets are overlaid on the same tomographic slice using the respective registrations. These slices indicate how sparse the tracked probe data is in relation to the range scanner, and how there are greater errors in localizing and registering the tracked probe surfaces.

For three of the cases, the inferior edge of the liver could be manually identified in the range scan data, and it was broken into three regions for initial targeting studies. While serving as a target, these regions were removed from the registration process. The error metric for the target surface was computed by taking the root mean square distance between each point on the target and the point on the segmented surface which intersected with the target point's normal vector. The results of the targeting studies are found in Table 9. Since the stated goal of this research project is to provide targeting with errors less than 1 cm, the number of points on the target ridge that exceeded this limit are listed in the last column.

TABLE 9

Targeting results using the inferior ridge

| Case | Target | Number of Points | Mean Residual | Normal Distance | Points ≧1 cm |
|---|---|---|---|---|---|
| 1 | Right | 1700 | 5.1 ± 3.5 | 4.7 ± 2.5 | 18 (1.0%) |
|   | Middle | 1500 | 5.1 ± 3.5 | 5.6 ± 2.7 | 47 (3.0%) |
|   | Left | 2700 | 4.8 ± 3.5 | 9.3 ± 3.7 | 1171 (44.4%) |
| 2 | Right | 3000 | 5.0 ± 3.7 | 4.5 ± 3.7 | 304 (10.1%) |
|   | Middle | 1900 | 4.9 ± 3.6 | 7.9 ± 4.5 | 603 (31.5%) |
|   | Left | 1500 | 4.9 ± 3.7 | 9.0 ± 5.1 | 554 (38.0%) |
| 7 | Right | 1000 | 4.5 ± 2.9 | 5.2 ± 4.3 | 57 (5.6%) |
|   | Middle | 1600 | 4.4 ± 2.9 | 5.5 ± 5.2 | 365 (22.3%) |
|   | Left | 1300 | 4.5 ± 3.0 | 2.6 ± 2.5 | 15 (1.0%) |

C. Finite Element Modelling: Much of the error arising from the rigid registration can be attributed to non-rigid deformation that occurs in the intraoperative setting. For each case where range scan data was available, a tetrahedral mesh was generated from the image data for the purposes of the finite element model. Using the rigidly registered intraoperative data to determine the boundary conditions, the displacements were solved using the FEM model that was generated from the patient's preoperative data. FIG. 42 shows the results from the patient model, where the displacements at each node have been used to warp the preoperative image. The deformed image is fused with the preoperative data and the registered point cloud to show the difference between the registration before and after implementation of the finite element model.

Discussion

In this example, the framework for applying image guided surgery concepts to liver resections is provided. It is shown how the framework has been applied during initial clinical settings and analyzes some of the most significant issues that could affect the surface registration. With a successful registration, the ORION system can provide powerful navigation aids to the surgeon as illustrated by FIG. 36. It can display the position of a tracked surgical instrument in relation to preoperative tomographic volumes and rendered surfaces, including important subsurface vasculature and tumors. This will allow the surgeon to have real-time quantitative information regarding the proximity of critical vascular and biliary structures as well as preoperative resection plans.

Other researchers have focused their efforts on phantom studies [63] and percutaneous studies [63], but this work is unique in that it concentrates on acquiring and registering data from open abdominal hepatic tumor resections. The initial work was also based on phantom studies, which resulted in registration errors of 2.9 mm and targeting errors of 2.8 mm [21]. The updated system used the laser range scanner to reduce registration errors and target errors in phantom studies to under 0.8 and 2.0 mm respectively [35]. The clinical findings result in higher registration errors, due to the presence of a number of factors that can be eliminated during idealized phantom studies. The most important aspects are the decrease in the exposed surface region that can be acquired by the range scanner and the presence of intraoperative deformation. Other factors include the inaccuracies of the segmentation, and the introduction of added noise to the range scan data caused by surrounding structures and surgical instruments located in the scanner's field of view.

This study also examined the amount of respiratory motion in the liver observed during a procedure. The group first examined respiratory motion when Herline et al. [63] did some initial studies in two human patients. The results indicated the average motion of the liver was 10.3±2.5 mm. These results are consistent with the amplitude of respiratory motion in the findings. In addition, a principal component analysis is employed to determine how much of the motion is along one dimension, as has been done in related non-invasive imaging studies [63]. Their results indicate periodic one-dimensional motion along the cranial-caudal axis on the order of about 10-30 mm. However, in the intraoperative data, there is some misalignment present when the primary axis of the motion is transformed into image space and compared to the imaging axis that corresponds to the cranial-caudal direction. This misalignment could be caused by registration errors or patient positioning on the imaging gantry, but another significant cause could be the repositioning of the liver during surgery. Thus, the intraoperative orientation with respect to the cranial-caudal axis has been modified. This information will be valuable for future studies to account for this motion and lower the number of apneic periods.

The results from the registration experiments indicate that the ranges canner provides a better likelihood of an accurate, robust registration than the pen probe. The range scanner only requires 15-30 seconds to acquire a surface, which contains 20 to 30 times more points than the probe can acquire in the same time frame. In addition, the range scanner provides uniformly sampled data using a non-contact method. Both of these features limit the amount of error in surface acquisition compare to the tracked probe. These differences are showcased in FIG. 41. As a result, the range scanner provides data for a surface registration that is independent of segmentation method, as indicated in Tables 6. Table 7 shows the large differences in registration results with respect to segmentation method when using the tracked probe. As semiautomatic segmentation becomes a non-factor in the registration, hours of user interaction time can be saved before the procedure.

While the overall number of points is important to the performance of the registration, so is the information that it contains. If the range scanner captures a region that is relatively planar, then the ICP algorithm could determine multiple alignments that provide equally suitable matches. As a result, a misalignment could be determined to be equally as desirable as the correct registration. However, when geometrically unique regions of the liver are captured, many of the false matches are eliminated. The most practical feature in terms of exposure is the inferior edge of the liver, near the junction of the left and right lobes at segments III, IV, and V. In case 7, there was very little information about the ridge present in the range scan, which causes a visible misalignment, shown in FIG. 43. In this figure, the notch where the falciform ligament usually resides serves as a qualitative landmark. The misalignment causes this landmark to rotate clockwise, as indicated by the arrows. Also, Table 6 indicates that Case 7 has the highest difference in registration between the two segmentation methods among the cases with range scan data. This is another indicator that relatively planar surfaces do not produce a unique alignment and are susceptible to misregistration. To confirm the assertion that the ridge produces robust surface registrations, multiple registrations were performed on the same data while perturbing the initial alignment. The registration converged to the correct alignment over a higher range of perturbations when a pronounced ridge was present. As a result, the range scanner is now oriented at more of angle rather than an overhead perspective of the operating field, and in some cases, the liver is repositioned to make the ridge more accessible. This increases the likelihood that unique surface features are acquired from the liver.

In all cases, a significant component of the rigid registration error can be attributed to non-rigid deformation. The intraoperative forces and manipulation cause noticeable shape changes in the liver compared to the preoperative images. When deformation is encountered by the rigid ICP registration, it interprets this non-rigid motion as registration error. In some cases, such as case 7, the change in shape may be one of the factors inducing a misalignment. In each of the four cases displayed in FIG. 10, there is strong agreement between intraoperative data and the preoperative image surface after being deformed by the finite element model. This outcome is the direct result of the boundary conditions explicitly driving the boundary nodes to the intraoperative data. Since only an incomplete region of the liver surface is available during surgery, boundary conditions from these regions must recover most of the intraoperative deformation. The finite element model is desirable for this application because it determines a deformation that is based on the underlying biomechanics. In phantom studies, the FEM was able to recover deformations on the order of 3-4 cm to with in a subsurface target error of 4.0 mm [35]. Currently, the finite element studies are conducted retrospectively, and future studies will determine the logistics of incorporating the required computational resources into the operating room system.

While accuracy for image-guided systems is paramount, the amount of time required by this technology also plays a role in feasibility. Increased time under anaesthesia could provide a health risk to the patient. In the framework, most of the time-consuming tasks are part of preoperative preparation, and often take place several days before the procedure. None of the intraoperative tasks take more than a few minutes, and only surface acquisition and registration evaluation require apneic periods. Since all apneic periods are initiated at the same point of the respiratory cycle, a single surface registration should hold over many apneic periods. Major events, such as readjustment of the liver or resection, may require another registration. A summary of the events in image-guided surgery along with the time required to perform each task is located in Table 10.

TABLE 10

Approximate time requirements for the tasks in image-guided liver surgery. * indicates that these tasks need to be performed during an apneic period:

| Task | Approximate Time |
|---|---|
| (a) Preoperative Tasks | |
| Manual Segmentation | 3-4 hrs. |
| Automatic Segmentation | 15 min. |
| Marching Cubes | 5 min. |
| RBF Fitting | 5 min. |
| Range Scan Calibration | 5 min. |
| (b) Intraoperative Tasks | |
| * Landmark Localization and Registration | 30 sec. |
| * Surface Acquisition with Tracked Probe | 1-2 min. |
| Range Scan Setup (not optimized) | 1-2 min. |
| * Surface Acquisition with Range Scanner | 15-20 sec. |
| ICP Registration using k-d trees | 1-5 min. |
| FEM Model | 2-3 min. |
| Image Deformation | 2-3 min. |

Validation of the registration with respect to subsurface structures will be a difficult task. In three of the cases, the ridges of the liver were able to serve in a manner similar to targets. In these cases, the mean error was less than 1.0 cm, which is the stated accuracy goal this study. However, in a few cases, there were a significant amount of points that were over this value. Inaccuracies in calculating the normals for the intraoperative point cloud, along with issues of correspondence and deformation caused these errors. A more rigorous set of validation experiments are currently being developed, which will provide an accurate assessment of subsurface target registration error. These studies involve implanting external markers (barium, microcoils, 1 mm stainless steel beads) by guiding a delivery mechanism to the centroid of the target as indicated by the results of the surface registration. The target and surrounding area will then be resected, and imaging studies will determine the location of the implanted marker with respect to the target.

Another avenue of future work is the fusion of data from multiple intraoperative modalities to provide a more accurate intraoperative description of the liver. The range scan data provides a wealth of information about the exposed surface of the liver, the fusion of additional intraoperative modalities could provide a more accurate registration. While localization with the tracked probe is much slower and more prone to error, it could be used to enhance the range scan surface by specifically acquiring points on the inferior edge and regions which are not visible to the scanner. Intraoperative ultrasound (IOUS) is another important tool for navigation during liver resection cases, and it provides a wealth of subsurface information that optical tracking and range scanning cannot. Subsurface data could be valuable in the finite element model as well as targeting studies. the lab has previously reported on incorporating ultrasound into other image-guided surgical applications.

In brief, this example shows some initial data regarding intraoperative surface registration for open abdominal hepatic tumor resection procedures. Respiration motion has been quantified as one-dimensional and periodic. This motion is primarily aligned in the cranial-caudal direction, although the liver is slightly reoriented during the surgical process. Registrations were robust and accurate when using dense surface data acquired intraoperatively from the range scanner. Additionally, these registrations performed better when the range scan data accurately acquired the unique geometric information from the ridges on the liver surface. Using the ridge as a target surface, the error calculated from average normal distance was less than 1 cm.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

List of References

[1] T. Hartkens, D. L. G. Hill, A. D. Castellano-Smith, D. J. Hawkes, C. R. Maurer, A. J. Martin, W. A. Hall, H. Liu, and C. L. Truwit, "Measurement and analysis of brain deformation during neurosurgery," *IEEE Transactions on Medical Imaging*, vol. 22, pp. 82-92, January 2003.

[2] A. Nabavi, P. M. Black, D. T. Gering, C. F. Westin, V. Mehta, R. S. Pergolizzi, M. Ferrant, S. K. Warfield, N. Hata, R. B. Schwartz, W. M. Wells, R. Kikinis, and F. A.

Jolesz, "Serial intraoperative magnetic resonance imaging of brain shift," *Neurosurgery*, vol. 48, pp. 787-797, 2001.

[3] A. Nabavi, C. T. Mamisch, D. T. Gering, D. F. Kacher, R. S. Pergolizzi, W. M. Wells, R. Kikinis, P. M. Black, and F. A. Jolesz, "Image-guided therapy and intraoperative MRI in neurosurgery," *Minimally Invasive Therapy & Allied Technologies*, vol. 9, pp. 277-286, August 2000.

[4] C. Nimsky, O. Ganslandt, M. Buchfelder, and R. Fahlbusch, "Intraoperative magnetic resonance tomography—experiences in neurosurgery," *Nervenarzt*, vol. 71, pp. 987-994, 2000.

[5] C. Nimsky, O. Ganslandt, S. Cerny, P. Hastreiter, G. Greiner, and R. Fahlbusch, "Quantification of, visualization of, and compensation for brain shift using intraoperative magnetic resonance imaging," *Neurosurgery*, vol. 47, pp. 1070-9; discussion 1079-80, 2000.

[6] A. L. Bradley, W. C. Chapman, J. K. Wright, J. W. Marsh, S. Geevarghese, T. K. Blair, and C. W. Pinson, "Surgical experience with hepatic colorectal metastasis," *Am. Surg.*, vol. 65, pp. 560-567, 1999.

[7] J. Scheele, R. Stang, A. Altendorf-Hofmann, and e. al., "Resection of colorectal liver metastasis," *World J. Surg.*, vol. 19, pp. 59-71, 1995.

[8] Y. Fong and L. H. Blumgart, "Surgical options in the treatment of hepatic metastases from colorectal cancer," *Curr. Prob. Surg.*, vol. 35, pp. 336-413, 1995.

[9] M. D. Stone, B. Cady, and R. L. Jenkins, "Surgical therapy for recurrent liver metastases from colorectal cancer," *Arch Surg*, vol. 125, pp. 718-722, 1990.

[10] A. C. Society, "Cancer Facts and Figures," American Cancer Society, Atlanta 2004.

[11] J. O. Garden and H. Bismuth, "Anatomy of the liver," in *Hepatobiliary and Pancreated Surgery, 5th Edition*, S. D. Carter, Ed. London: Chapman and Hall Medical, 1996, pp. 1-4.

[12] P. A. Sheiner and S. T. Brower, "Treatment of metastatic cancer to the liver," *Seminars in liver Disease*, vol. 14, pp. 169-177, 1994.

[13] J. Yamamoto, K. Sugihara, T. Kosuge, and e. al., "Pathologic support for limited hepatectomy in the treatment of liver metastases from colorectal cancer," *Ann. Surg.*, vol. 221, pp. 74-78, 1995.

[14] R. P. DeMatteo, C. Palese, W. R. Jarnagin, and e. al., "Anatomic segmental hepatic resection is superior to wedge resection as an oncologic operation for colorectal liver metastates," *J. Gastrointest. Surg.*, vol. 4, pp. 178-184, 2000.

[15] T. U. Cohnert, H. G. Rau, E. Butler, and e. al., "Preoperative risk assessment of hepatic resection for malignant disease," *World J. Surg.*, vol. 21, pp. 396400, 1997.

[16] W. R. Jarnagin, M. Gonen, Y. Fong, and e. al., "Improvement in peroperative outcome after hepatic resection: analysis of 1803 consecutive cases over the past decade," *Ann. Surg.*, vol. 236, pp. 397-406, 2002.

[17] C. Laurent, A. Sa Cunha, P. Couderc, and e. al., "Influence of postoperative morbidity on long-term survival following liver resection for colorectal metastases," *Br. J. Surg.*, vol. 90, pp. 1131-1136, 2003.

[18] M. J. Schindl, D. N. Redhead, K. C. H. Fearon, and e. al., "The value of residual liver volume as a predictor of hepatic dysfunction and infection after major liver resection," *Gut*, vol. 55, pp. 289-296, 2005.

[19] T. Sunthau, M. Vetter, P. Hassenpflug, H.-P. Meinzer, and O. Hellwich, "A concept for augmented reality visualization based on a medical application in liver surgery," in *Proc. of the ISPRS Commision V Symposium*, Corfu, Greece, 2002, pp. 274-280.

[20] Y. Masutani and K. Fumihiko, "Modally controlled free form deformation for non-rigid registration in image-guided liver surgery," in *Medical Image Computing and Computer-Assisted Inverventions* 2001. vol. 2208, S. Verlag, Ed. Berlin, 2001, pp. 1275-1278.

[21] N. Ayache, "Epidaure: a research project in medical image analysis, simulation, and robotics at INRIA," *IEEE Trans Med Imaging*, vol. 22, pp. 1185-1201, 2003.

[22] INRIA, "Project-team epidaure: Epidaure, project images, diagnostic, automatique, robotique medical imaging, & robotics," INRIA 2003.

[23] J. M. Blackall, A. P. King, G. P. Penney, A. Adam, and D. J. Hawkes, "A statistical model of respiratory motion and deformation of the liver," in *Medical Image Computing And Computer Assisted Interventions* 2001. vol. 2208, S. Verlag, Ed. Berlin: Springer Verlag, 2001, pp. 1338-1340.

[24] G. P. Penney, J. M. Blackall, M. S. Hamady, T. Sabharawal, A. Adam, and D. J. Hawkes, "Registration of freehand 3D ultrasound and magnetic resonance liver images," *Medical Image Analysis*, vol. 8, pp. 81-91, 2004.

[25] P. Bao, J. Warmath, R. L. Galloway, and A. J. Herline, "Ultrasound-to-computer-tomography registration for image-guided laparoscopic liver surgery," *Surg. Endosc.*, p. electronic publication, 2005.

[26] B. B. Frericks, F. C. Caldarone, B. Nashan, and e. al., "3D CT modeling of hepatic vessel architecture and volume calculation in living donated liver transplantation," *Eur J Radiol*, vol. 14, pp. 326-333, 2004.

[27] H. Lang, A. Radtke, C. Liu, N. R. Fruhauf, H. O. Peitgen, and C. E. Broelsch, "Extended left hepatectomy—modified operation planning based on three-dimensional visualization and liver anatomy," *Langenbecks Arch Surg.*, vol. 389, pp. 306-310, 2004.

[28] D. Selle, B. Preim, A. Schenk, and H. O. Peitgen, "Analysis of vasculature of liver surgical planning," *IEEE Trans Med Imaging*, vol. 21, pp. 1344-1257, 2002.

[29] D. Knaus, E. Friets, J. Bieszczad, R. C. Chen, M. I. Miga, R. L. Galloway, and D. Kynor, "System for laparoscopic tissue tracking," in *International Symposium on Biomedical Imaging* 2006 Washington, D.C.: IEEE, 2006.

[30] Z. Cao, "Segmentation of medical images using level set-based methods," in *Electrical Engineering, Computer Engineering, and Computer Science* Nashville: Vanderbilt University, 2004.

[31] L. Hermoye, I. Laamari-Azjal, Z. J. Cao, L. Annet, J. Lerut, B. M. Dawant, and B. E. Van Beers, "Liver segmentation in living liver transplant donors: Comparison of semiautomatic and manual methods," *Radiology*, vol. 234, pp. 171-178, January 2005.

[32] W. Lorensen and H. E. Cline, "Marching cubes: A high resolution 3d surface construction algorithm," *ACM Computer Graphics*, vol. 21, pp. 163-169, 1987.

[33] J. L. Bentley, "Multidimensional binary search trees used for associative searching," *Communications of the ACM*, vol. 18, pp. 509-517, 1975.

[34] Z. Zhang, "Iterative point matching for registgration of free-form curves and surfaces," *Int. J of Computer Vision*, vol. 13, pp. 119-152, 1994.

[35] D. M. Cash, T. K. Sinha, W. C. Chapman, R. L. Galloway, and M. I. Miga, "Fast, accurate surface acquisition using a laser range scanner for image-guided liver surgery," *Medical Imaging* 2002: *Visualization, display, and image-guided procedures: Proc. of the SPIE* 2002, vol. 4681, pp. 100-110, 2002.

[36] D. M. Cash, T. K. Sinha, W. C. Chapman, H. Terawaki, B. M. Dawant, R. L. Galloway, and M. I. Miga, "Incorporation of a laser range scanner into image-guided liver sur-

[37] D. M. Cash, "Surface registration and deformation compensation in image-guided liver surgery," in *Biomedical Engineering* Nashville: Vanderbilt University, 2004, p. 183.

[38] D. M. Cash, M. I. Miga, T. K. Sinha, R. L. Galloway, and W. C. Chapman, "Compensating for intraoperative soft-tissue deformations using incomplete surface data and finite elements," *IEEE Transactions on Medical Imaging*, vol. 24, pp. 1479-1491, November 2005.

[39] M. I. Miga, D. M. Cash, Z. Cao, R. L. Galloway, B. M. Dawant, and W. C. Chapman, "Intraoperative registration of the liver for image-guided surgery using laser range scanning & deformable models," in *SPIE Medical Imaging 2003: Visualization, Display, and Image-Guided Procedures*, San Diego, Calif., 2003.

[40] B. M. Dawant, S. Pan, and R. Li, "Robust segmentation of medical images using geometric deformable models and a dynamic speed function," in *Medical Image Computing and Computer-Assisted Intervention* 2001. vol. 2208, N. A. Viergever, Ed.: Springer Verlag, 2001.

[41] P. J. Besl and N. D. McKay, "A Method for Registration of 3-D Shapes," *IEEE Transactions on Pattern Analysis and Machine Intelligence*, vol. 14, pp. 239-256, 1992.

[42] H. Chui and A. Rangarajan, "A new point matching algorithm for non-rigid registration," *Computer Vision and Image Understanding*, vol. 89, pp. 114-141, 2003.

[43] D. M. Cash, S. C. Glasgow, L. W. Clements, M. I. Miga, B. M. Dawant, Z. Cao, R. L. Galloway Jr., and W. C. Chapman, "Image-guided liver surgery: Concepts and initial clinical experiences," *Journal of Gastrointestinal Surgery*, vol. (in press), 2006.

[44] L. W. Clements, D. M. Cash, W. C. Chapman, R. L. Galloway, and M. I. Miga, "Robust surface registration using salient anatomical features in image-guided liver surgery," in *SPIE Medical Imaging 2006: Visualization, Image-guided Procedures, and Display* San Diego, Calif.: SPIE, 2006.

[45] J. P. W. Pluim, J. B. A. Maintz, and M. A. Viergever, "Image registration by maximization of combined mutual information and gradient information," *IEEE Transactions on Medical Imaging*, vol. 19, pp. 809814, August 2000.

[46] J. Rosenman, "Incorporating functional imaging information into radiation treatment," *Seminars in Radiation Oncology*, vol. 11, pp. 83-92, 2001.

[47] S. Sgouros, S. Seri, and K. Natarajan, "The clinical value of electroencephalogram/magnetic resonance imaging co-registration and three-dimensional reconstruction in the surgical treatment of epileptogenic lesions," *Childs Nervous System*, vol. 17, pp. 139-144, 2001.

[48] M. I. Miga, D. M. Cash, Z. Cao, R. L. Galloway Jr., B. M. Dawant, and W. C. Chapman, "Intraoperative registration of the liver for image-guided surgery using laser range scanning and deformable models," in *Medical Imaging 2003: Visualization, Image-guided Procedures, and Display*, San Diego, 2003, pp. 350-359.

[49] L. W. Clements, D. M. Cash, W. C. Chapman, R. L. Galloway, and M. I. Miga, "Robust surface registration using salient anatomical features in image-guided liver surgery," *Proc. of SPIE: Medical Imaging* 2006, vol. 6141, Feb. 11-16, 2006 2006.

[50] P. Dumpuri and M. I. Miga, "Model-updated image guidance: A statistical approach to gravity-induced brain shift," in *Medical Image Computing and Computer-Assisted Intervention—Miccai* 2003, Pt 1. vol. 2878 Berlin: SPRINGER-VERLAG BERLIN, 2003, pp. 375-382.

[51] P. Dumpuri, R. C. Thompson, B. M. Dawant, A. Cao, and M. I. Miga, "An atlas-based method to compensate for brain shift: Preliminary results," *Medical Image Analysis*, p. (in press), 2006.

[52] P. Dumpuri, R. C. Thompson, T. K. Sinha, and M. I. Miga, "Automated brain shift correction using a pre-computed deformation atlas," *Proc. of SPIE: Medical Imaging* 2006, vol. 6141, 2/11-16/2006 2006.

[53] C. Davatzikos, "Measuring biological shape using geometry-based shape transformations," *Image and Vision Computing*, vol. 19, pp. 63-74, 2001.

[54] C. Davatzikos and J. L. Prince, "Convexity analysis of active contour problems," *Image and Vision Computing*, vol. 17, pp. 27-36, 1999.

[55] C. Davatzikos, D. G. Shen, A. Mohamed, and S. K. Kyriacou, "A framework for predictive modeling of anatomical deformations," *IEEE Transactions on Medical Imaging*, vol. 20, pp. 836-843, 2001.

[56] S. K. Kyriacou and C. Davatzikos, "A biomechanical model of soft tissue deformation, with applications to non-rigid registration of brain images with tumor pathology," *Medical Image Computing and Computer-Assisted Intervention—Miccai '98*, vol. 1496, pp. 531-538, 1998.

[57] S. K. Kyriacou, C. Davatzikos, S. J. Zinreich, and R. N. Bryan, "Nonlinear elastic registration of brain images with tumor pathology using a biomechanical model," *IEEE Transactions on Medical Imaging*, vol. 18, pp. 580-592, 1999.

[58] S. K. Kyriacou, D. G. Shen, and C. Davatzikos, "A framework for predictive modeling of intra-operative deformations: A simulation-based study," *Medical Image Computing and Computer-Assisted Intervention—Miccai* 2000, vol. 1935, pp. 634-642, 2000.

[59] C. R. Maurer, G. B. Aboutanos, B. M. Dawant, R. J. Maciunas, and J. M. Fitzpatrick, "Registration of 3D images using weighted geometrical features," *IEEE Transactions on Medical Imaging*, vol. 15, pp. 836-849, 1996.

[60] M. I. Miga, J. M. Fitzpatrick, R. L. Galloway, and K. D. Paulsen, "Incorporation of surface-based deformations for updating images intraoperatively," in *SPIE Medical Imaging* 2001: *Visualization, Display, and Image-guided Procedures* San Diego, Calif.: SPIE, 2001.

[61] F. J. Carter, T. G. Frank, P. J. Davies, D. McLean, and A. Cuschieri, "Measurements and modelling of the compliance of human and porcine organs," *Medical Image Analysis*, vol. 5, pp. 231-236, December 2001.

[62] M. Stevanovic, M. Yovanovich, and J. R. Culham, "Modeling contact between rigid sphere and elastic layer bonded to rigid substrate," *IEEE Trans on Components and Package Technologies*, vol. 24, pp. 207-212, 2001.

[63] A. J. Herline, J. D. Stefansic, J. P. Debelak, S. L. Hartmann, C. W. Penson, R. L. Galloway, and W. C. Chapman, "Image-guided surgery: Preliminary feasibility studies of frameless stereotactic liver surgery," Arch. Surg. 134, pp. 644-650, 1999.

[64] A. J. Herline, J. L. Herring, J. D. Stefansic, W. C. Chapman, J. Robert L. Galloway, and B. M. Dawant, "Surface registration for use in interactive, image-guided liver surgery," Comput. Aided Surg. 5, pp. 11-17, 2000.

[65] P. J. Besl and N. D. McKay, "A method for registration of 3-d shapes," IEEE Trans. Pattern Anal. Machine Intell. 14(2), pp. 239-255, 1992.

[66] D. M. Cash, T. K. Sinha, W. C. Chapman, J. Robert L. Galloway, and M. I. Miga, "Fast accurate surface acquisition using a laser scanner for image-guided surgery," SPIE: Med. Imag., 2002.

[67] D. M. Cash, T. K. Sinha, W. C. Chapman, H. Terawaki, B. M. Dawant, J. Robert L. Galloway, and M. I. Miga, "Incorporation of a laser range scanner into image-guided liver surgery: Surface acquisition, registration, and tracking," Med. Phys. 30, pp. 1671-1682, 2003.

[68] D. M. Cash, M. I. Miga, T. K. Sinha, R. L. Galloway, and W. C. Chapman, "Compensating for intraoperative soft-tissue deformations using incomplete surface data and finite elements," IEEE Trans. Med. Imaging 24(11), pp. 1479-1491, 2005.

[69] C. R. Maurer, G. B. Aboutanos, B. M. Dawant, R. J. Maciunas, and J. M. Fitzpatrick, "Registration of 3-d images using weighted geometrical features," IEEE Trans. Med. Imaging 15(6), pp. 836-849, 1996.

[70] K. S. Arun, T. S. Huang, and S. D. Blostein, "Least-squares fitting of two 3-d point sets," IEEE Trans. Pattern Anal. Mach. Intell. 9(5), pp. 698-700, 1987.

[71] S. J. Ahn, W. Rauh, H. S. Cho, and H.-J. Warnecke, "Orthogonal distance fitting of implicit curves and surfaces," IEEE Trans. Pattern Anal. Mach. Intell. 24(5), pp. 620-638, 2002.

[72] L. A. Platenik, M. I. Miga, D. Roberts, K. E. Lunn, F. E. Kennedy, A. Hartov, and K. D. Paulsen, "In vivo quantification of retraction deformation modeling for updated image-guidance during neurosurgery," *IEEE Trans. Biomed. Eng.*, vol. 49, no. 8, pp. 823-835, August 2002.

[73] S. Balay, W. D. Gropp, L. C. McInnes, and B. F. Smith, *Efficient Management of Parallelism in Object Oriented Numerical Software Libraries*. Cambridge, Mass.: Birkhauser, 1997, pp. 163-202.

[74] Y. Saad and M. H. Schultz, "GMRES: A generalized minimal residual algorithm for solving nonsymmetric linear systems," in *SIAM J. Sci. Statist. Comput.*, vol. 7, 1986, pp. 856-869.

[75] J. Fitzpatrick, J. West, and C. Maurer, "Predicting error in rigid-body point-based registration," *IEEE Trans. Med. Imag.*, vol. 17, no. 5, pp. 694-702, October 1998.

[76] A. E. Johnson and S. B. Kang, "Registration and integration of textured 3D data," *Image Vis. Comput.*, vol. 17, no. 2, pp. 135-147, February 1999.

[77] G. Sharp, S. Lee, and D. Wehe, "ICP registration using invariant features," *IEEE Trans. Pattern Anal. Mach. Intell.*, vol. 24, no. 1, pp. 90-102, January 2002.

[78] G. Godin, D. Laurendeau, and R. Bergevin, "A method for the registration of attributed range images," in *Proc. 3DIM* 2001, May 2001, pp. 179-186.

[79] P. Bao, J. Warmath, R. L. Galloway, and A. Herline, "Ultrasound to CT registration for image-guided laparoscopic liver surgery," Surgical Endosc., 2004, to be published.

[80] R. Malladi, J. A. Sethian, and B. C. Vemuri, "Shape modeling with front propagation: A level set approach," IEEE Transactions of Pattern Analysis and Machine Intelligence, vol. 17, pp. 158-175, 1995.

[81] J. Carr, B. Beatson, R. K. adn McCallum, W. Fright, T. McLennan, and T. Mitchell, "Smooth surface reconstruction from noisy range data," in ACM GRAPHITE 2003, Melbourne, Austraila, 2003, pp. 119-126.

What is claimed is:

1. A method of surface registration in image guided surgery, comprising the steps of:

a. preoperatively acquiring an image of an organ of interest of a living subject;

b. generating a first surface of the organ of interest of the living subject from the preoperatively acquired image;

c. designating a set of target points, T={tn}, n=1, 2, 3, ..., NT, from the first surface of the organ of interest, wherein the set of target points T contains one or more patch points corresponding to homologous anatomical features of the first surface of the organ of interest, and wherein each of the set of target points tm is indexed with a binary index, pTm, such that when pTm=0, the target point tm is a non-patch point, and when pTm=1, the target point tm is a patch point, the one or more patch points of the target points define a particular salient anatomical feature of the first surface of the organ of interest;

d. intraoperatively acquiring an incomplete image of the organ of interest of the living subject;

e. generating a second surface of the organ of interest of the living subject from the intraoperatively acquired incomplete image, wherein the second surface is an incomplete surface of the organ of interest of the living subject;

f. designating a set of source points, S={sm}, m=1, 2, 3, ..., NS, from the second surface of the organ of interest, wherein the set of source points S contain one or more patch points corresponding to homologous anatomical features of the second surface of the organ of interest, which is related to the corresponding homologous anatomical features of the first surface of the organ of interest, and wherein each of the set of source points sm is indexed with a binary index, pSm, such that when pSm=0, the source point sm is a non-patch point, and when pSm=1, the source point sm is a patch point, the one or more patch points of the source points define a particular salient anatomical feature of the second surface of the organ of interest;

g. determining a point correspondence between the set of source points S and the set of target points T, whereby a closest point operator, C={Cm} is determined;

h. biasing the point correspondence between the one or more source patch points and the one or more target patch points by a weighting factor, wPC, so as to assign weighted correspondence of a weighted point-based registration to the particular salient anatomical features and to bias the closest point operator Cm, via the following relationship:

$$d_{m,n} = \begin{cases} w_{PC} \|s_m - t_n\| & \text{if } p_m^S = p_n^T = 1 \\ \|s_m - t_n\| & \text{otherwise} \end{cases}$$

wherein $0 < w_{PC} \ll 1$, dm,n is Euclidian distance between a source point sm and a target point tn;

i. aligning the second surface of the organ of interest to the first surface of the organ of interest using the weighted point-based registration (PBR) between the set of source points S and the set of target points T by finding a rigid-body transformation ($\Omega$) between the set of source points and the set of target points that minimizes an objective function of:

$$f(\Omega) = \sqrt{\sum_{m=1}^{N_M} w_m \|C_m(s_m, T) - \Omega(s_m)\|^2}$$

wherein {wm} is a set of weights letting wm=1 for pSm=0 and wm=WPBR for pSm=1, and wherein WPBR is a function of iteration, i, in the form of:

$$W_{PBR}(i) = W_{PBR,base} + [W_{PBR,max} - W_{PBR,base}] \exp[-\alpha(i-1)]$$

wherein i=1, 2, 3, ... N, N being the number of iteration, WPBR,max is a maximum patch weight factor and corresponds a patch weight at a first iteration, WPBR,base is a baseline patch weight factor, with $1 \leq$ WPBR, base $\leq$ WPBR, max, and $\alpha$ is a relaxation constant with $0 \leq \alpha \leq 1$, wherein the aligned second surface of the organ of interest up; and j. repeating steps (f)-(i) using the aligned second surface of the organ of interest until the root mean square (RMS) closest point distances between the source and target points have reached a predetermined value.

2. The method of claim 1, wherein the pre-operatively acquired image of the organ of interest of the living subject comprises image data with respect to the surface geometry of the organ of interest.

3. The method of claim 2, wherein the image data with respect to the surface geometry of the organ of interest is obtained through the use of at least one of positron emission tomography device, electroencephalography device, computer tomography device, functional magnetic resonance imaging device, magnetic resonance imaging device, and ultrasound imaging device.

4. The method of claim 1, wherein the step of generating a first surface of the organ of interest of the living subject comprises the step of extracting details of the first surface using at least one of the following features:
   a. user identification of surface features or visible structures;
   b. surface curvature;
   c. surface shape;
   d. surface orientation within the living subject;
   e. distribution of surface normal orientation; and
   f. potential for deformation of the anatomic structure.

5. The method of claim 1, wherein the step of intra-operatively acquiring images of the organ of interest of the living subject is performed with one of the following methods:
   a. swabbing the surface of the anatomic structure with a tracked instrument;
   b. laser range scanning of the anatomic structure for surface determination;
   c. intra-operative ultrasound scanning of the anatomic structure;
   d. imaging of the anatomic structure using a tracked laparoscope or endoscope; and
   e. surface extraction of the anatomic structure from a binocular scene such as provided by a binocular laparoscope or endoscope.

6. A method of surface registration in image guided surgery, comprising the steps of:
   a. pre-operatively acquiring an image of an anatomic structure of an organ of a living subject;
   b. generating a first surface of the anatomic structure of the organ from the preoperatively acquired image of the anatomic structure of the organ;
   c. constructing one or more first patches of the first surface of the anatomic structure, wherein each of the first patches contains a surface subset of physical space data related to a particular salient anatomical feature of the first surface of the anatomic structure, and assigning a weighted correspondence of a weighted point-based registration to the particular salient anatomical feature of each of the first patches;
   d. intra-operatively acquiring an incomplete image of the anatomic structure of the organ;
   e. generating a second surface of the anatomic structure of the organ from the intraoperatively acquired incomplete image of the anatomic structure of the organ, wherein the second surface is an incomplete surface of the anatomic structure of the organ;
   f. constructing one or more second patches of the second surface of the anatomic structure, wherein each second patch contains a surface subset of physical space data from the second surface related to a corresponding salient anatomical feature of the first surface of the anatomic structure;
   g. aligning the one or more second patches to the corresponding one or more first patches, wherein each second patch is dynamically biased to a corresponding first patch using the weighted point-based registration; and
   h. completing a registration of the second surface to the first surface with physical space data not contained in the first and second patches to indicate surgical position in both image space and physical space.

7. The method of claim 6, wherein the pre-operatively acquired images of the anatomic structure comprise image data with respect to the surface geometry of the anatomic structure.

8. The method of claim 7, wherein the image data with respect to the surface geometry of the anatomic structure is obtained through the use of at least one of positron emission tomography device, electroencephalography device, computer tomography device, functional magnetic resonance imaging device, magnetic resonance imaging device, and ultrasound imaging device.

9. The method of claim 6, wherein the step of generating a first surface of the anatomic structure of the organ comprises the step of extracting details of the first surface using at least one of the following features:
   a. user identification of surface features or visible structures;
   b. surface curvature;
   c. surface shape;
   d. surface orientation within the organ;
   e. distribution of surface normal orientation; and
   f. potential for deformation of the anatomic structure.

10. The method of claim 6, wherein the step of intra-operatively acquiring images of the anatomic structure of the organ is performed with one of the following methods:
    a. swabbing the surface of the anatomic structure with a tracked instrument;
    b. laser range scanning of the anatomic structure for surface determination;
    c. intra-operative ultrasound scanning of the anatomic structure;
    d. imaging of the anatomic structure using a tracked laparoscope or endoscope; and surface extraction of the anatomic structure from a binocular scene such as provided by a binocular laparoscope or endoscope.

11. The method of claim 6, wherein the step of aligning the one or more second patches to the corresponding one or more first patches comprises the step of giving more weight to the patches than to the rest of the surfaces.

12. The method of claim 11, wherein the step of completing a registration of the second surface to the first surface with physical space data not contained in the first and second patches comprises the step of increasing weight to the rest of the surfaces when final adjustments in the registration are made with all available surface information.

13. The method of claim 6, wherein the step of completing a registration of the second surface to the first surface with physical space data not contained in the first and second patches is performed with the weighted point-based registration.

14. The method of claim 13, wherein the weighted point-based registration comprises the step of using a salient-feature weighted correspondence.

15. The method of claim 6, wherein the anatomic structure of the organ comprises a liver, heart, kidney, lung, stomach, or brain.

16. The method of claim 15, wherein when the anatomic structure comprises a liver, the salient-feature comprises a falciform ligament region.

17. A method of surface registration in image guided surgery, comprising the steps of:
　a. generating a first surface of an anatomic structure of an organ from pre-operatively acquired images of the anatomic structure of the organ;
　b. generating a second surface of the anatomic structure of the organ from intra-operatively acquired incomplete images of the anatomic structure of the organ, wherein the second surface is an incomplete surface of the anatomic structure of the organ;
　c. constructing one or more second patches corresponding to the second surface of the anatomic structure, wherein each second patch contains a surface subset of physical space data from the second surface related to a corresponding particular salient anatomical feature of the first surface of the anatomic structure, and assigning a weighted correspondence of a weighted point-based registration to the particular salient anatomical feature;
　d. aligning the one or more second patches to the corresponding one or more first patches, wherein each second patch is dynamically biased to a corresponding first patch using the weighted point-based registration; and
　e. completing a registration of the second surface to the first surface with physical space data not contained in the first and second patches to indicate surgical position in both image space and physical space.

18. The method of claim 17, wherein the step of completing a registration of the second surface to the first surface with physical space data not contained in the first and second patches is performed with the weighted point-based registration.

19. The method of claim 18, wherein the weighted point-based registration comprises the step of using a salient-feature weighted correspondence.

20. A system of surface registration in image guided surgery, comprising:
　a. a first imaging acquiring device for pre-operatively acquiring images of an anatomic structure of an organ of a living subject;
　b. a second imaging acquiring device for intra-operatively acquiring incomplete images of the anatomic structure of the organ; and
　c. at least one computer coupled with the first image acquiring device and the second image acquiring device and adapted for performing the steps of:
　　i). generating a first surface of the anatomic structure of the organ from the pre-operatively acquired images of the anatomic structure of the organ;
　　ii). constructing one or more first patches of the first surface of the anatomic structure, wherein each of the first patchs contains a surface subset of physical space data related to a particular salient anatomical feature of the first surface of the anatomic structure, and assigning a weighted correspondence of a weighted point-based registration to the particular salient anatomical feature of each of the first patches;
　　iii). generating a second surface of the anatomic structure of the organ from the intra-operatively acquired incomplete images of the anatomic structure of the organ, wherein the second surface is an incomplete surface of the anatomic structure of the organ;
　　iv). constructing one or more second patches of the second surface of the anatomic structure, wherein each second patch contains a surface subset of physical space data from the second surface related to a corresponding salient anatomical feature of the first surface of the anatomic structure;
　　v). aligning the one or more second patches to the corresponding one or more first patches, wherein each second patch is dynamically biased to a corresponding first patch using the weighted point-based registration; and
　　vi). completing a registration of the second surface to the first surface with physical space data not contained in the first and second patches to indicate surgical position in both image space and physical space.

21. The system of claim 20, further comprising a display device coupled to the at least one computer for displaying the registration dynamically to facilitate a diagnostic or surgical procedure.

22. The system of claim 20, wherein the first imaging acquiring device comprises at least one of positron emission tomography device, electroencephalography device, computer tomography device, functional magnetic resonance imaging device, magnetic resonance imaging device, and ultrasound imaging device.

23. The system of claim 20, wherein the second imaging acquiring device comprises a laser range scanner that is capable of obtaining frequency, intensity and geometric data with respect to the cortical surface of the organ simultaneously.

24. The system of claim 20, wherein the second imaging acquiring device comprises an ultrasound imaging device.

25. The system of claim 20, wherein the second imaging acquiring device comprises a tracked instrument, an optical stylus, a tracked laparoscope or endoscope, or a binocular laparoscope or endoscope.

26. The method of claim 1, wherein the incomplete image of the organ of interest of the living subject is a sparse image of the organ.

27. The system of claim 20, wherein the incomplete image of the anatomic structure of the organ is a sparse image of the the anatomic structure.

* * * * *